(12) United States Patent
Braje et al.

(10) Patent No.: US 8,629,148 B2
(45) Date of Patent: Jan. 14, 2014

(54) SUBSTITUTED OXINDOLE-DERIVATIVES AND THE USE THEREOF FOR THE TREATMENT OF VASOPRESSIN-DEPENDENT ILLNESSES

(75) Inventors: Wilfried Braje, Ludwigshafen (DE); Astrid Netz, Ludwigshafen (DE); Thorsten Oost, Biberach an der Riss (DE); Wolfgang Wernet, Ludwigshafen (DE); Andrea Hager-Wernet, legal representative, Neustadt an der Weinstrasse (DE); Liliane Unger, Ludwigshafen (DE); Wilfried Hornberger, Ludwigshafen (DE); Wilfried Lubisch, Heidelberg (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 183 days.

(21) Appl. No.: 12/810,561

(22) PCT Filed: Dec. 23, 2008

(86) PCT No.: PCT/EP2008/068254
§ 371 (c)(1),
(2), (4) Date: Nov. 16, 2010

(87) PCT Pub. No.: WO2009/083559
PCT Pub. Date: Jul. 9, 2009

(65) Prior Publication Data
US 2011/0105454 A1 May 5, 2011

Related U.S. Application Data

(60) Provisional application No. 61/009,276, filed on Dec. 27, 2007.

(51) Int. Cl.
*A61K 31/496* (2006.01)
*A61K 31/444* (2006.01)
*C07D 401/04* (2006.01)
*C07D 401/14* (2006.01)
*C07D 209/34* (2006.01)

(52) U.S. Cl.
USPC ............... 514/253.09; 514/254.09; 514/318; 514/339; 544/364; 544/373; 546/194; 546/277.7

(58) Field of Classification Search
None
See application file for complete search history.

(56) References Cited

U.S. PATENT DOCUMENTS

| 5,594,023 A | 1/1997 | Wagnon et al. |
| 6,090,818 A | 7/2000 | Foulon et al. |
| 2003/0109545 A1 | 6/2003 | Serraqdeil-Le-Gal et al. |
| 2003/0114683 A1 | 6/2003 | Roux et al. |
| 2003/0139413 A1 | 7/2003 | Schoentjes et al. |
| 2003/0162767 A1 | 8/2003 | Roux et al. |
| 2004/0180878 A1 | 9/2004 | Di Malta et al. |
| 2009/0318406 A1 | 12/2009 | Geneste et al. |
| 2010/0273766 A1 | 10/2010 | Oost et al. |
| 2011/0077253 A1 | 3/2011 | Oost et al. |

FOREIGN PATENT DOCUMENTS

| CA | 2107348 A1 | 7/1993 |
| CA | 2593044 A1 | 7/2006 |
| WO | 93/15051 A1 | 8/1993 |
| WO | 95/18105 A1 | 7/1995 |
| WO | 98/25901 A1 | 6/1998 |
| WO | 01/55130 A2 | 8/2001 |
| WO | 01/55134 A2 | 8/2001 |
| WO | 01/64668 A2 | 9/2001 |
| WO | 01/98295 A1 | 12/2001 |
| WO | 03/008407 A2 | 1/2003 |
| WO | 2005/030755 A1 | 4/2005 |
| WO | 2006/072458 A2 | 7/2006 |
| WO | 2007/063123 A1 | 6/2007 |
| WO | 2008/025735 A1 | 3/2008 |
| WO | 2009/071687 A1 | 6/2009 |

OTHER PUBLICATIONS

Banker et al. "Modern Pharmaceutics", 3rd Ed. p. 596 (1996).*
Burger's Medicinal Chemistry, edited by Manfred E. Wolff, 5th Ed. Part 1, pp. 975-977 (1995).*
Opposition Brief for corresponding Costa Rican Patent Application No. 11584, dated Mar. 4, 2011, pp. 1-6. (In Spanish and the English translation).
Thibonnier, M., Exp. Opin. Invest. Drugs 1998, 7(5), 729-740.
Diaz, G.J., et al., Journal of Pharmacological and Toxicological Methods, 50 (2004), 187-199.
International Search Report for WO2009/083559, Apr. 2009.
Translation of Opposition from Ecuadorian Patent Application SP-10-10379 (2010).

* cited by examiner

*Primary Examiner* — Emily Bernhardt
(74) *Attorney, Agent, or Firm* — Lisa V. Mueller; Michael Best & Friedrich LLP

(57) ABSTRACT

The present invention relates to novel substituted oxindole derivatives of the formula (I), pharmaceutical agents containing said derivatives, and the use thereof for the treatment of vasopressin-dependent illnesses.

32 Claims, No Drawings

SUBSTITUTED OXINDOLE-DERIVATIVES AND THE USE THEREOF FOR THE TREATMENT OF VASOPRESSIN-DEPENDENT ILLNESSES

CROSS-REFERENCE TO RELATED APPLICATIONS

This is the U.S. national stage entry of International Patent Application No. PCT/EP2008/068254, filed on Dec. 23, 2008, which claims priority to U.S. Provisional Patent Application No. 61/009,276, filed on Dec. 27, 2007, the contents of all of which are hereby incorporated by reference.

The present invention relates to novel substituted oxindole derivatives, pharmaceutical compositions comprising them, and their use for the treatment of vasopressin-dependent disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3 and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740).

Novel substituted oxindoles having a phenylsulfonyl group in position 1 are described herein. 1-Phenylsulfonyl-1,3-dihydro-2H-indol-2-ones have previously been described as ligands of vasopressin receptors. WO 93/15051, WO 95/18105, WO 98/25901, WO 01/55130, WO 01/55134, WO 01/164668 and WO 01/98295 also describe derivatives having arylsulfonyl groups in position 1 of the oxindole structure. These compounds differ from the compounds of the invention essentially through the substituents in position 3.

Thus, WO 93/15051 and WO 98/25901 describe 1-phenylsulfonyl-1,3-dihydro-2H-indol-2-ones, in which the oxindole structure is substituted in position 3 by two alkyl radicals which may also together form a cycloalkyl radical (spiro linkage), as ligands of vasopressin receptors. As alternative, the spiro ring may comprise heteroatoms such as oxygen and nitrogen (optionally with substituents).

WO 95/18105 describes 1-phenylsulfonyl-1,3-dihydro-2H-indol-2-ones having a nitrogen atom in position 3 as ligands of vasopressin receptors. In addition, radicals selected from optionally substituted alkyl, cycloalkyl, phenyl or benzyl radicals are bonded in position 3.

WO 03/008407 describes 1-phenylsulfonyloxindoles in which pyridylpiperazines are linked via a urea, carbamate or 2-oxoethyl group to the oxindole in position 3.

Besides the binding affinity for the vasopressin V1b receptor, further properties may be advantageous for the treatment and/or prophylaxis of vasopressin-dependent disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;
2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;
3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity.
4.) the metabolic stability, for example determined from the half-lives, measured in vitro, in liver microsomes from various species (e.g. rat or human);
5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
6.) a suitable solubility in water (in mg/ml);
7.) suitable pharmacokinetics (time course of the concentration of the compound of the invention in plasma or in tissue, for example brain). The pharmacokinetics can be described by the following parameters: half-life (in h), volume of distribution (in $l \cdot kg^{-1}$), plasma clearance (in $l \cdot h^{-1} \cdot kg^{-1}$), AUC (area under the curve, area under the concentration-time curve, in $ng \cdot h \cdot l^{-1}$), oral bioavailability (the dose-normalized ratio of AUC after oral administration and AUC after intravenous administration), the so-called brain-plasma ratio (the ratio of AUC in brain tissue and AUC in plasma);
8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-dependent diseases. The compounds were intended to have a high activity and selectivity, especially a high affinity and selectivity vis-à-vis the vasopressin V1b receptor. In addition, the substance of the invention was intended to have one or more of the aforementioned advantages 1.) to 8.).

The object is achieved by compounds of the formula I (I)

[Chemical structure of formula I showing an indolinone core with substituents R⁵, R⁶, R⁷, R⁸ on one phenyl ring, X⁴ in that ring, X¹—A—X²—X³ linker to a nitrogen-containing ring with (R⁹)ₐ and N—R⁴ substituents, and an SO₂-linked phenyl ring with R¹, R², R³ substituents]

in which
X¹ is —O—, —O—CH₂—, —O—C(=O)—, —NR¹¹—, —NR¹¹—CH₂— or —NR¹¹—C(=O)—;
X² is a single bond, CO or CH₂;
X³ is N or CH;
X⁴ is N or CH;
A is phenylene or 6-membered hetarylene with 1 or 2 nitrogen atoms as ring members, where phenylene or hetarylene may be substituted by 1 or 2 radicals R¹⁰;
R¹ and R³ are independently of one another hydrogen, C₁-C₃-alkyl, C₁-C₃-fluoroalkyl, C₁-C₃-alkoxy, C₁-C₃-fluoroalkoxy, halogen or CN;
R² is hydrogen or methoxy;
where at least one of the radicals R¹, R² and R³ is hydrogen;
R⁴ is hydrogen or C₁-C₄-alkyl;
R⁵ is ethoxy, fluorinated ethoxy, fluoromethoxy, difluoromethoxy, trifluoromethoxy or isopropoxy;
R⁶ is hydrogen or methyl;
R⁷ is hydrogen, I, Br, Cl, F or CN;
R⁸ is hydrogen, I, Br, Cl, F or CN;
R⁹ is C₁-C₃-alkyl or C₁-C₃-fluoroalkyl;
R¹⁰ is C₁-C₃-alkyl, C₁-C₃-fluoroalkyl, C₁-C₃-alkoxy or C₁-C₃-fluoroalkoxy;
R¹¹ is hydrogen, C₁-C₄-alkyl, C₁-C₄-fluoroalkyl, C₁-C₄-alkoxy or C₁-C₄-fluoroalkoxy;
a is 0, 1 or 2; and
m and n are independently of one another 1 or 2;
and their pharmaceutically acceptable salts and prodrugs thereof.

Accordingly, the present invention relates to compounds of the formula I (also "compounds I" hereinafter) and the pharmaceutically acceptable salts of the compounds I and the prodrugs of the compounds I.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhäuser Verlag, vol. 10, pp. 224-285. These include for example hydrochloric acid, citric acid, tartaric acid, lactic acid, phosphoric acid, methanesulfonic acid, acetic acid, formic acid, maleic acid and fumaric acid.

The term "prodrugs" means compounds which are metabolized in vivo to the compounds I of the invention. Typical examples of prodrugs are described in C. G. Wermeth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example compounds I in which the outer nitrogen atom of the outer nitrogen-containing ring forms an amide/peptide linkage by this nitrogen atom being substituted by a C₁-C₄-alkylcarbonyl group, e.g. by acetyl, propionyl, n-propylcarbonyl, isopropylcarbonyl, n-butylcarbonyl or tert-butylcarbonyl (pivaloyl), by benzoyl, or by an amino acid residue linked via CO, e.g. glycine, alanine, serine, phenylalanine and the like linked via CO, in the position of the radical R⁴. Further suitable prodrugs are alkylcarbonyloxyalkyl carbamates in which the outer nitrogen atom of the outer nitrogen-containing ring has in the position of the radical R⁴ a group of the formula —C(=O)—O—CHRᵃ—O—C(=O)—Rᵇ in which Rᵃ and Rᵇ are independently of one another C₁-C₄-alkyl. Such carbamates are described for example in J. Alexander, R. Cargill, S. R. Michelson, H. Schwam, J. Medicinal Chem. 1988, 31(2), 318-322. These groups can then be eliminated under metabolic conditions and result in compounds I in which R⁴ is H.

C₁-C₃-Alkyl is in the context of the present invention a linear or branched alkyl radical having 1 to 3 carbon atoms, such as methyl, ethyl, n-propyl or isopropyl.

C₁-C₄-Alkyl is in the context of the present invention a linear or branched alkyl radical having 1 to 4 carbon atoms, such as methyl, ethyl, n-propyl, isopropyl, n-butyl, sec-butyl, isobutyl or tert-butyl.

C₁-C₃-Fluoroalkyl is in the context of the present invention a linear or branched alkyl radical having 1 to 3 carbon atoms as defined above, in which at least one hydrogen atom, e.g. 1, 2, 3, 4 or 5 hydrogen atoms, are replaced by fluorine atoms. Examples thereof are fluoromethyl, difluoromethyl, trifluoromethyl, 1- and 2-fluoroethyl, 1,1-, 1,2- and 2,2-difluoroethyl, 1,1,2-, 1,2,2 and 2,2,2-trifluoroethyl, 1,1,2,2-tetrafluoroethyl, 1,2,2,2-tetrafluoroethyl, pentafluoroethyl, 1-, 2- and 3-fluoroprop-1-yl, 1,1-, 1,2-, 1,3-, 2,2-, 2,3- and 3,3-difluoroprop-1-yl, 1,1,2-, 1,2,2-, 1,1,3-, 2,2,3-, 1,2,3- and 3,3,3-trifluoroprop-1-yl, 1- and 2-fluoroprop-2-yl, 1,1- and 1,3-difluoroprop-2-yl, 1,1,1-trifluoroprop-2-yl and the like.

C₁-C₄-Fluoroalkyl is in the context of the present invention a linear or branched alkyl radical having 1 to 4 carbon atoms as defined above, in which at least one hydrogen atom, e.g. 1, 2, 3, 4 or 5 hydrogen atoms, are replaced by fluorine atoms. Examples thereof, besides the radicals mentioned above for C₁-C₃-fluoroalkyl, are 1-, 2-, 3- and 4-fluoro-n-butyl, 1,1-, 2,2-, 3,3- and 4,4-difluoro-n-butyl, 4,4,4-trifluoro-n-butyl, 3-fluoro-2-(fluoromethyl)-1-propyl, 3,3-difluoro-2-(difluoromethyl)-1-propyl, 3,3,3-trifluoro-2-(trifluoromethyl)-1-propyl and the like.

C₁-C₃-Alkoxy is in the context of the present invention a linear or branched alkyl radical linked via an oxygen atom and having 1 to 3 carbon atoms. Examples are methoxy, ethoxy, n-propoxy and isopropoxy.

C₁-C₄-Alkoxy is in the context of the present invention a linear or branched alkyl radical linked via an oxygen atom and having 1 to 4 carbon atoms. Examples besides the radicals mentioned above for C₁-C₃-alkoxy are n-butoxy, sec-butoxy, isobutoxy and tert-butoxy.

C₁-C₃-Fluoroalkoxy is in the context of the present invention a linear or branched alkyl radical linked via an oxygen atom and having 1 to 3 carbon atoms as defined above, in which at least one hydrogen atom, e.g. 1, 2, 3, 4 or 5 hydrogen atoms, are replaced by fluorine atoms. Examples thereof are fluoromethoxy, difluoromethoxy, trifluoromethoxy, 1- and 2-fluoroethoxy, 1,1-, 1,2- and 2,2-difluoroethoxy, 1,1,2-, 1,2,2 and 2,2,2-trifluoroethoxy, 1,1,2,2-tetrafluoroethoxy, 1,2,2,2-tetrafluoroethoxy, pentafluoroethoxy, 1-, 2- and 3-fluoroprop-1-oxy, 1,1-, 1,2-, 1,3-, 2,2-, 2,3- and 3,3-difluoroprop-1-oxy, 1,1,2-, 1,2,2-, 1,1,3-, 2,2,3-, 1,2,3- and 3,3,3-trifluoroprop-1-oxy, 1- and 2-fluoroprop-2-oxy, 1,1- and 1,3-difluoroprop-2-oxy, 1,1,1-trifluoroprop-2-oxy and the like.

$C_1$-$C_4$-Fluoroalkoxy is in the context of the present invention a linear or branched alkyl radical linked via an oxygen atom and having 1 to 4 carbon atoms as defined above, in which at least one hydrogen atom, e.g. 1, 2, 3, 4 or 5 hydrogen atoms, are replaced by fluorine atoms. Examples thereof besides the radicals mentioned above for $C_1$-$C_3$-fluoroalkoxy are 1-, 2-, 3- and 4-fluoro-n-butoxy, 1,1-, 2,2-, 3,3- and 4,4-difluoro-n-butoxy, 4,4,4-trifluoro-n-butoxy, 3-fluoro-2-(fluoromethyl)-1-propoxy, 3,3-difluoro-2-(difluoromethyl)-1-propoxy, 3,3,3-trifluoro-2-(trifluoromethyl)-1-propoxy and the like.

Fluorinated ethoxy is in the context of the present invention ethoxy in which 1, 2, 3, 4 or 5 of the hydrogen atoms are replaced by fluorine atoms. Examples are 1-fluoroethoxy, 2-fluoroethoxy, 1,1-difluoroethoxy, 1,2-difluoroethoxy, 2,2-difluoroethoxy, 1,1,2-trifluoroethoxy, 1,2,2-trifluoroethoxy, 2,2,2-trifluoroethoxy, 1,1,2,2-tetrafluoroethoxy and 1,1,2,2,2-pentafluoroethoxy.

Halogen is in the context of the present invention fluorine, chlorine, bromine or iodine.

Phenylene is a divalent phenyl radical such as 1,2-phenylene, 1,3-phenylene and 1,4-phenylene.

6-Membered hetarylene having one or 2 nitrogen atoms as ring members is a divalent pyridyl radical (pyridylene) such as 2,3-pyridylene, 2,4-pyridylene, 2,5-pyridylene, 2,6-pyridylene, 3,4-pyridylene, 3,5-pyridylene, 3,6-pyridylene, 4,5-pyridylene, 4,6-pyridylene or 5,6-pyridylene; is a divalent pyrimidyl radical (pyrimidylene) such as 2,3-pyrimidylene, 2,4-pyrimidylene, 4,2-pyrimidylene, 4,5-pyrimidylene, 4,6-pyrimidylene or 5,2-pyrimidylene; is a divalent pyrazine radical (pyrazinylene) such as 2,3-pyrazinylene, 2,5-pyrazinylene or 2,6-pyrazinylene; or is a divalent pyridazine radical (pyridazinylene) such as 3,4-pyridazinylene, 3,5-pyridazinylene, 3,6-pyridazinylene or 4,5-pyridazinylene.

The compounds of the invention of the formula I, their pharmacologically acceptable salts and their prodrugs may also be present in the form of solvates or hydrates. Solvates mean in the context of the present invention crystalline forms of the compounds I or of their pharmaceutically acceptable salts or prodrugs thereof which comprise solvent molecules incorporated in the crystal lattice. The solvent molecules are preferably incorporated in stoichiometric ratios. Hydrates are a specific form of solvates; the solvent in this case is water.

The statements made hereinafter concerning suitable and preferred features of the invention, especially concerning the variables $R^1$, $R^2$, $R^3$, $R^4$, $R^5$, $R^6$, $R^7$, $R^8$, $R^9$, $R^{10}$, $R^{11}$, $X^1$, $X^2$, $X^3$, $X^4$, A, a, m and n in the compound I, concerning the variables $R^1$, $R^2$, $R^3$, $R^5$, $R^6$, $R^7$, $R^8$, $R^{12}$, $X^1$, $X^4$ and A in the compound XVIII, but also concerning the features of the process of the invention and of the use according to the invention apply both taken on their own and preferably in any possible combination with one another.

The compounds I are preferably provided in the form of the free base (i.e. according to structural formula I) or in the form of their acid addition salts.

At least one of the radicals $R^1$, $R^2$, $R^3$ in compounds I is hydrogen. It is preferred for at least $R^2$ to be hydrogen. It is particularly preferred in this connection for $R^1$ or $R^3$ or $R^1$ and $R^3$ to be different from hydrogen.

$C_1$-$C_3$-Alkoxy in the definition of $R^1$ and $R^3$ is preferably ethoxy or methoxy and is specifically methoxy. $C_1$-$C_3$-Fluoroalkoxy is preferably $C_1$-$C_2$-fluoroalkoxy, i.e. is fluoromethoxy, difluoromethoxy, trifluoromethoxy, 1- and 2-fluoroethoxy, 1,1-, 1,2- and 2,2-difluoroethoxy, 1,1,2-, 1,2,2 and 2,2,2-trifluoroethoxy, 1,1,2,2-tetrafluoroethoxy, 1,2,2,2-tetrafluoroethoxy or pentafluoroethoxy, is preferably fluoromethoxy, difluoromethoxy, trifluoromethoxy, 2,2-difluoroethoxy or 2,2,2-trifluoroethoxy, and is specifically trifluoromethoxy, 2,2-difluoroethoxy or 2,2,2-trifluoroethoxy.

In a preferred embodiment, $R^1$ and $R^3$ are independently of one another hydrogen, CN, $C_1$-$C_3$-alkoxy or $C_1$-$C_3$-fluoroalkoxy. In this connection, $C_1$-$C_3$-alkoxy in the definition of the radicals $R^1$ and $R^3$ is preferably ethoxy or methoxy and is specifically methoxy.

$C_1$-$C_3$-Fluoroalkoxy is preferably $C_1$-$C_2$-fluoroalkoxy, i.e. is fluoromethoxy, difluoromethoxy, trifluoromethoxy, 1- and 2-fluoroethoxy, 1,1-, 1,2- and 2,2-difluoroethoxy, 1,1,2-, 1,2,2 and 2,2,2-trifluoroethoxy, 1,1,2,2-tetrafluoroethoxy, 1,2,2,2-tetrafluoroethoxy or pentafluoroethoxy, is preferably fluoromethoxy, difluoromethoxy, trifluoromethoxy, 2,2-difluoroethoxy or 2,2,2-trifluoroethoxy, and is specifically trifluoromethoxy, 2,2-difluoroethoxy or 2,2,2-trifluoroethoxy.

In a particularly preferred embodiment, $R^1$ is hydrogen, methoxy, ethoxy, fluoromethoxy, difluoromethoxy or trifluoromethoxy, is more preferably hydrogen, methoxy or trifluoromethoxy and is in particular hydrogen or methoxy.

In a particularly preferred embodiment, $R^3$ is hydrogen, $C_1$-$C_3$-alkoxy or $C_1$-$C_3$-fluoroalkoxy, is more preferably hydrogen, methoxy, ethoxy, fluoromethoxy, difluoromethoxy or trifluoromethoxy, is even more preferably hydrogen, methoxy or trifluoromethoxy, is in particular hydrogen or methoxy and is specifically methoxy.

In a particularly preferred embodiment, at least one of the radicals $R^1$ and $R^3$ is methoxy.

In a preferred embodiment, $R^2$ is hydrogen. Alternatively, $R^2$ is preferably methoxy and $R^1$ and $R^3$ are simultaneously hydrogen. However, $R^2$ is particularly preferably hydrogen.

In a specific embodiment, $R^1$ and $R^3$ are methoxy and $R^2$ is hydrogen; or one of the radicals $R^1$ and $R^3$ is methoxy and the other is hydrogen, and $R^2$ is hydrogen.

In a preferred embodiment, $R^4$ is hydrogen, methyl, ethyl, n-propyl or isopropyl, is particularly preferably hydrogen, methyl or ethyl, and is in particular hydrogen or methyl.

In a preferred embodiment, $R^5$ is ethoxy or fluorinated ethoxy, is particularly preferably ethoxy, 2,2-difluoroethoxy or 2,2,2-trifluoroethoxy and is in particular ethoxy.

In an preferred embodiment, $R^6$ is H.

In a particularly preferred embodiment, $R^5$ is ethoxy and $R^6$ is H. In this case, $X^4$ is N or CH and is preferably N.

In an alternatively particularly preferred embodiment, $R^5$ is ethoxy and $R^6$ is methyl. In this case, $X^4$ is preferably N.

In an alternatively particularly preferred embodiment, $R^5$ is isopropoxy and $R^6$ is H. In this case, $X^4$ is preferably N.

In an alternatively particularly preferred embodiment, $R^5$ is fluorinated ethoxy, is preferably 2,2-difluoroethoxy or 2,2,2-trifluoroethoxy and is particularly preferably 2,2-difluoroethoxy, and $R^6$ is H. At the same time in this case, $X^4$ is preferably CH.

$X^4$ is particularly preferably N.

In particular, $R^5$ is ethoxy and $R^6$ is H. In this case, $X^4$ is N or CH and is preferably N.

In a preferred embodiment, $R^7$ and $R^8$ are not simultaneously CN.

In a preferred embodiment, $R^7$ and $R^8$ are not simultaneously H.

$R^7$ is preferably F, Cl, I or CN, is particularly preferably I, Cl or CN and is in particular CN.

$R^8$ is preferably H or F.

In particular, $R^7$ is CN and $R^8$ is simultaneously H or F, or $R^7$ is I and $R^8$ is simultaneously H or F, is specifically H, or $R^7$ is Cl and $R^8$ is simultaneously H or F, is specifically H.

In a preferred embodiment, $R^9$ is methyl or ethyl.

a is preferably 0 or 1 and is in particular 0.

In a preferred embodiment, $R^{10}$ is methyl or methoxy.

In a preferred embodiment, $R^{11}$ is hydrogen, $C_1$-$C_4$-alkyl or $C_1$-$C_4$-alkoxy, is particularly preferably hydrogen, methyl or methoxy and is in particular hydrogen.

In a preferred embodiment, $X^1$ is —O—$CH_2$—, —O—C(=O)—, —$NR^{11}$—, —$NR^{11}$—$CH_2$— or —$NR^{11}$—C(=O)—.

$X^1$ is particularly preferably —O—C(=O)—, —$NR^{11}$—, —$NR^{11}$—$CH_2$— or —$NR^{11}$—C(=O)—. $X^1$ is more preferably —$NR^{11}$— or —$NR^{11}$—$CH_2$— and is in particular —$NR^{11}$—$CH_2$—. Preferably, in the case of these preferred meanings of $X^1$, $R^{11}$ has one of the above-given preferred meanings and is in particular H.

In a preferred embodiment, $X^2$ is a single bond.

In a preferred embodiment, $X^3$ is N. It is particularly preferred in this case if m and n are both 2. Accordingly, the ring containing $X^3$ as ring member is particularly preferably a piperazin-1-yl ring.

In an alternatively preferred embodiment, $X^3$ is CH. It is particularly preferred in this case if m and n are both 2. Accordingly, the ring containing $X^3$ as ring member is particularly preferably a piperidin-4-yl ring.

In an alternatively preferred embodiment, $X^3$ is CH. It is particularly preferred in this case if m and n are both 1. Accordingly, the ring containing $X^3$ as ring member is particularly preferably an azetidin-3-yl ring.

In an alternatively preferred embodiment, $X^3$ is CH. It is particularly preferred in this case if m is 1 and n is 2. Accordingly, the ring containing $X^3$ as ring member is particularly preferably a pyrrolidin-3-yl ring.

However, it is particularly preferred for $X^3$ to be N and m and n both to be 2 or for $X^3$ to be CH and m and n both to be 1. In particular $X^3$ is N and m and n are both 2.

In a preferred embodiment, A is phenylene, e.g. 1,2-, 1,3- or 1,4-phenylene. In this case, A is particularly preferably 1,3- or 1,4-phenylene and is in particular 1,4-phenylene.

In an alternatively preferred embodiment, A is pyridylene or pyrimidylene and is particularly preferably pyridylene. In this case, A is particularly preferably 3,5- or 3,6-pyridylene and is in particular 3,6-pyridylene.

However, A is particularly preferably phenylene, e.g. is 1,2-, 1,3- or 1,4-phenylene, is more preferably 1,3- or 1,4-phenylene and is in particular 1,4-phenylene.

A is preferably not substituted by $R^{10}$.

The invention preferably relates to compounds of the formula I in which
$R^1$ is H or methoxy;
$R^2$ is H;
$R^3$ is methoxy;
$R^4$ is H, methyl or ethyl;
$R^5$ is ethoxy;
$R^6$ is H;
$R^7$ is CN;
$R^8$ is H or F;
$X^1$ is —NH— or —$NHCH_2$—;
$X^2$ is a single bond;
$X^3$ is N;
$X^4$ is N;
A is 1,4-phenylene;
a is 0; and
m and n are 2;
and the pharmaceutically salts and prodrugs thereof.

The invention particularly preferably relates moreover, to compounds of the formula I in which
$R^1$ is H or methoxy;
$R^2$ is H;
$R^3$ is methoxy;
$R^4$ is H or methyl;
$R^5$ is ethoxy;
$R^6$ is H;
$R^7$ is CN;
$R^8$ is H or F;
$X^1$ is —$NHCH_2$—;
$X^2$ is a single bond;
$X^3$ is N;
$X^4$ is N;
A is 1,4-phenylene;
a is 0; and
m and n are 2;
and the pharmaceutically acceptable salts and prodrugs thereof.

The invention preferably relates to compounds of the formula I in which
$R^1$ is H or methoxy;
$R^2$ is H;
$R^3$ is methoxy;
$R^4$ is H, methyl or ethyl;
$R^5$ is ethoxy;
$R^6$ is H;
$R^7$ is I;
$R^8$ is H;
$X^1$ is —NH— or —$NHCH_2$—;
$X^2$ is a single bond;
$X^3$ is N;
$X^4$ is N;
A is 1,4-phenylene;
a is 0; and
m and n are 2;
and the pharmaceutically acceptable salts and prodrugs thereof.

The invention particularly preferably relates moreover to compounds of the formula I in which
$R^1$ is H or methoxy;
$R^2$ is H;
$R^3$ is methoxy;
$R^4$ is H or methyl;
$R^5$ is ethoxy;
$R^6$ is H;
$R^7$ is I;
$R^8$ is H;
$X^1$ is —$NHCH_2$—;
$X^2$ is a single bond;
$X^3$ is N;
$X^4$ is N;
A is 1,4-phenylene;
a is 0; and
m and n are 2;
and the pharmaceutically acceptable salts and prodrugs thereof.

Examples of preferred embodiments of the present invention are compounds of the formulae I.1 to I.56 and the pharmaceutically acceptable salts and prodrugs thereof, in which the radicals $X^1$, $R^1$, $R^2$, $R^3$, $R^4$, $R^7$ and $R^8$ have the general or particularly preferred meanings indicated above. The radicals $R^1$, $R^2$, $R^3$, $R^4$, $R^7$ and $R^8$ particularly preferably have the meanings indicated in table A.
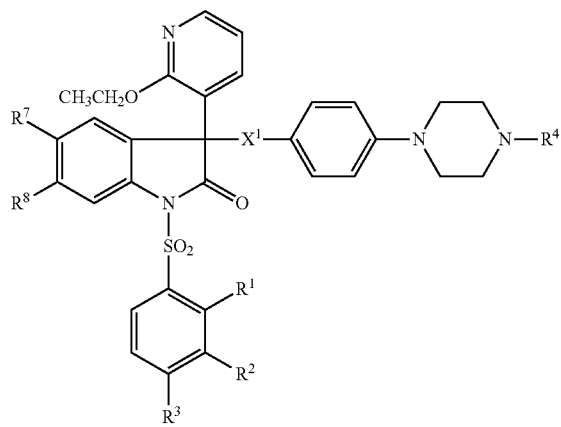
(I.1)
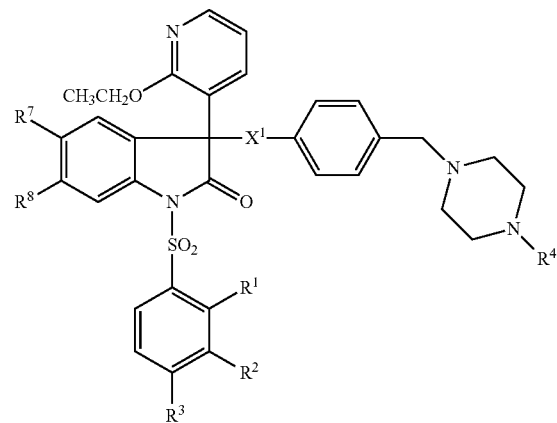
(I.4)
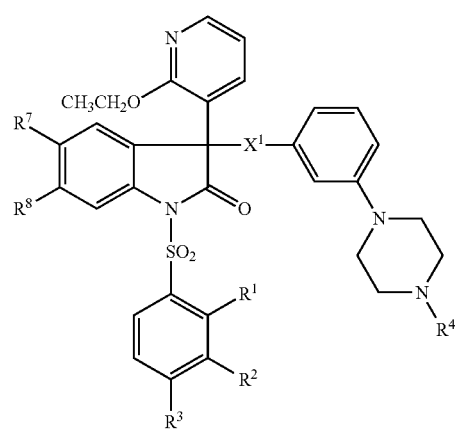
(I.2)
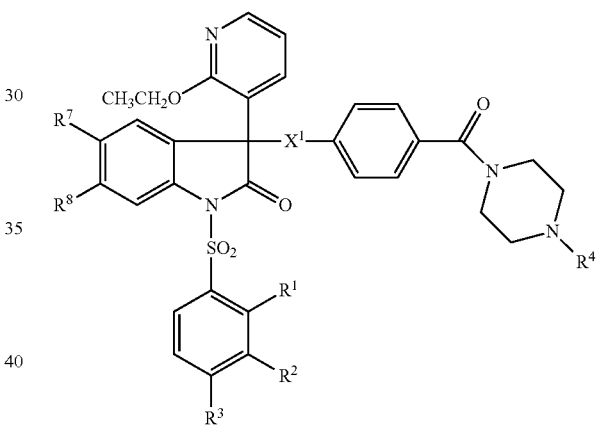
(I.5)
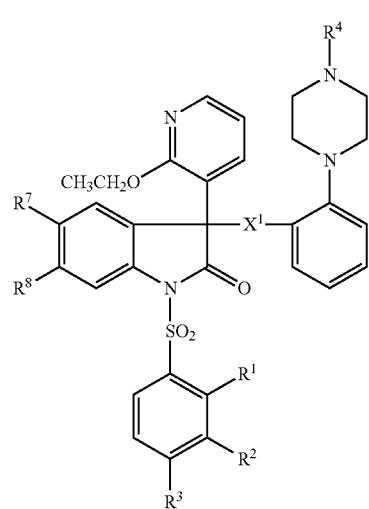
(I.3)
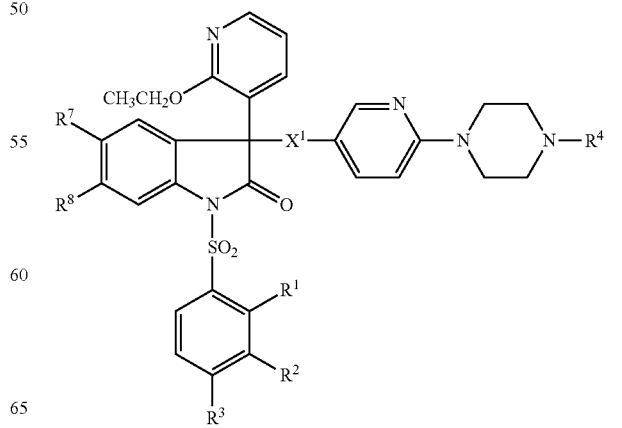
(I.6)

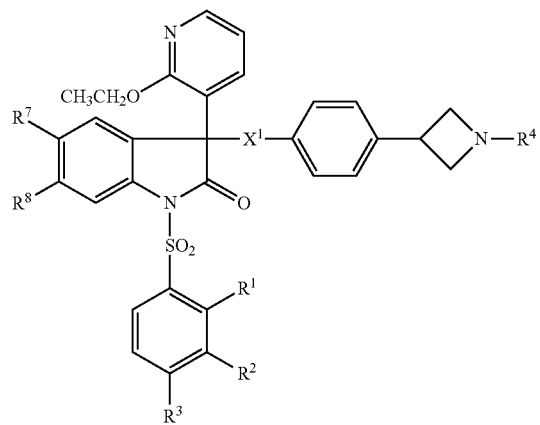
(I.7)
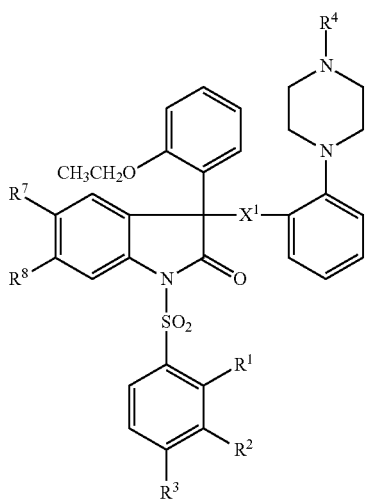
(I.10)
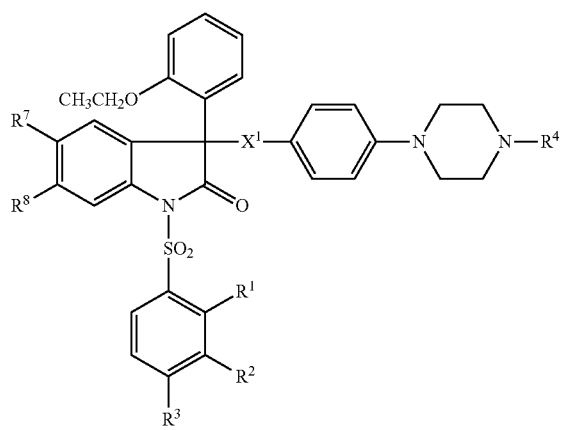
(I.8)
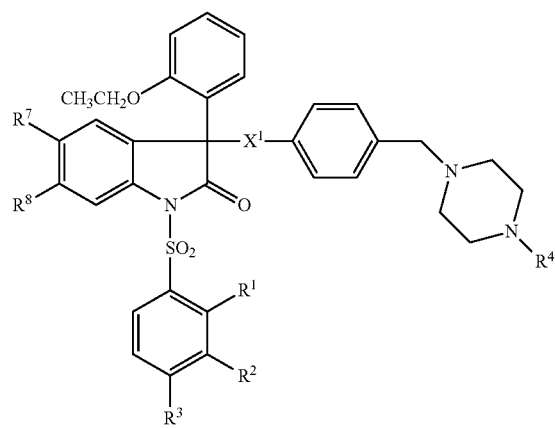
(I.11)
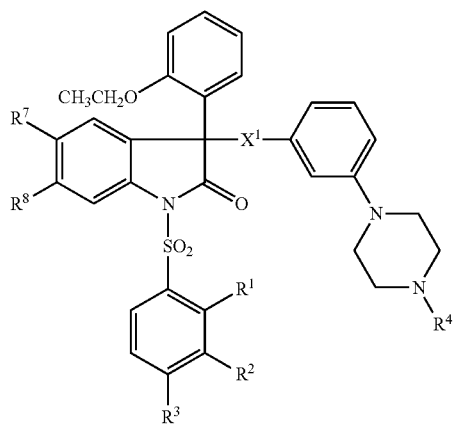
(I.9)
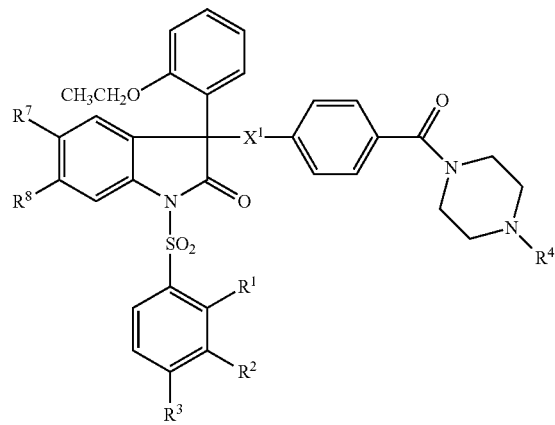
(I.12)

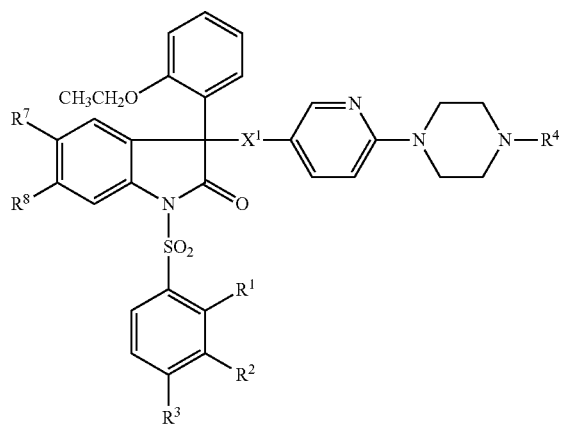
(I.13)
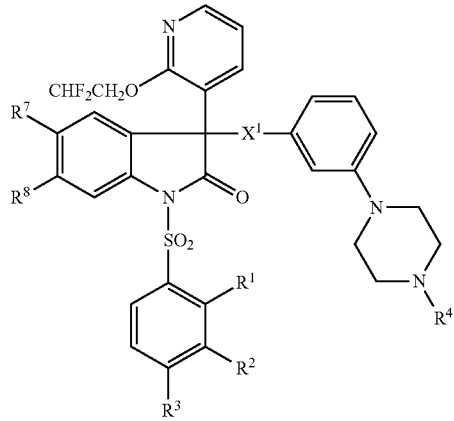
(I.16)
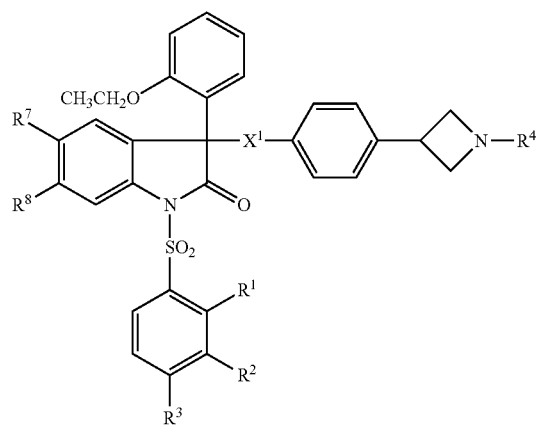
(I.14)
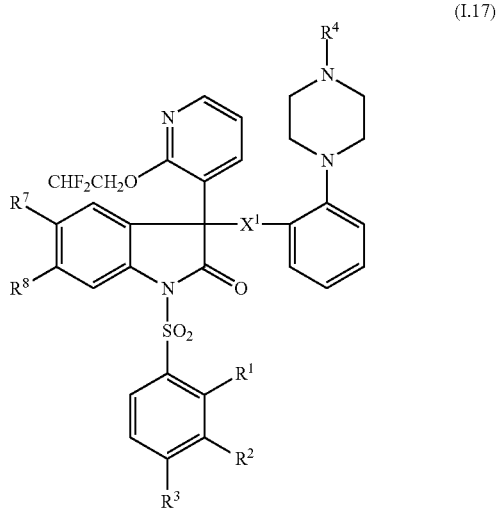
(I.17)
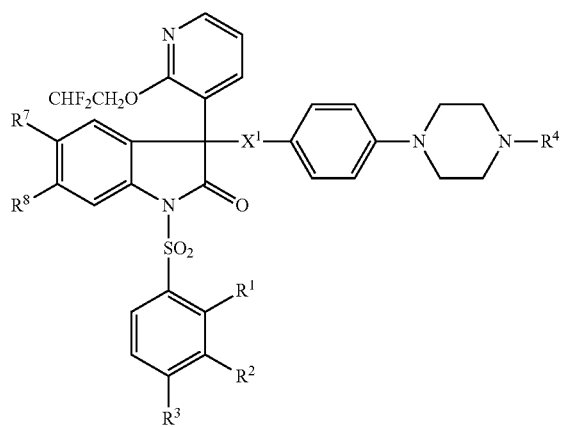
(I.15)
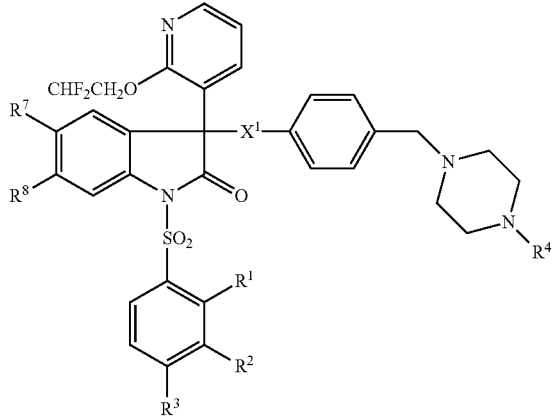
(I.18)

(I.19)
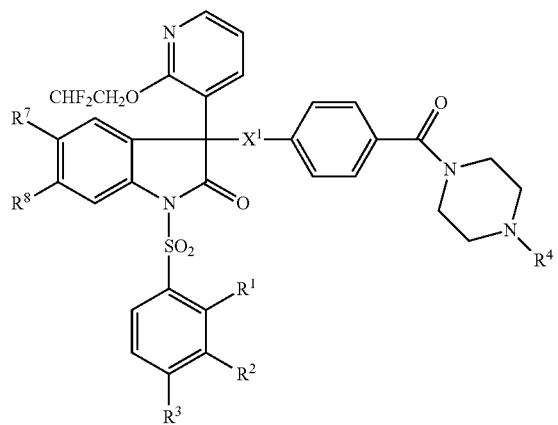
(I.22)
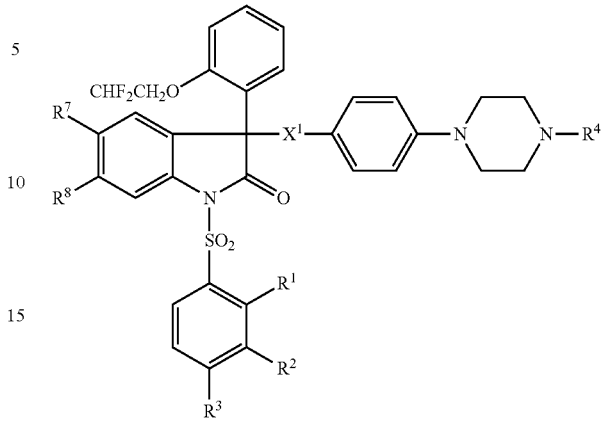
(I.20)
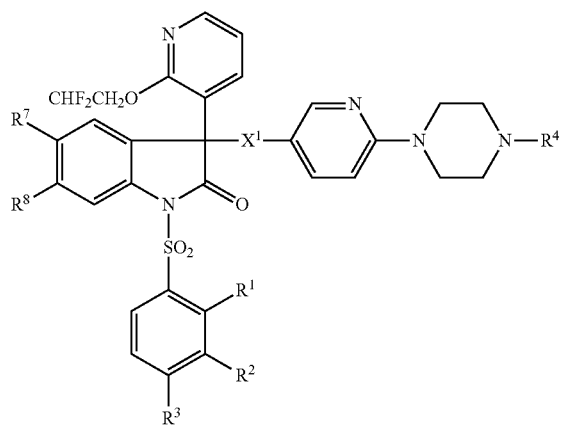
(I.23)
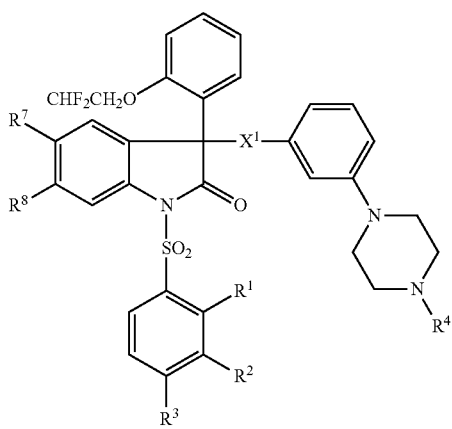
(I.21)
(I.24)
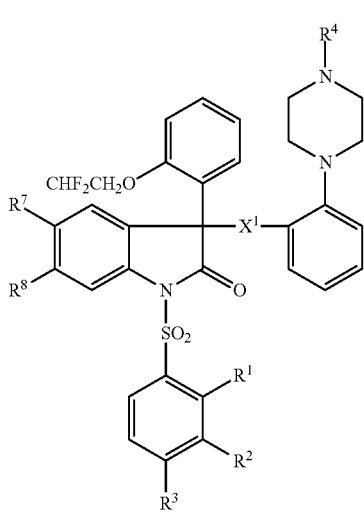

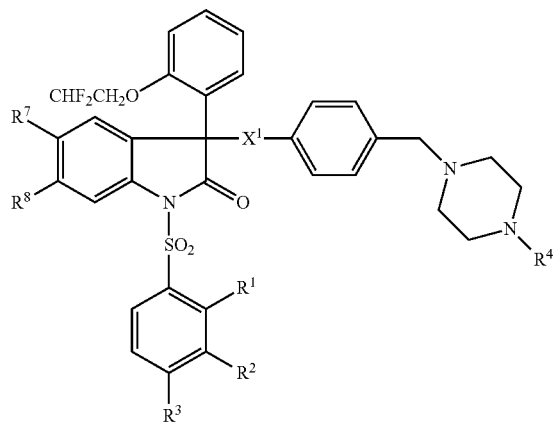
(I.25)
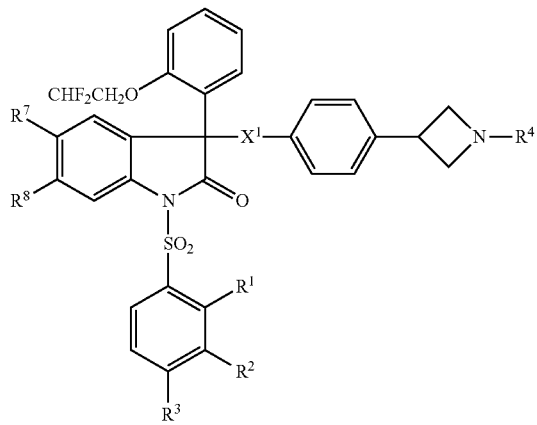
(I.28)
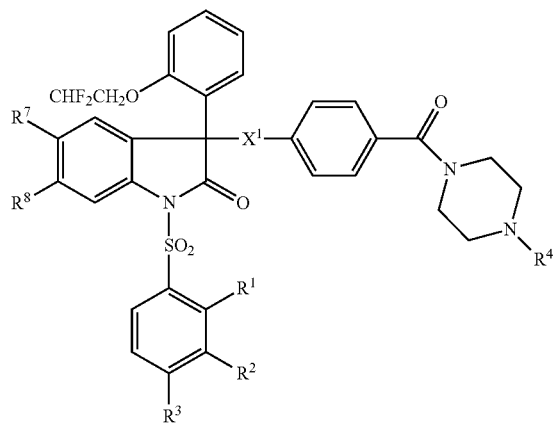
(I.26)
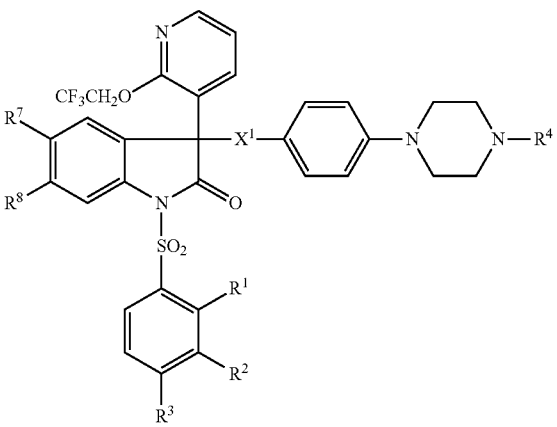
(I.29)
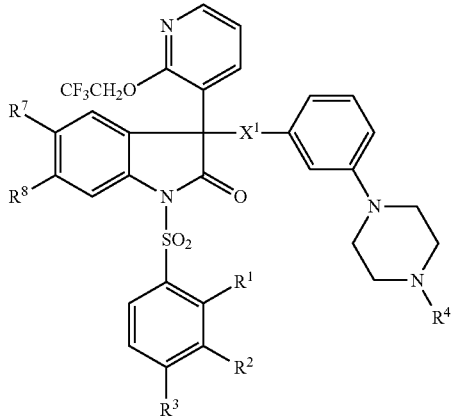
(I.27)
(I.30)

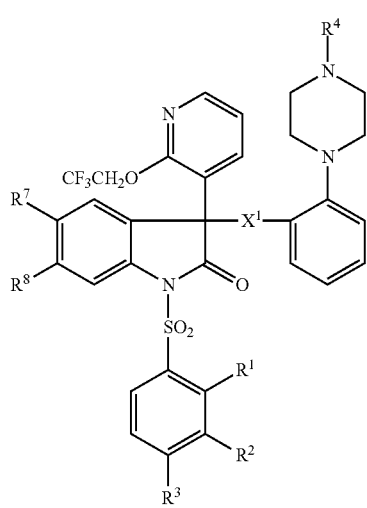
(I.31)
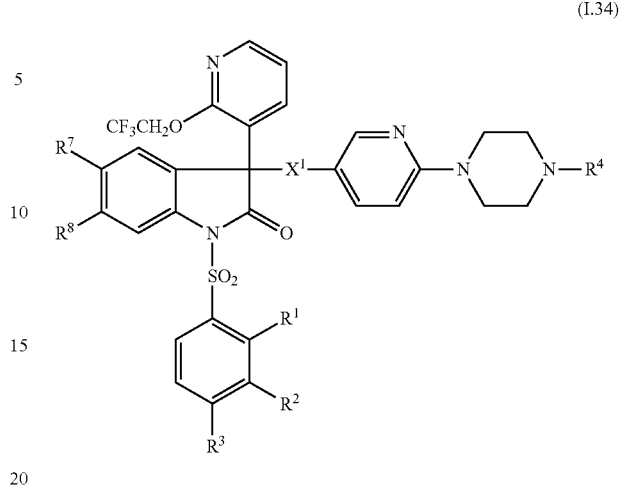
(I.34)
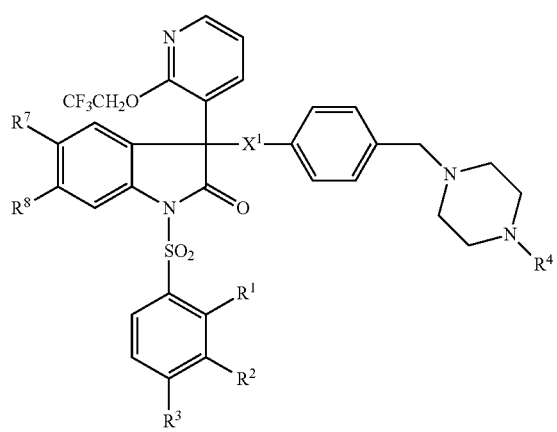
(I.32)
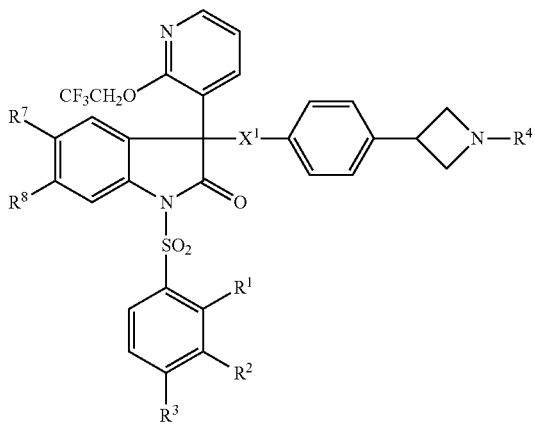
(I.35)
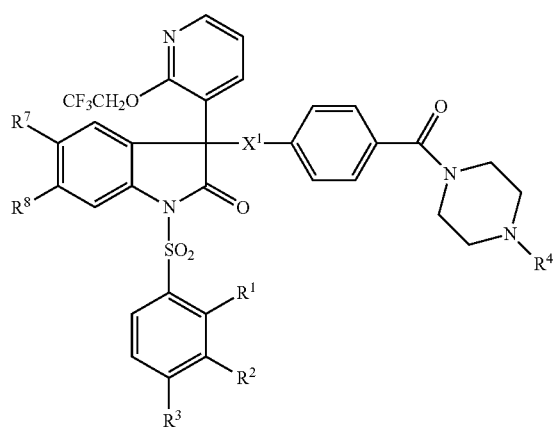
(I.33)
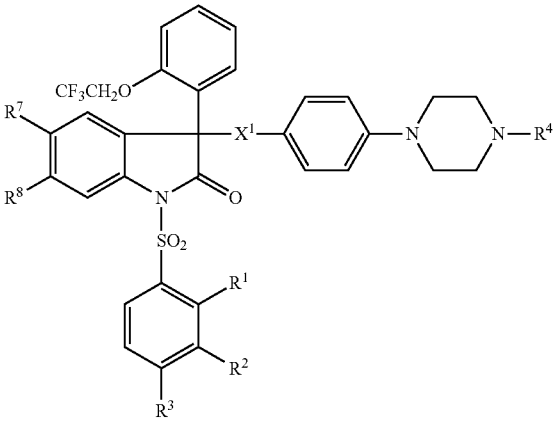
(I.36)

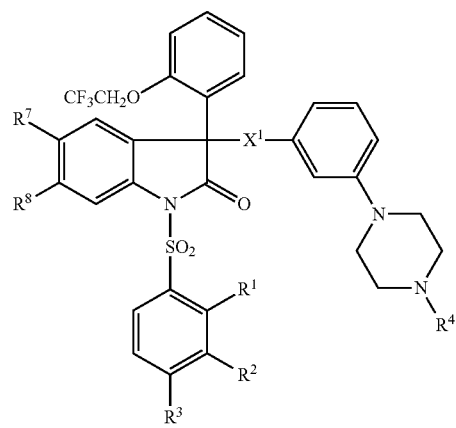
(I.37)
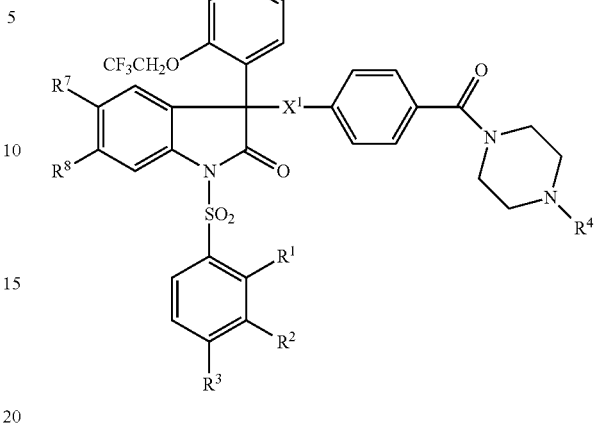
(I.40)
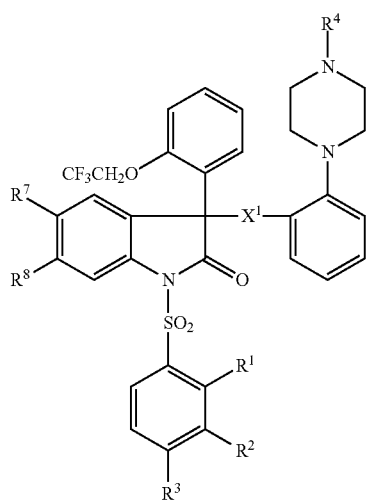
(I.38)
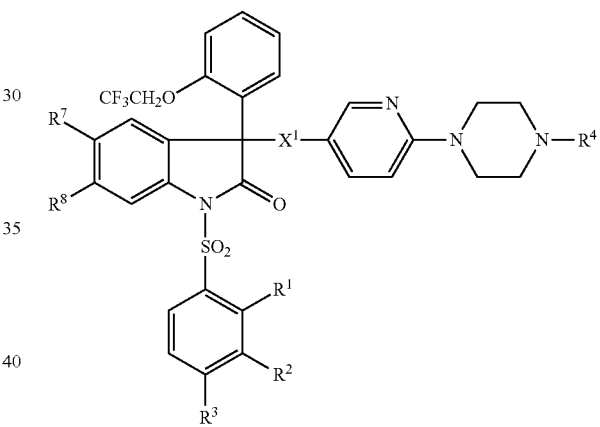
(I.41)
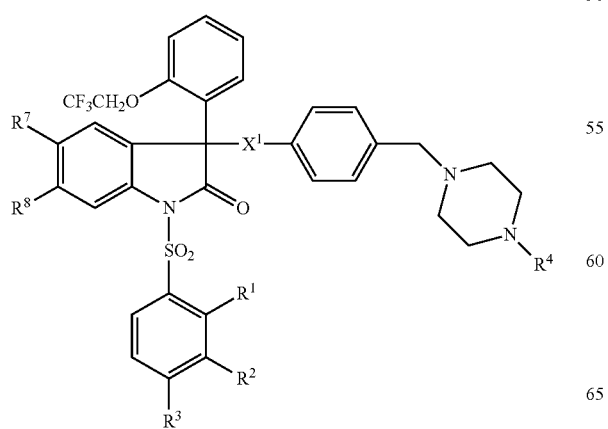
(I.39)
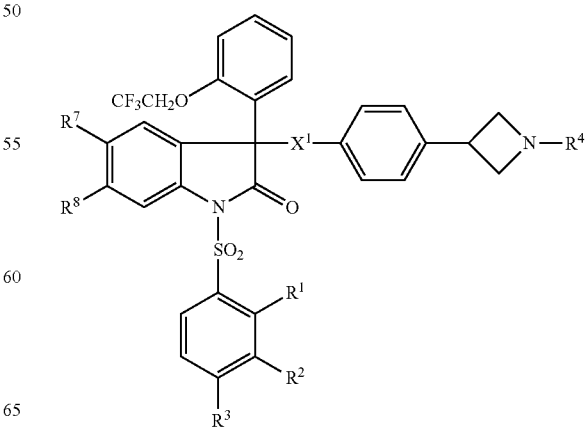
(I.42)

-continued
(I.43)
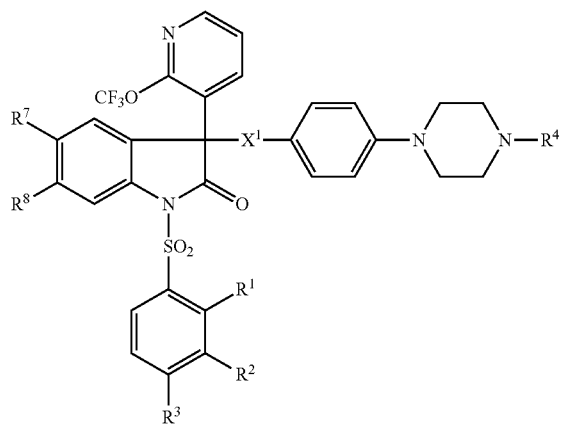
(I.46)
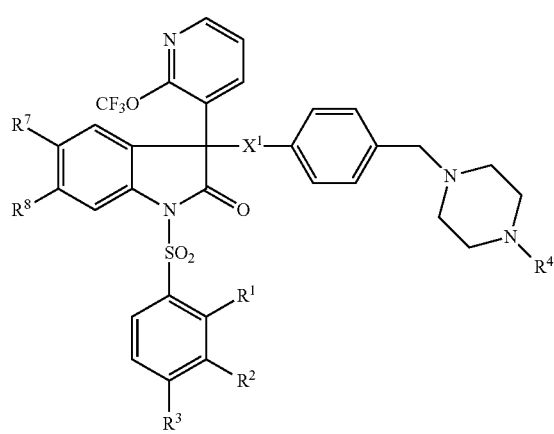
(I.44)
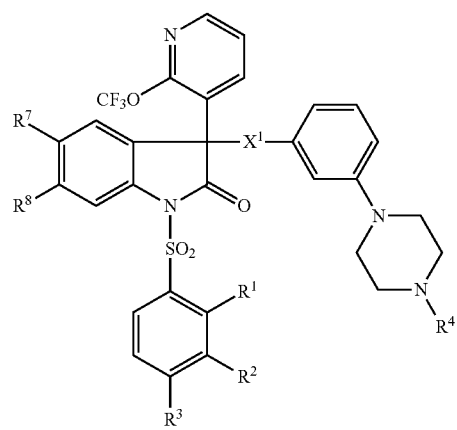
(I.47)
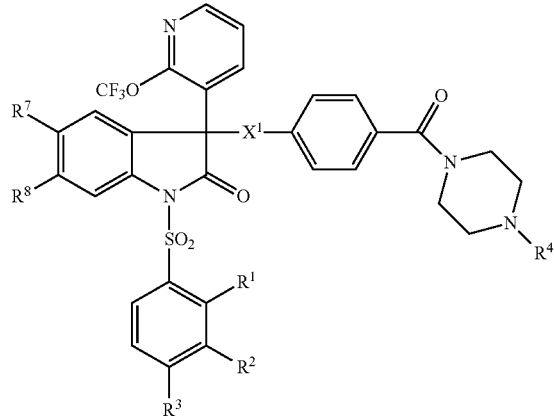
(I.45)
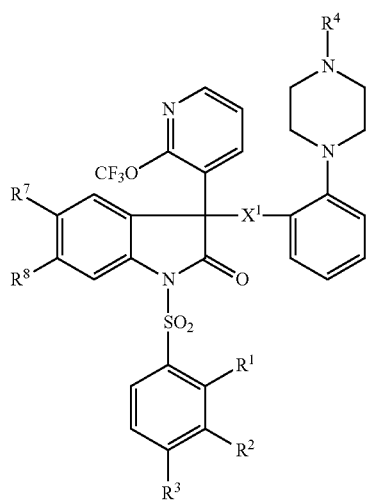
(I.48)
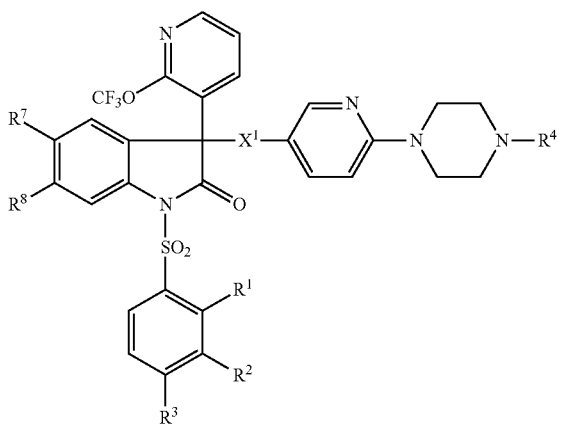

(I.49)
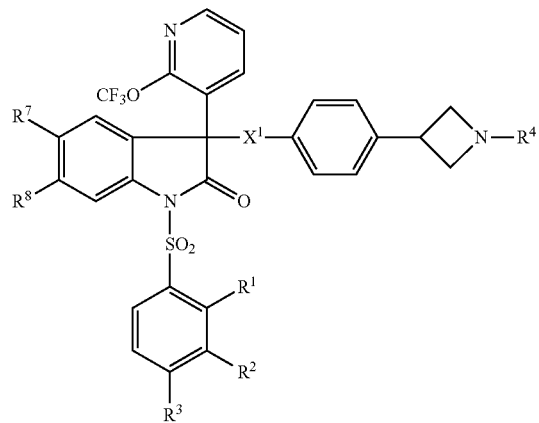
(I.50)
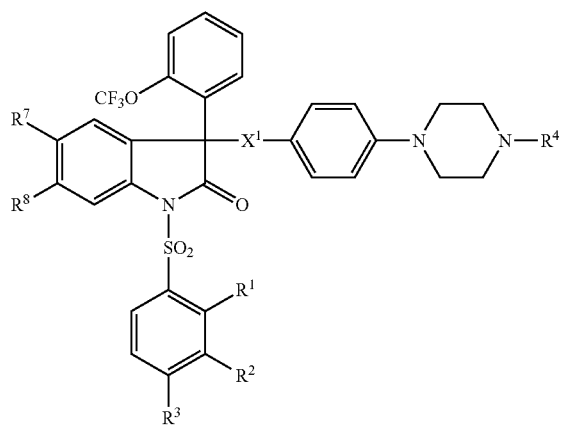
(I.51)
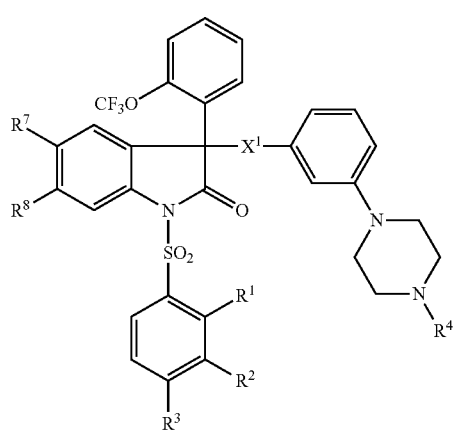
(I.52)
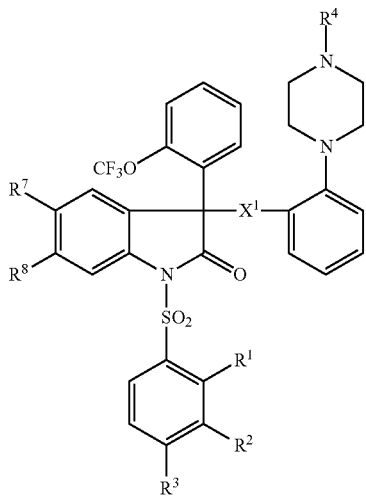
(I.53)
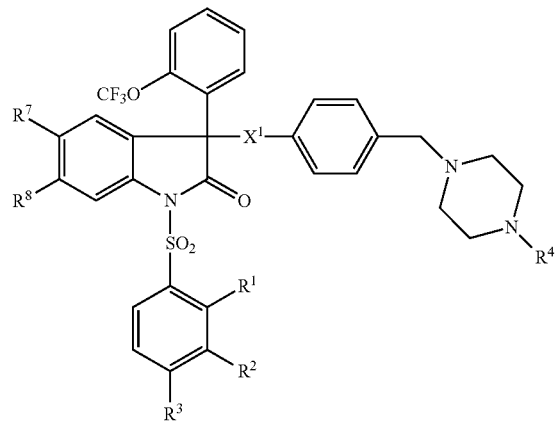
(I.54)
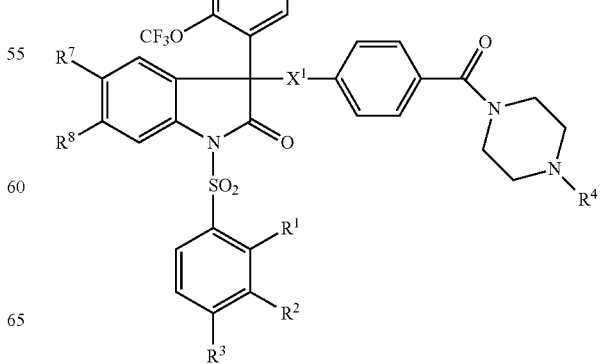

-continued

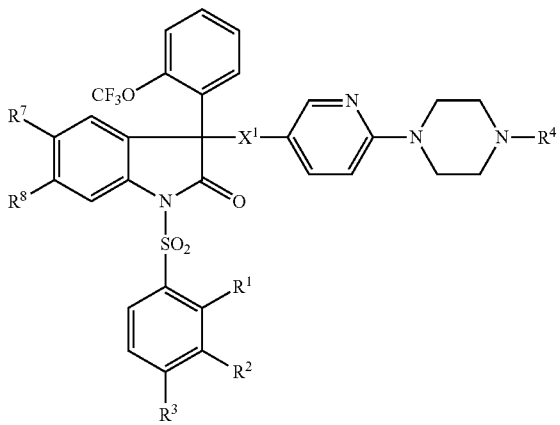
(I.55)

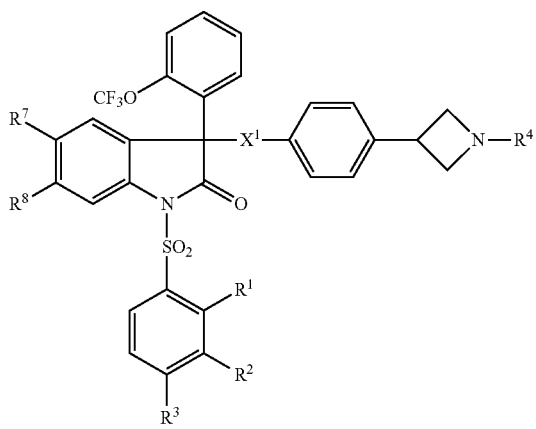
(I.56)

Preferred compounds of the formulae I.1 to I.56 are listed in tables 1 to 336 below:

Table 1
  Compounds of the formula I.1 in which $X^1$ is —NH$_2$—CH$_2$—, and the combination of $R^1$, $R^2$, $R^3$, $R^4$, $R^7$ and $R^8$ corresponds in each case to one line in table A
Table 2
  Compounds of the formula I.1 in which $X^1$ is —NH—, and the combination of $R^1$, $R^2$, $R^3$, $R^4$, $R^7$ and $R^8$ corresponds in each case to one line in table A
Table 3
  Compounds of the formula I.1 in which $X^1$ is —NH—C(=O)—, and the combination of $R^1$, $R^2$, $R^3$, $R^4$, $R^7$ and $R^8$ corresponds in each case to one line in table A.
Table 4
  Compounds of the formula I.1 in which $X^1$ is —O—CH$_2$—, and the combination of $R^1$, $R^2$, $R^3$, $R^4$, $R^7$ and $R^8$ corresponds in each case to one line in table A
Table 5
  Compounds of the formula I.1 in which $X^1$ is —O—, and the combination of $R^1$, $R^2$, $R^3$, $R^4$, $R^7$ and $R^8$ corresponds in each case to one line in table A
Table 6
  Compounds of the formula I.1 in which $X^1$ is —O—C(=O)—, and the combination of $R^1$, $R^2$, $R^3$, $R^4$, $R^7$ and $R^8$ corresponds in each case to one line in table A
Tables 7 to 12
  Compounds of the formula I.2 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 13 to 18
  Compounds of the formula I.3 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 19 to 24
  Compounds of the formula I.4 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 25 to 30
  Compounds of the formula I.5 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 31 to 36
  Compounds of the formula I.6 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 37 to 42
  Compounds of the formula I.7 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 43 to 48
  Compounds of the formula I.8 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 49 to 54
  Compounds of the formula I.9 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 55 to 60
  Compounds of the formula I.10 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 61 to 66
  Compounds of the formula I.11 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 67 to 72
  Compounds of the formula I.12 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 73 to 78
  Compounds of the formula I.13 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 79 to 84
  Compounds of the formula I.14 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 85 to 90
  Compounds of the formula I.15 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 91 to 96
  Compounds of the formula I.16 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 97 to 102
  Compounds of the formula I.17 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 103 to 108
  Compounds of the formula I.18 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 109 to 114
  Compounds of the formula I.19 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 115 to 120
  Compounds of the formula I.20 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 121 to 126
  Compounds of the formula I.21 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 127 to 132
  Compounds of the formula I.22 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 133 to 138
  Compounds of the formula I.23 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 139 to 144
  Compounds of the formula I.24 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 145 to 150
  Compounds of the formula I.25 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 151 to 156
  Compounds of the formula I.26 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 157 to 162
  Compounds of the formula I.27 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 163 to 168
  Compounds of the formula I.28 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 169 to 174
  Compounds of the formula I.29 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 175 to 180
  Compounds of the formula I.30 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 181 to 186
  Compounds of the formula I.31 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 187 to 192
  Compounds of the formula I.32 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 193 to 198
  Compounds of the formula I.33 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 199 to 204
  Compounds of the formula I.34 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 205 to 210
  Compounds of the formula I.35 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 211 to 216
  Compounds of the formula I.36 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 217 to 222
  Compounds of the formula I.37 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 223 to 228
  Compounds of the formula I.38 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 229 to 234
  Compounds of the formula I.39 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 235 to 240
  Compounds of the formula I.40 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 241 to 246
  Compounds of the formula I.41 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A
Tables 247 to 252
  Compounds of the formula I.42 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 253 to 258
Compounds of the formula I.43 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 259 to 264
Compounds of the formula I.44 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 265 to 270
Compounds of the formula I.45 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 271 to 276
Compounds of the formula I.46 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 277 to 282
Compounds of the formula I.47 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 283 to 288
Compounds of the formula I.48 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 289 to 294
Compounds of the formula I.49 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 295 to 300
Compounds of the formula I.50 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 301 to 306
Compounds of the formula I.51 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 307 to 312
Compounds of the formula I.52 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 313 to 318
Compounds of the formula I.53 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 319 to 324
Compounds of the formula I.54 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 325 to 330
Compounds of the formula I.55 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A Tables 331 to 336
Compounds of the formula I.56 in which $X^1$ has in each case one of the meanings indicated in tables 1, 2, 3, 4, 5 or 6, and the combination of $R^1$, $R^2$, $R^3$, $R^4$, $R^7$ and $R^8$ corresponds in each case to one line in table A

TABLE A

| Example No. | $R^1$ | $R^2$ | $R^3$ | $R^4$ | $R^7$ | $R^8$ |
|---|---|---|---|---|---|---|
| A-1. | H | H | H | H | CN | H |
| A-2. | Methoxy | H | H | H | CN | H |
| A-3. | Ethoxy | H | H | H | CN | H |
| A-4. | $OCF_3$ | H | H | H | CN | H |
| A-5. | H | H | Methoxy | H | CN | H |
| A-6. | Methoxy | H | Methoxy | H | CN | H |
| A-7. | Ethoxy | H | Methoxy | H | CN | H |
| A-8. | $OCF_3$ | H | Methoxy | H | CN | H |
| A-9. | H | H | Ethoxy | H | CN | H |
| A-10. | Methoxy | H | Ethoxy | H | CN | H |
| A-11. | Ethoxy | H | Ethoxy | H | CN | H |
| A-12. | $OCF_3$ | H | Ethoxy | H | CN | H |
| A-13. | H | H | $OCH_2F$ | H | CN | H |
| A-14. | H | H | $OCHF_2$ | H | CN | H |
| A-15. | H | H | $OCF_3$ | H | CN | H |
| A-16. | H | H | $OCH_2CH_2F$ | H | CN | H |
| A-17. | H | H | $OCH_2CHF_2$ | H | CN | H |
| A-18. | H | H | $OCH_2CF_3$ | H | CN | H |
| A-19. | H | H | Cl | H | CN | H |
| A-20. | H | H | CN | H | CN | H |
| A-21. | H | Methoxy | H | H | CN | H |
| A-22. | H | H | H | Methyl | CN | H |
| A-23. | Methoxy | H | H | Methyl | CN | H |
| A-24. | Ethoxy | H | H | Methyl | CN | H |
| A-25. | $OCF_3$ | H | H | Methyl | CN | H |
| A-26. | H | H | Methoxy | Methyl | CN | H |
| A-27. | Methoxy | H | Methoxy | Methyl | CN | H |
| A-28. | Ethoxy | H | Methoxy | Methyl | CN | H |
| A-29. | $OCF_3$ | H | Methoxy | Methyl | CN | H |
| A-30. | H | H | Ethoxy | Methyl | CN | H |
| A-31. | Methoxy | H | Ethoxy | Methyl | CN | H |
| A-32. | Ethoxy | H | Ethoxy | Methyl | CN | H |
| A-33. | $OCF_3$ | H | Ethoxy | Methyl | CN | H |
| A-34. | H | H | $OCH_2F$ | Methyl | CN | H |
| A-35. | H | H | $OCHF_2$ | Methyl | CN | H |
| A-36. | H | H | $OCF_3$ | Methyl | CN | H |
| A-37. | H | H | $OCH_2CH_2F$ | Methyl | CN | H |
| A-38. | H | H | $OCH_2CHF_2$ | Methyl | CN | H |
| A-39. | H | H | $OCH_2CF_3$ | Methyl | CN | H |
| A-40. | H | H | Cl | Methyl | CN | H |
| A-41. | H | H | CN | Methyl | CN | H |
| A-42. | H | Methoxy | H | Methyl | CN | H |
| A-43. | H | H | H | Ethyl | CN | H |
| A-44. | Methoxy | H | H | Ethyl | CN | H |
| A-45. | Ethoxy | H | H | Ethyl | CN | H |
| A-46. | $OCF_3$ | H | H | Ethyl | CN | H |
| A-47. | H | H | Methoxy | Ethyl | CN | H |
| A-48. | Methoxy | H | Methoxy | Ethyl | CN | H |
| A-49. | Ethoxy | H | Methoxy | Ethyl | CN | H |
| A-50. | $OCF_3$ | H | Methoxy | Ethyl | CN | H |
| A-51. | H | H | Ethoxy | Ethyl | CN | H |
| A-52. | Methoxy | H | Ethoxy | Ethyl | CN | H |
| A-53. | Ethoxy | H | Ethoxy | Ethyl | CN | H |
| A-54. | $OCF_3$ | H | Ethoxy | Ethyl | CN | H |
| A-55. | H | H | $OCH_2F$ | Ethyl | CN | H |
| A-56. | H | H | $OCHF_2$ | Ethyl | CN | H |
| A-57. | H | H | $OCF_3$ | Ethyl | CN | H |
| A-58. | H | H | $OCH_2CH_2F$ | Ethyl | CN | H |
| A-59. | H | H | $OCH_2CHF_2$ | Ethyl | CN | H |
| A-60. | H | H | $OCH_2CF_3$ | Ethyl | CN | H |
| A-61. | H | H | Cl | Ethyl | CN | H |
| A-62. | H | H | CN | Ethyl | CN | H |
| A-63. | H | Methoxy | H | Ethyl | CN | H |
| A-64. | H | H | H | n-Propyl | CN | H |
| A-65. | Methoxy | H | H | n-Propyl | CN | H |
| A-66. | Ethoxy | H | H | n-Propyl | CN | H |
| A-67. | $OCF_3$ | H | H | n-Propyl | CN | H |
| A-68. | H | H | Methoxy | n-Propyl | CN | H |
| A-69. | Methoxy | H | Methoxy | n-Propyl | CN | H |
| A-70. | Ethoxy | H | Methoxy | n-Propyl | CN | H |

TABLE A-continued

| Example No. | R¹ | R² | R³ | R⁴ | R⁷ | R⁸ |
|---|---|---|---|---|---|---|
| A-71. | OCF$_3$ | H | Methoxy | n-Propyl | CN | H |
| A-72. | H | H | Ethoxy | n-Propyl | CN | H |
| A-73. | Methoxy | H | Ethoxy | n-Propyl | CN | H |
| A-74. | Ethoxy | H | Ethoxy | n-Propyl | CN | H |
| A-75. | OCF$_3$ | H | Ethoxy | n-Propyl | CN | H |
| A-76. | H | H | OCH$_2$F | n-Propyl | CN | H |
| A-77. | H | H | OCHF$_2$ | n-Propyl | CN | H |
| A-78. | H | H | OCF$_3$ | n-Propyl | CN | H |
| A-79. | H | H | OCH$_2$CH$_2$F | n-Propyl | CN | H |
| A-80. | H | H | OCH$_2$CHF$_2$ | n-Propyl | CN | H |
| A-81. | H | H | OCH$_2$CF$_3$ | n-Propyl | CN | H |
| A-82. | H | H | Cl | n-Propyl | CN | H |
| A-83. | H | H | CN | n-Propyl | CN | H |
| A-84. | H | Methoxy | H | n-Propyl | CN | H |
| A-85. | H | H | H | Isopropyl | CN | H |
| A-86. | Methoxy | H | H | Isopropyl | CN | H |
| A-87. | Ethoxy | H | H | Isopropyl | CN | H |
| A-88. | OCF$_3$ | H | H | Isopropyl | CN | H |
| A-89. | H | H | Methoxy | Isopropyl | CN | H |
| A-90. | Methoxy | H | Methoxy | Isopropyl | CN | H |
| A-91. | Ethoxy | H | Methoxy | Isopropyl | CN | H |
| A-92. | OCF$_3$ | H | Methoxy | Isopropyl | CN | H |
| A-93. | H | H | Ethoxy | Isopropyl | CN | H |
| A-94. | Methoxy | H | Ethoxy | Isopropyl | CN | H |
| A-95. | Ethoxy | H | Ethoxy | Isopropyl | CN | H |
| A-96. | OCF$_3$ | H | Ethoxy | Isopropyl | CN | H |
| A-97. | H | H | OCH$_2$F | Isopropyl | CN | H |
| A-98. | H | H | OCHF$_2$ | Isopropyl | CN | H |
| A-99. | H | H | OCF$_3$ | Isopropyl | CN | H |
| A-100. | H | H | OCH$_2$CH$_2$F | Isopropyl | CN | H |
| A-101. | H | H | OCH$_2$CHF$_2$ | Isopropyl | CN | H |
| A-102. | H | H | OCH$_2$CF$_3$ | Isopropyl | CN | H |
| A-103. | H | H | Cl | Isopropyl | CN | H |
| A-104. | H | H | CN | Isopropyl | CN | H |
| A-105. | H | Methoxy | H | Isopropyl | CN | H |
| A-106. | H | H | H | H | I | H |
| A-107. | Methoxy | H | H | H | I | H |
| A-108. | Ethoxy | H | H | H | I | H |
| A-109. | OCF$_3$ | H | H | H | I | H |
| A-110. | H | H | Methoxy | H | I | H |
| A-111. | Methoxy | H | Methoxy | H | I | H |
| A-112. | Ethoxy | H | Methoxy | H | I | H |
| A-113. | OCF$_3$ | H | Methoxy | H | I | H |
| A-114. | H | H | Ethoxy | H | I | H |
| A-115. | Methoxy | H | Ethoxy | H | I | H |
| A-116. | Ethoxy | H | Ethoxy | H | I | H |
| A-117. | OCF$_3$ | H | Ethoxy | H | I | H |
| A-118. | H | H | OCH$_2$F | H | I | H |
| A-119. | H | H | OCHF$_2$ | H | I | H |
| A-120. | H | H | OCF$_3$ | H | I | H |
| A-121. | H | H | OCH$_2$CH$_2$F | H | I | H |
| A-122. | H | H | OCH$_2$CHF$_2$ | H | I | H |
| A-123. | H | H | OCH$_2$CF$_3$ | H | I | H |
| A-124. | H | H | Cl | H | I | H |
| A-125. | H | H | CN | H | I | H |
| A-126. | H | Methoxy | H | H | I | H |
| A-127. | H | H | H | Methyl | I | H |
| A-128. | Methoxy | H | H | Methyl | I | H |
| A-129. | Ethoxy | H | H | Methyl | I | H |
| A-130. | OCF$_3$ | H | H | Methyl | I | H |
| A-131. | H | H | Methoxy | Methyl | I | H |
| A-132. | Methoxy | H | Methoxy | Methyl | I | H |
| A-133. | Ethoxy | H | Methoxy | Methyl | I | H |
| A-134. | OCF$_3$ | H | Methoxy | Methyl | I | H |
| A-135. | H | H | Ethoxy | Methyl | I | H |
| A-136. | Methoxy | H | Ethoxy | Methyl | I | H |
| A-137. | Ethoxy | H | Ethoxy | Methyl | I | H |
| A-138. | OCF$_3$ | H | Ethoxy | Methyl | I | H |
| A-139. | H | H | OCH$_2$F | Methyl | I | H |
| A-140. | H | H | OCHF$_2$ | Methyl | I | H |
| A-141. | H | H | OCF$_3$ | Methyl | I | H |
| A-142. | H | H | OCH$_2$CH$_2$F | Methyl | I | H |
| A-143. | H | H | OCH$_2$CHF$_2$ | Methyl | I | H |
| A-144. | H | H | OCH$_2$CF$_3$ | Methyl | I | H |
| A-145. | H | H | Cl | Methyl | I | H |
| A-146. | H | H | CN | Methyl | I | H |
| A-147. | H | Methoxy | H | Methyl | I | H |
| A-148. | H | H | H | Ethyl | I | H |
| A-149. | Methoxy | H | H | Ethyl | I | H |
| A-150. | Ethoxy | H | H | Ethyl | I | H |
| A-151. | OCF$_3$ | H | H | Ethyl | I | H |
| A-152. | H | H | Methoxy | Ethyl | I | H |
| A-153. | Methoxy | H | Methoxy | Ethyl | I | H |
| A-154. | Ethoxy | H | Methoxy | Ethyl | I | H |
| A-155. | OCF$_3$ | H | Methoxy | Ethyl | I | H |
| A-156. | H | H | Ethoxy | Ethyl | I | H |
| A-157. | Methoxy | H | Ethoxy | Ethyl | I | H |
| A-158. | Ethoxy | H | Ethoxy | Ethyl | I | H |
| A-159. | OCF$_3$ | H | Ethoxy | Ethyl | I | H |
| A-160. | H | H | OCH$_2$F | Ethyl | I | H |
| A-161. | H | H | OCHF$_2$ | Ethyl | I | H |
| A-162. | H | H | OCF$_3$ | Ethyl | I | H |
| A-163. | H | H | OCH$_2$CH$_2$F | Ethyl | I | H |
| A-164. | H | H | OCH$_2$CHF$_2$ | Ethyl | I | H |
| A-165. | H | H | OCH$_2$CF$_3$ | Ethyl | I | H |
| A-166. | H | H | Cl | Ethyl | I | H |
| A-167. | H | H | CN | Ethyl | I | H |
| A-168. | H | Methoxy | H | Ethyl | I | H |
| A-169. | H | H | H | n-Propyl | I | H |
| A-170. | Methoxy | H | H | n-Propyl | I | H |
| A-171. | Ethoxy | H | H | n-Propyl | I | H |
| A-172. | OCF$_3$ | H | H | n-Propyl | I | H |
| A-173. | H | H | Methoxy | n-Propyl | I | H |
| A-174. | Methoxy | H | Methoxy | n-Propyl | I | H |
| A-175. | Ethoxy | H | Methoxy | n-Propyl | I | H |
| A-176. | OCF$_3$ | H | Methoxy | n-Propyl | I | H |
| A-177. | H | H | Ethoxy | n-Propyl | I | H |
| A-178. | Methoxy | H | Ethoxy | n-Propyl | I | H |
| A-179. | Ethoxy | H | Ethoxy | n-Propyl | I | H |
| A-180. | OCF$_3$ | H | Ethoxy | n-Propyl | I | H |
| A-181. | H | H | OCH$_2$F | n-Propyl | I | H |
| A-182. | H | H | OCHF$_2$ | n-Propyl | I | H |
| A-183. | H | H | OCF$_3$ | n-Propyl | I | H |
| A-184. | H | H | OCH$_2$CH$_2$F | n-Propyl | I | H |
| A-185. | H | H | OCH$_2$CHF$_2$ | n-Propyl | I | H |
| A-186. | H | H | OCH$_2$CF$_3$ | n-Propyl | I | H |
| A-187. | H | H | Cl | n-Propyl | I | H |
| A-188. | H | H | CN | n-Propyl | I | H |
| A-189. | H | Methoxy | H | n-Propyl | I | H |
| A-190. | H | H | H | Isopropyl | I | H |
| A-191. | Methoxy | H | H | Isopropyl | I | H |
| A-192. | Ethoxy | H | H | Isopropyl | I | H |
| A-193. | OCF$_3$ | H | H | Isopropyl | I | H |
| A-194. | H | H | Methoxy | Isopropyl | I | H |
| A-195. | Methoxy | H | Methoxy | Isopropyl | I | H |
| A-196. | Ethoxy | H | Methoxy | Isopropyl | I | H |
| A-197. | OCF$_3$ | H | Methoxy | Isopropyl | I | H |
| A-198. | H | H | Ethoxy | Isopropyl | I | H |
| A-199. | Methoxy | H | Ethoxy | Isopropyl | I | H |
| A-200. | Ethoxy | H | Ethoxy | Isopropyl | I | H |
| A-201. | OCF$_3$ | H | Ethoxy | Isopropyl | I | H |
| A-202. | H | H | OCH$_2$F | Isopropyl | I | H |
| A-203. | H | H | OCHF$_2$ | Isopropyl | I | H |
| A-204. | H | H | OCF$_3$ | Isopropyl | I | H |
| A-205. | H | H | OCH$_2$CH$_2$F | Isopropyl | I | H |
| A-206. | H | H | OCH$_2$CHF$_2$ | Isopropyl | I | H |
| A-207. | H | H | OCH$_2$CF$_3$ | Isopropyl | I | H |
| A-208. | H | H | Cl | Isopropyl | I | H |
| A-209. | H | H | CN | Isopropyl | I | H |
| A-210. | H | Methoxy | H | Isopropyl | I | H |
| A-211. | H | H | H | H | Br | H |
| A-212. | Methoxy | H | H | H | Br | H |
| A-213. | Ethoxy | H | H | H | Br | H |
| A-214. | OCF$_3$ | H | H | H | Br | H |
| A-215. | H | H | Methoxy | H | Br | H |
| A-216. | Methoxy | H | Methoxy | H | Br | H |
| A-217. | Ethoxy | H | Methoxy | H | Br | H |
| A-218. | OCF$_3$ | H | Methoxy | H | Br | H |
| A-219. | H | H | Ethoxy | H | Br | H |
| A-220. | Methoxy | H | Ethoxy | H | Br | H |
| A-221. | Ethoxy | H | Ethoxy | H | Br | H |
| A-222. | OCF$_3$ | H | Ethoxy | H | Br | H |
| A-223. | H | H | OCH$_2$F | H | Br | H |
| A-224. | H | H | OCHF$_2$ | H | Br | H |
| A-225. | H | H | OCF$_3$ | H | Br | H |
| A-226. | H | H | OCH$_2$CH$_2$F | H | Br | H |

TABLE A-continued

| Example No. | R¹ | R² | R³ | R⁴ | R⁷ | R⁸ |
|---|---|---|---|---|---|---|
| A-227. | H | H | OCH$_2$CHF$_2$ | H | Br | H |
| A-228. | H | H | OCH$_2$CF$_3$ | H | Br | H |
| A-229. | H | H | Cl | H | Br | H |
| A-230. | H | H | CN | H | Br | H |
| A-231. | H | Methoxy | H | H | Br | H |
| A-232. | H | H | H | Methyl | Br | H |
| A-233. | Methoxy | H | H | Methyl | Br | H |
| A-234. | Ethoxy | H | H | Methyl | Br | H |
| A-235. | OCF$_3$ | H | H | Methyl | Br | H |
| A-236. | H | H | Methoxy | Methyl | Br | H |
| A-237. | Methoxy | H | Methoxy | Methyl | Br | H |
| A-238. | Ethoxy | H | Methoxy | Methyl | Br | H |
| A-239. | OCF$_3$ | H | Methoxy | Methyl | Br | H |
| A-240. | H | H | Ethoxy | Methyl | Br | H |
| A-241. | Methoxy | H | Ethoxy | Methyl | Br | H |
| A-242. | Ethoxy | H | Ethoxy | Methyl | Br | H |
| A-243. | OCF$_3$ | H | Ethoxy | Methyl | Br | H |
| A-244. | H | H | OCH$_2$F | Methyl | Br | H |
| A-245. | H | H | OCHF$_2$ | Methyl | Br | H |
| A-246. | H | H | OCF$_3$ | Methyl | Br | H |
| A-247. | H | H | OCH$_2$CH$_2$F | Methyl | Br | H |
| A-248. | H | H | OCH$_2$CHF$_2$ | Methyl | Br | H |
| A-249. | H | H | OCH$_2$CF$_3$ | Methyl | Br | H |
| A-250. | H | H | Cl | Methyl | Br | H |
| A-251. | H | H | CN | Methyl | Br | H |
| A-252. | H | Methoxy | H | Methyl | Br | H |
| A-253. | H | H | H | Ethyl | Br | H |
| A-254. | Methoxy | H | H | Ethyl | Br | H |
| A-255. | Ethoxy | H | H | Ethyl | Br | H |
| A-256. | OCF$_3$ | H | H | Ethyl | Br | H |
| A-257. | H | H | Methoxy | Ethyl | Br | H |
| A-258. | Methoxy | H | Methoxy | Ethyl | Br | H |
| A-259. | Ethoxy | H | Methoxy | Ethyl | Br | H |
| A-260. | OCF$_3$ | H | Methoxy | Ethyl | Br | H |
| A-261. | H | H | Ethoxy | Ethyl | Br | H |
| A-262. | Methoxy | H | Ethoxy | Ethyl | Br | H |
| A-263. | Ethoxy | H | Ethoxy | Ethyl | Br | H |
| A-264. | OCF$_3$ | H | Ethoxy | Ethyl | Br | H |
| A-265. | H | H | OCH$_2$F | Ethyl | Br | H |
| A-266. | H | H | OCHF$_2$ | Ethyl | Br | H |
| A-267. | H | H | OCF$_3$ | Ethyl | Br | H |
| A-268. | H | H | OCH$_2$CH$_2$F | Ethyl | Br | H |
| A-269. | H | H | OCH$_2$CHF$_2$ | Ethyl | Br | H |
| A-270. | H | H | OCH$_2$CF$_3$ | Ethyl | Br | H |
| A-271. | H | H | Cl | Ethyl | Br | H |
| A-272. | H | H | CN | Ethyl | Br | H |
| A-273. | H | Methoxy | H | Ethyl | Br | H |
| A-274. | H | H | H | n-Propyl | Br | H |
| A-275. | Methoxy | H | H | n-Propyl | Br | H |
| A-276. | Ethoxy | H | H | n-Propyl | Br | H |
| A-277. | OCF$_3$ | H | H | n-Propyl | Br | H |
| A-278. | H | H | Methoxy | n-Propyl | Br | H |
| A-279. | Methoxy | H | Methoxy | n-Propyl | Br | H |
| A-280. | Ethoxy | H | Methoxy | n-Propyl | Br | H |
| A-281. | OCF$_3$ | H | Methoxy | n-Propyl | Br | H |
| A-282. | H | H | Ethoxy | n-Propyl | Br | H |
| A-283. | Methoxy | H | Ethoxy | n-Propyl | Br | H |
| A-284. | Ethoxy | H | Ethoxy | n-Propyl | Br | H |
| A-285. | OCF$_3$ | H | Ethoxy | n-Propyl | Br | H |
| A-286. | H | H | OCH$_2$F | n-Propyl | Br | H |
| A-287. | H | H | OCHF$_2$ | n-Propyl | Br | H |
| A-288. | H | H | OCF$_3$ | n-Propyl | Br | H |
| A-289. | H | H | OCH$_2$CH$_2$F | n-Propyl | Br | H |
| A-290. | H | H | OCH$_2$CHF$_2$ | n-Propyl | Br | H |
| A-291. | H | H | OCH$_2$CF$_3$ | n-Propyl | Br | H |
| A-292. | H | H | Cl | n-Propyl | Br | H |
| A-293. | H | H | CN | n-Propyl | Br | H |
| A-294. | H | Methoxy | H | n-Propyl | Br | H |
| A-295. | H | H | H | Isopropyl | Br | H |
| A-296. | Methoxy | H | H | Isopropyl | Br | H |
| A-297. | Ethoxy | H | H | Isopropyl | Br | H |
| A-298. | OCF$_3$ | H | H | Isopropyl | Br | H |
| A-299. | H | H | Methoxy | Isopropyl | Br | H |
| A-300. | Methoxy | H | Methoxy | Isopropyl | Br | H |
| A-301. | Ethoxy | H | Methoxy | Isopropyl | Br | H |
| A-302. | OCF$_3$ | H | Methoxy | Isopropyl | Br | H |
| A-303. | H | H | Ethoxy | Isopropyl | Br | H |
| A-304. | Methoxy | H | Ethoxy | Isopropyl | Br | H |
| A-305. | Ethoxy | H | Ethoxy | Isopropyl | Br | H |
| A-306. | OCF$_3$ | H | Ethoxy | Isopropyl | Br | H |
| A-307. | H | H | OCH$_2$F | Isopropyl | Br | H |
| A-308. | H | H | OCHF$_2$ | Isopropyl | Br | H |
| A-309. | H | H | OCF$_3$ | Isopropyl | Br | H |
| A-310. | H | H | OCH$_2$CH$_2$F | Isopropyl | Br | H |
| A-311. | H | H | OCH$_2$CHF$_2$ | Isopropyl | Br | H |
| A-312. | H | H | OCH$_2$CF$_3$ | Isopropyl | Br | H |
| A-313. | H | H | Cl | Isopropyl | Br | H |
| A-314. | H | H | CN | Isopropyl | Br | H |
| A-315. | H | Methoxy | H | Isopropyl | Br | H |
| A-316. | H | H | H | H | Cl | H |
| A-317. | Methoxy | H | H | H | Cl | H |
| A-318. | Ethoxy | H | H | H | Cl | H |
| A-319. | OCF$_3$ | H | H | H | Cl | H |
| A-320. | H | H | Methoxy | H | Cl | H |
| A-321. | Methoxy | H | Methoxy | H | Cl | H |
| A-322. | Ethoxy | H | Methoxy | H | Cl | H |
| A-323. | OCF$_3$ | H | Methoxy | H | Cl | H |
| A-324. | H | H | Ethoxy | H | Cl | H |
| A-325. | Methoxy | H | Ethoxy | H | Cl | H |
| A-326. | Ethoxy | H | Ethoxy | H | Cl | H |
| A-327. | OCF$_3$ | H | Ethoxy | H | Cl | H |
| A-328. | H | H | OCH$_2$F | H | Cl | H |
| A-329. | H | H | OCHF$_2$ | H | Cl | H |
| A-330. | H | H | OCF$_3$ | H | Cl | H |
| A-331. | H | H | OCH$_2$CH$_2$F | H | Cl | H |
| A-332. | H | H | OCH$_2$CHF$_2$ | H | Cl | H |
| A-333. | H | H | OCH$_2$CF$_3$ | H | Cl | H |
| A-334. | H | H | Cl | H | Cl | H |
| A-335. | H | H | CN | H | Cl | H |
| A-336. | H | Methoxy | H | H | Cl | H |
| A-337. | H | H | H | Methyl | Cl | H |
| A-338. | Methoxy | H | H | Methyl | Cl | H |
| A-339. | Ethoxy | H | H | Methyl | Cl | H |
| A-340. | OCF$_3$ | H | H | Methyl | Cl | H |
| A-341. | H | H | Methoxy | Methyl | Cl | H |
| A-342. | Methoxy | H | Methoxy | Methyl | Cl | H |
| A-343. | Ethoxy | H | Methoxy | Methyl | Cl | H |
| A-344. | OCF$_3$ | H | Methoxy | Methyl | Cl | H |
| A-345. | H | H | Ethoxy | Methyl | Cl | H |
| A-346. | Methoxy | H | Ethoxy | Methyl | Cl | H |
| A-347. | Ethoxy | H | Ethoxy | Methyl | Cl | H |
| A-348. | OCF$_3$ | H | Ethoxy | Methyl | Cl | H |
| A-349. | H | H | OCH$_2$F | Methyl | Cl | H |
| A-350. | H | H | OCHF$_2$ | Methyl | Cl | H |
| A-351. | H | H | OCF$_3$ | Methyl | Cl | H |
| A-352. | H | H | OCH$_2$CH$_2$F | Methyl | Cl | H |
| A-353. | H | H | OCH$_2$CHF$_2$ | Methyl | Cl | H |
| A-354. | H | H | OCH$_2$CF$_3$ | Methyl | Cl | H |
| A-355. | H | H | Cl | Methyl | Cl | H |
| A-356. | H | H | CN | Methyl | Cl | H |
| A-357. | H | Methoxy | H | Methyl | Cl | H |
| A-358. | H | H | H | Ethyl | Cl | H |
| A-359. | Methoxy | H | H | Ethyl | Cl | H |
| A-360. | Ethoxy | H | H | Ethyl | Cl | H |
| A-361. | OCF$_3$ | H | H | Ethyl | Cl | H |
| A-362. | H | H | Methoxy | Ethyl | Cl | H |
| A-363. | Methoxy | H | Methoxy | Ethyl | Cl | H |
| A-364. | Ethoxy | H | Methoxy | Ethyl | Cl | H |
| A-365. | OCF$_3$ | H | Methoxy | Ethyl | Cl | H |
| A-366. | H | H | Ethoxy | Ethyl | Cl | H |
| A-367. | Methoxy | H | Ethoxy | Ethyl | Cl | H |
| A-368. | Ethoxy | H | Ethoxy | Ethyl | Cl | H |
| A-369. | OCF$_3$ | H | Ethoxy | Ethyl | Cl | H |
| A-370. | H | H | OCH$_2$F | Ethyl | Cl | H |
| A-371. | H | H | OCHF$_2$ | Ethyl | Cl | H |
| A-372. | H | H | OCF$_3$ | Ethyl | Cl | H |
| A-373. | H | H | OCH$_2$CH$_2$F | Ethyl | Cl | H |
| A-374. | H | H | OCH$_2$CHF$_2$ | Ethyl | Cl | H |
| A-375. | H | H | OCH$_2$CF$_3$ | Ethyl | Cl | H |
| A-376. | H | H | Cl | Ethyl | Cl | H |
| A-377. | H | H | CN | Ethyl | Cl | H |
| A-378. | H | Methoxy | H | Ethyl | Cl | H |
| A-379. | H | H | H | n-Propyl | Cl | H |
| A-380. | Methoxy | H | H | n-Propyl | Cl | H |
| A-381. | Ethoxy | H | H | n-Propyl | Cl | H |
| A-382. | OCF$_3$ | H | H | n-Propyl | Cl | H |

TABLE A-continued

| Example No. | R¹ | R² | R³ | R⁴ | R⁷ | R⁸ |
|---|---|---|---|---|---|---|
| A-383. | H | H | Methoxy | n-Propyl | Cl | H |
| A-384. | Methoxy | H | Methoxy | n-Propyl | Cl | H |
| A-385. | Ethoxy | H | Methoxy | n-Propyl | Cl | H |
| A-386. | OCF₃ | H | Methoxy | n-Propyl | Cl | H |
| A-387. | H | H | Ethoxy | n-Propyl | Cl | H |
| A-388. | Methoxy | H | Ethoxy | n-Propyl | Cl | H |
| A-389. | Ethoxy | H | Ethoxy | n-Propyl | Cl | H |
| A-390. | OCF₃ | H | Ethoxy | n-Propyl | Cl | H |
| A-391. | H | H | OCH₂F | n-Propyl | Cl | H |
| A-392. | H | H | OCHF₂ | n-Propyl | Cl | H |
| A-393. | H | H | OCF₃ | n-Propyl | Cl | H |
| A-394. | H | H | OCH₂CH₂F | n-Propyl | Cl | H |
| A-395. | H | H | OCH₂CHF₂ | n-Propyl | Cl | H |
| A-396. | H | H | OCH₂CF₃ | n-Propyl | Cl | H |
| A-397. | H | H | Cl | n-Propyl | Cl | H |
| A-398. | H | H | CN | n-Propyl | Cl | H |
| A-399. | H | Methoxy | H | n-Propyl | Cl | H |
| A-400. | H | H | H | Isopropyl | Cl | H |
| A-401. | Methoxy | H | H | Isopropyl | Cl | H |
| A-402. | Ethoxy | H | H | Isopropyl | Cl | H |
| A-403. | OCF₃ | H | H | Isopropyl | Cl | H |
| A-404. | H | H | Methoxy | Isopropyl | Cl | H |
| A-405. | Methoxy | H | Methoxy | Isopropyl | Cl | H |
| A-406. | Ethoxy | H | Methoxy | Isopropyl | Cl | H |
| A-407. | OCF₃ | H | Methoxy | Isopropyl | Cl | H |
| A-408. | H | H | Ethoxy | Isopropyl | Cl | H |
| A-409. | Methoxy | H | Ethoxy | Isopropyl | Cl | H |
| A-410. | Ethoxy | H | Ethoxy | Isopropyl | Cl | H |
| A-411. | OCF₃ | H | Ethoxy | Isopropyl | Cl | H |
| A-412. | H | H | OCH₂F | Isopropyl | Cl | H |
| A-413. | H | H | OCHF₂ | Isopropyl | Cl | H |
| A-414. | H | H | OCF₃ | Isopropyl | Cl | H |
| A-415. | H | H | OCH₂CH₂F | Isopropyl | Cl | H |
| A-416. | H | H | OCH₂CHF₂ | Isopropyl | Cl | H |
| A-417. | H | H | OCH₂CF₃ | Isopropyl | Cl | H |
| A-418. | H | H | Cl | Isopropyl | Cl | H |
| A-419. | H | H | CN | Isopropyl | Cl | H |
| A-420. | H | Methoxy | H | Isopropyl | Cl | H |
| A-421. | H | H | H | H | F | H |
| A-422. | Methoxy | H | H | H | F | H |
| A-423. | Ethoxy | H | H | H | F | H |
| A-424. | OCF₃ | H | H | H | F | H |
| A-425. | H | H | Methoxy | H | F | H |
| A-426. | Methoxy | H | Methoxy | H | F | H |
| A-427. | Ethoxy | H | Methoxy | H | F | H |
| A-428. | OCF₃ | H | Methoxy | H | F | H |
| A-429. | H | H | Ethoxy | H | F | H |
| A-430. | Methoxy | H | Ethoxy | H | F | H |
| A-431. | Ethoxy | H | Ethoxy | H | F | H |
| A-432. | OCF₃ | H | Ethoxy | H | F | H |
| A-433. | H | H | OCH₂F | H | F | H |
| A-434. | H | H | OCHF₂ | H | F | H |
| A-435. | H | H | OCF₃ | H | F | H |
| A-436. | H | H | OCH₂CH₂F | H | F | H |
| A-437. | H | H | OCH₂CHF₂ | H | F | H |
| A-438. | H | H | OCH₂CF₃ | H | F | H |
| A-439. | H | H | Cl | H | F | H |
| A-440. | H | H | CN | H | F | H |
| A-441. | H | Methoxy | H | H | F | H |
| A-442. | H | H | H | Methyl | F | H |
| A-443. | Methoxy | H | H | Methyl | F | H |
| A-444. | Ethoxy | H | H | Methyl | F | H |
| A-445. | OCF₃ | H | H | Methyl | F | H |
| A-446. | H | H | Methoxy | Methyl | F | H |
| A-447. | Methoxy | H | Methoxy | Methyl | F | H |
| A-448. | Ethoxy | H | Methoxy | Methyl | F | H |
| A-449. | OCF₃ | H | Methoxy | Methyl | F | H |
| A-450. | H | H | Ethoxy | Methyl | F | H |
| A-451. | Methoxy | H | Ethoxy | Methyl | F | H |
| A-452. | Ethoxy | H | Ethoxy | Methyl | F | H |
| A-453. | OCF₃ | H | Ethoxy | Methyl | F | H |
| A-454. | H | H | OCH₂F | Methyl | F | H |
| A-455. | H | H | OCHF₂ | Methyl | F | H |
| A-456. | H | H | OCF₃ | Methyl | F | H |
| A-457. | H | H | OCH₂CH₂F | Methyl | F | H |
| A-458. | H | H | OCH₂CHF₂ | Methyl | F | H |
| A-459. | H | H | OCH₂CF₃ | Methyl | F | H |
| A-460. | H | H | Cl | Methyl | F | H |
| A-461. | H | H | CN | Methyl | F | H |
| A-462. | H | Methoxy | H | Methyl | F | H |
| A-463. | H | H | H | Ethyl | F | H |
| A-464. | Methoxy | H | H | Ethyl | F | H |
| A-465. | Ethoxy | H | H | Ethyl | F | H |
| A-466. | OCF₃ | H | H | Ethyl | F | H |
| A-467. | H | H | Methoxy | Ethyl | F | H |
| A-468. | Methoxy | H | Methoxy | Ethyl | F | H |
| A-469. | Ethoxy | H | Methoxy | Ethyl | F | H |
| A-470. | OCF₃ | H | Methoxy | Ethyl | F | H |
| A-471. | H | H | Ethoxy | Ethyl | F | H |
| A-472. | Methoxy | H | Ethoxy | Ethyl | F | H |
| A-473. | Ethoxy | H | Ethoxy | Ethyl | F | H |
| A-474. | OCF₃ | H | Ethoxy | Ethyl | F | H |
| A-475. | H | H | OCH₂F | Ethyl | F | H |
| A-476. | H | H | OCHF₂ | Ethyl | F | H |
| A-477. | H | H | OCF₃ | Ethyl | F | H |
| A-478. | H | H | OCH₂CH₂F | Ethyl | F | H |
| A-479. | H | H | OCH₂CHF₂ | Ethyl | F | H |
| A-480. | H | H | OCH₂CF₃ | Ethyl | F | H |
| A-481. | H | H | Cl | Ethyl | F | H |
| A-482. | H | H | CN | Ethyl | F | H |
| A-483. | H | Methoxy | H | Ethyl | F | H |
| A-484. | H | H | H | n-Propyl | F | H |
| A-485. | Methoxy | H | H | n-Propyl | F | H |
| A-486. | Ethoxy | H | H | n-Propyl | F | H |
| A-487. | OCF₃ | H | H | n-Propyl | F | H |
| A-488. | H | H | Methoxy | n-Propyl | F | H |
| A-489. | Methoxy | H | Methoxy | n-Propyl | F | H |
| A-490. | Ethoxy | H | Methoxy | n-Propyl | F | H |
| A-491. | OCF₃ | H | Methoxy | n-Propyl | F | H |
| A-492. | H | H | Ethoxy | n-Propyl | F | H |
| A-493. | Methoxy | H | Ethoxy | n-Propyl | F | H |
| A-494. | Ethoxy | H | Ethoxy | n-Propyl | F | H |
| A-495. | OCF₃ | H | Ethoxy | n-Propyl | F | H |
| A-496. | H | H | OCH₂F | n-Propyl | F | H |
| A-497. | H | H | OCHF₂ | n-Propyl | F | H |
| A-498. | H | H | OCF₃ | n-Propyl | F | H |
| A-499. | H | H | OCH₂CH₂F | n-Propyl | F | H |
| A-500. | H | H | OCH₂CHF₂ | n-Propyl | F | H |
| A-501. | H | H | OCH₂CF₃ | n-Propyl | F | H |
| A-502. | H | H | Cl | n-Propyl | F | H |
| A-503. | H | H | CN | n-Propyl | F | H |
| A-504. | H | Methoxy | H | n-Propyl | F | H |
| A-505. | H | H | H | Isopropyl | F | H |
| A-506. | Methoxy | H | H | Isopropyl | F | H |
| A-507. | Ethoxy | H | H | Isopropyl | F | H |
| A-508. | OCF₃ | H | H | Isopropyl | F | H |
| A-509. | H | H | Methoxy | Isopropyl | F | H |
| A-510. | Methoxy | H | Methoxy | Isopropyl | F | H |
| A-511. | Ethoxy | H | Methoxy | Isopropyl | F | H |
| A-512. | OCF₃ | H | Methoxy | Isopropyl | F | H |
| A-513. | H | H | Ethoxy | Isopropyl | F | H |
| A-514. | Methoxy | H | Ethoxy | Isopropyl | F | H |
| A-515. | Ethoxy | H | Ethoxy | Isopropyl | F | H |
| A-516. | OCF₃ | H | Ethoxy | Isopropyl | F | H |
| A-517. | H | H | OCH₂F | Isopropyl | F | H |
| A-518. | H | H | OCHF₂ | Isopropyl | F | H |
| A-519. | H | H | OCF₃ | Isopropyl | F | H |
| A-520. | H | H | OCH₂CH₂F | Isopropyl | F | H |
| A-521. | H | H | OCH₂CHF₂ | Isopropyl | F | H |
| A-522. | H | H | OCH₂CF₃ | Isopropyl | F | H |
| A-523. | H | H | Cl | Isopropyl | F | H |
| A-524. | H | H | CN | Isopropyl | F | H |
| A-525. | H | Methoxy | H | Isopropyl | F | H |
| A-526. | H | H | H | H | CN | F |
| A-527. | Methoxy | H | H | H | CN | F |
| A-528. | Ethoxy | H | H | H | CN | F |
| A-529. | OCF₃ | H | H | H | CN | F |
| A-530. | H | H | Methoxy | H | CN | F |
| A-531. | Methoxy | H | Methoxy | H | CN | F |
| A-532. | Ethoxy | H | Methoxy | H | CN | F |
| A-533. | OCF₃ | H | Methoxy | H | CN | F |
| A-534. | H | H | Ethoxy | H | CN | F |
| A-535. | Methoxy | H | Ethoxy | H | CN | F |
| A-536. | Ethoxy | H | Ethoxy | H | CN | F |
| A-537. | OCF₃ | H | Ethoxy | H | CN | F |
| A-538. | H | H | OCH₂F | H | CN | F |

TABLE A-continued

| Example No. | R$^1$ | R$^2$ | R$^3$ | R$^4$ | R$^7$ | R$^8$ |
|---|---|---|---|---|---|---|
| A-539. | H | H | OCHF$_2$ | H | CN | F |
| A-540. | H | H | OCF$_3$ | H | CN | F |
| A-541. | H | H | OCH$_2$CH$_2$F | H | CN | F |
| A-542. | H | H | OCH$_2$CHF$_2$ | H | CN | F |
| A-543. | H | H | OCH$_2$CF$_3$ | H | CN | F |
| A-544. | H | H | Cl | H | CN | F |
| A-545. | H | H | CN | H | CN | F |
| A-546. | H | Methoxy | H | H | CN | F |
| A-547. | H | H | H | Methyl | CN | F |
| A-548. | Methoxy | H | H | Methyl | CN | F |
| A-549. | Ethoxy | H | H | Methyl | CN | F |
| A-550. | OCF$_3$ | H | H | Methyl | CN | F |
| A-551. | H | H | Methoxy | Methyl | CN | F |
| A-552. | Methoxy | H | Methoxy | Methyl | CN | F |
| A-553. | Ethoxy | H | Methoxy | Methyl | CN | F |
| A-554. | OCF$_3$ | H | Methoxy | Methyl | CN | F |
| A-555. | H | H | Ethoxy | Methyl | CN | F |
| A-556. | Methoxy | H | Ethoxy | Methyl | CN | F |
| A-557. | Ethoxy | H | Ethoxy | Methyl | CN | F |
| A-558. | OCF$_3$ | H | Ethoxy | Methyl | CN | F |
| A-559. | H | H | OCH$_2$F | Methyl | CN | F |
| A-560. | H | H | OCHF$_2$ | Methyl | CN | F |
| A-561. | H | H | OCF$_3$ | Methyl | CN | F |
| A-562. | H | H | OCH$_2$CH$_2$F | Methyl | CN | F |
| A-563. | H | H | OCH$_2$CHF$_2$ | Methyl | CN | F |
| A-564. | H | H | OCH$_2$CF$_3$ | Methyl | CN | F |
| A-565. | H | H | Cl | Methyl | CN | F |
| A-566. | H | H | CN | Methyl | CN | F |
| A-567. | H | Methoxy | H | Methyl | CN | F |
| A-568. | H | H | H | Ethyl | CN | F |
| A-569. | Methoxy | H | H | Ethyl | CN | F |
| A-570. | Ethoxy | H | H | Ethyl | CN | F |
| A-571. | OCF$_3$ | H | H | Ethyl | CN | F |
| A-572. | H | H | Methoxy | Ethyl | CN | F |
| A-573. | Methoxy | H | Methoxy | Ethyl | CN | F |
| A-574. | Ethoxy | H | Methoxy | Ethyl | CN | F |
| A-575. | OCF$_3$ | H | Methoxy | Ethyl | CN | F |
| A-576. | H | H | Ethoxy | Ethyl | CN | F |
| A-577. | Methoxy | H | Ethoxy | Ethyl | CN | F |
| A-578. | Ethoxy | H | Ethoxy | Ethyl | CN | F |
| A-579. | OCF$_3$ | H | Ethoxy | Ethyl | CN | F |
| A-580. | H | H | OCH$_2$F | Ethyl | CN | F |
| A-581. | H | H | OCHF$_2$ | Ethyl | CN | F |
| A-582. | H | H | OCF$_3$ | Ethyl | CN | F |
| A-583. | H | H | OCH$_2$CH$_2$F | Ethyl | CN | F |
| A-584. | H | H | OCH$_2$CHF$_2$ | Ethyl | CN | F |
| A-585. | H | H | OCH$_2$CF$_3$ | Ethyl | CN | F |
| A-586. | H | H | Cl | Ethyl | CN | F |
| A-587. | H | H | CN | Ethyl | CN | F |
| A-588. | H | Methoxy | H | Ethyl | CN | F |
| A-589. | H | H | H | n-Propyl | CN | F |
| A-590. | Methoxy | H | H | n-Propyl | CN | F |
| A-591. | Ethoxy | H | H | n-Propyl | CN | F |
| A-592. | OCF$_3$ | H | H | n-Propyl | CN | F |
| A-593. | H | H | Methoxy | n-Propyl | CN | F |
| A-594. | Methoxy | H | Methoxy | n-Propyl | CN | F |
| A-595. | Ethoxy | H | Methoxy | n-Propyl | CN | F |
| A-596. | OCF$_3$ | H | Methoxy | n-Propyl | CN | F |
| A-597. | H | H | Ethoxy | n-Propyl | CN | F |
| A-598. | Methoxy | H | Ethoxy | n-Propyl | CN | F |
| A-599. | Ethoxy | H | Ethoxy | n-Propyl | CN | F |
| A-600. | OCF$_3$ | H | Ethoxy | n-Propyl | CN | F |
| A-601. | H | H | OCH$_2$F | n-Propyl | CN | F |
| A-602. | H | H | OCHF$_2$ | n-Propyl | CN | F |
| A-603. | H | H | OCF$_3$ | n-Propyl | CN | F |
| A-604. | H | H | OCH$_2$CH$_2$F | n-Propyl | CN | F |
| A-605. | H | H | OCH$_2$CHF$_2$ | n-Propyl | CN | F |
| A-606. | H | H | OCH$_2$CF$_3$ | n-Propyl | CN | F |
| A-607. | H | H | Cl | n-Propyl | CN | F |
| A-608. | H | H | CN | n-Propyl | CN | F |
| A-609. | H | Methoxy | H | n-Propyl | CN | F |
| A-610. | H | H | H | Isopropyl | CN | F |
| A-611. | Methoxy | H | H | Isopropyl | CN | F |
| A-612. | Ethoxy | H | H | Isopropyl | CN | F |
| A-613. | OCF$_3$ | H | H | Isopropyl | CN | F |
| A-614. | H | H | Methoxy | Isopropyl | CN | F |
| A-615. | Methoxy | H | Methoxy | Isopropyl | CN | F |
| A-616. | Ethoxy | H | Methoxy | Isopropyl | CN | F |
| A-617. | OCF$_3$ | H | Methoxy | Isopropyl | CN | F |
| A-618. | H | H | Ethoxy | Isopropyl | CN | F |
| A-619. | Methoxy | H | Ethoxy | Isopropyl | CN | F |
| A-620. | Ethoxy | H | Ethoxy | Isopropyl | CN | F |
| A-621. | OCF$_3$ | H | Ethoxy | Isopropyl | CN | F |
| A-622. | H | H | OCH$_2$F | Isopropyl | CN | F |
| A-623. | H | H | OCHF$_2$ | Isopropyl | CN | F |
| A-624. | H | H | OCF$_3$ | Isopropyl | CN | F |
| A-625. | H | H | OCH$_2$CH$_2$F | Isopropyl | CN | F |
| A-626. | H | H | OCH$_2$CHF$_2$ | Isopropyl | CN | F |
| A-627. | H | H | OCH$_2$CF$_3$ | Isopropyl | CN | F |
| A-628. | H | H | Cl | Isopropyl | CN | F |
| A-629. | H | H | CN | Isopropyl | CN | F |
| A-630. | H | Methoxy | H | Isopropyl | CN | F |
| A-631. | H | H | H | H | Cl | F |
| A-632. | Methoxy | H | H | H | Cl | F |
| A-633. | Ethoxy | H | H | H | Cl | F |
| A-634. | OCF$_3$ | H | H | H | Cl | F |
| A-635. | H | H | Methoxy | H | Cl | F |
| A-636. | Methoxy | H | Methoxy | H | Cl | F |
| A-637. | Ethoxy | H | Methoxy | H | Cl | F |
| A-638. | OCF$_3$ | H | Methoxy | H | Cl | F |
| A-639. | H | H | Ethoxy | H | Cl | F |
| A-640. | Methoxy | H | Ethoxy | H | Cl | F |
| A-641. | Ethoxy | H | Ethoxy | H | Cl | F |
| A-642. | OCF$_3$ | H | Ethoxy | H | Cl | F |
| A-643. | H | H | OCH$_2$F | H | Cl | F |
| A-644. | H | H | OCHF$_2$ | H | Cl | F |
| A-645. | H | H | OCF$_3$ | H | Cl | F |
| A-646. | H | H | OCH$_2$CH$_2$F | H | Cl | F |
| A-647. | H | H | OCH$_2$CHF$_2$ | H | Cl | F |
| A-648. | H | H | OCH$_2$CF$_3$ | H | Cl | F |
| A-649. | H | H | Cl | H | Cl | F |
| A-650. | H | H | CN | H | Cl | F |
| A-651. | H | Methoxy | H | H | Cl | F |
| A-652. | H | H | H | Methyl | Cl | F |
| A-653. | Methoxy | H | H | Methyl | Cl | F |
| A-654. | Ethoxy | H | H | Methyl | Cl | F |
| A-655. | OCF$_3$ | H | H | Methyl | Cl | F |
| A-656. | H | H | Methoxy | Methyl | Cl | F |
| A-657. | Methoxy | H | Methoxy | Methyl | Cl | F |
| A-658. | Ethoxy | H | Methoxy | Methyl | Cl | F |
| A-659. | OCF$_3$ | H | Methoxy | Methyl | Cl | F |
| A-660. | H | H | Ethoxy | Methyl | Cl | F |
| A-661. | Methoxy | H | Ethoxy | Methyl | Cl | F |
| A-662. | Ethoxy | H | Ethoxy | Methyl | Cl | F |
| A-663. | OCF$_3$ | H | Ethoxy | Methyl | Cl | F |
| A-664. | H | H | OCH$_2$F | Methyl | Cl | F |
| A-665. | H | H | OCHF$_2$ | Methyl | Cl | F |
| A-666. | H | H | OCF$_3$ | Methyl | Cl | F |
| A-667. | H | H | OCH$_2$CH$_2$F | Methyl | Cl | F |
| A-668. | H | H | OCH$_2$CHF$_2$ | Methyl | Cl | F |
| A-669. | H | H | OCH$_2$CF$_3$ | Methyl | Cl | F |
| A-670. | H | H | Cl | Methyl | Cl | F |
| A-671. | H | H | CN | Methyl | Cl | F |
| A-672. | H | Methoxy | H | Methyl | Cl | F |
| A-673. | H | H | H | Ethyl | Cl | F |
| A-674. | Methoxy | H | H | Ethyl | Cl | F |
| A-675. | Ethoxy | H | H | Ethyl | Cl | F |
| A-676. | OCF$_3$ | H | H | Ethyl | Cl | F |
| A-677. | H | H | Methoxy | Ethyl | Cl | F |
| A-678. | Methoxy | H | Methoxy | Ethyl | Cl | F |
| A-679. | Ethoxy | H | Methoxy | Ethyl | Cl | F |
| A-680. | OCF$_3$ | H | Methoxy | Ethyl | Cl | F |
| A-681. | H | H | Ethoxy | Ethyl | Cl | F |
| A-682. | Methoxy | H | Ethoxy | Ethyl | Cl | F |
| A-683. | Ethoxy | H | Ethoxy | Ethyl | Cl | F |
| A-684. | OCF$_3$ | H | Ethoxy | Ethyl | Cl | F |
| A-685. | H | H | OCH$_2$F | Ethyl | Cl | F |
| A-686. | H | H | OCHF$_2$ | Ethyl | Cl | F |
| A-687. | H | H | OCF$_3$ | Ethyl | Cl | F |
| A-688. | H | H | OCH$_2$CH$_2$F | Ethyl | Cl | F |
| A-689. | H | H | OCH$_2$CHF$_2$ | Ethyl | Cl | F |
| A-690. | H | H | OCH$_2$CF$_3$ | Ethyl | Cl | F |
| A-691. | H | H | Cl | Ethyl | Cl | F |
| A-692. | H | H | CN | Ethyl | Cl | F |
| A-693. | H | Methoxy | H | Ethyl | Cl | F |
| A-694. | H | H | H | n-Propyl | Cl | F |

TABLE A-continued

| Example No. | R¹ | R² | R³ | R⁴ | R⁷ | R⁸ |
|---|---|---|---|---|---|---|
| A-695. | Methoxy | H | H | n-Propyl | Cl | F |
| A-696. | Ethoxy | H | H | n-Propyl | Cl | F |
| A-697. | $OCF_3$ | H | H | n-Propyl | Cl | F |
| A-698. | H | H | Methoxy | n-Propyl | Cl | F |
| A-699. | Methoxy | H | Methoxy | n-Propyl | Cl | F |
| A-700. | Ethoxy | H | Methoxy | n-Propyl | Cl | F |
| A-701. | $OCF_3$ | H | Methoxy | n-Propyl | Cl | F |
| A-702. | H | H | Ethoxy | n-Propyl | Cl | F |
| A-703. | Methoxy | H | Ethoxy | n-Propyl | Cl | F |
| A-704. | Ethoxy | H | Ethoxy | n-Propyl | Cl | F |
| A-705. | $OCF_3$ | H | Ethoxy | n-Propyl | Cl | F |
| A-706. | H | H | $OCH_2F$ | n-Propyl | Cl | F |
| A-707. | H | H | $OCHF_2$ | n-Propyl | Cl | F |
| A-708. | H | H | $OCF_3$ | n-Propyl | Cl | F |
| A-709. | H | H | $OCH_2CH_2F$ | n-Propyl | Cl | F |
| A-710. | H | H | $OCH_2CHF_2$ | n-Propyl | Cl | F |
| A-711. | H | H | $OCH_2CF_3$ | n-Propyl | Cl | F |
| A-712. | H | H | Cl | n-Propyl | Cl | F |
| A-713. | H | H | CN | n-Propyl | Cl | F |
| A-714. | H | Methoxy | H | n-Propyl | Cl | F |
| A-715. | H | H | H | Isopropyl | Cl | F |
| A-716. | Methoxy | H | H | Isopropyl | Cl | F |
| A-717. | Ethoxy | H | H | Isopropyl | Cl | F |
| A-718. | $OCF_3$ | H | H | Isopropyl | Cl | F |
| A-719. | H | H | Methoxy | Isopropyl | Cl | F |
| A-720. | Methoxy | H | Methoxy | Isopropyl | Cl | F |
| A-721. | Ethoxy | H | Methoxy | Isopropyl | Cl | F |
| A-722. | $OCF_3$ | H | Methoxy | Isopropyl | Cl | F |
| A-723. | H | H | Ethoxy | Isopropyl | Cl | F |
| A-724. | Methoxy | H | Ethoxy | Isopropyl | Cl | F |
| A-725. | Ethoxy | H | Ethoxy | Isopropyl | Cl | F |
| A-726. | $OCF_3$ | H | Ethoxy | Isopropyl | Cl | F |
| A-727. | H | H | $OCH_2F$ | Isopropyl | Cl | F |
| A-728. | H | H | $OCHF_2$ | Isopropyl | Cl | F |
| A-729. | H | H | $OCF_3$ | Isopropyl | Cl | F |
| A-730. | H | H | $OCH_2CH_2F$ | Isopropyl | Cl | F |
| A-731. | H | H | $OCH_2CHF_2$ | Isopropyl | Cl | F |
| A-732. | H | H | $OCH_2CF_3$ | Isopropyl | Cl | F |
| A-733. | H | H | Cl | Isopropyl | Cl | F |
| A-734. | H | H | CN | Isopropyl | Cl | F |
| A-735. | H | Methoxy | H | Isopropyl | Cl | F |
| A-736. | H | H | H | H | F | F |
| A-737. | Methoxy | H | H | H | F | F |
| A-738. | Ethoxy | H | H | H | F | F |
| A-739. | $OCF_3$ | H | H | H | F | F |
| A-740. | H | H | Methoxy | H | F | F |
| A-741. | Methoxy | H | Methoxy | H | F | F |
| A-742. | Ethoxy | H | Methoxy | H | F | F |
| A-743. | $OCF_3$ | H | Methoxy | H | F | F |
| A-744. | H | H | Ethoxy | H | F | F |
| A-745. | Methoxy | H | Ethoxy | H | F | F |
| A-746. | Ethoxy | H | Ethoxy | H | F | F |
| A-747. | $OCF_3$ | H | Ethoxy | H | F | F |
| A-748. | H | H | $OCH_2F$ | H | F | F |
| A-749. | H | H | $OCHF_2$ | H | F | F |
| A-750. | H | H | $OCF_3$ | H | F | F |
| A-751. | H | H | $OCH_2CH_2F$ | H | F | F |
| A-752. | H | H | $OCH_2CHF_2$ | H | F | F |
| A-753. | H | H | $OCH_2CF_3$ | H | F | F |
| A-754. | H | H | Cl | H | F | F |
| A-755. | H | H | CN | H | F | F |
| A-756. | H | Methoxy | H | H | F | F |
| A-757. | H | H | H | Methyl | F | F |
| A-758. | Methoxy | H | H | Methyl | F | F |
| A-759. | Ethoxy | H | H | Methyl | F | F |
| A-760. | $OCF_3$ | H | H | Methyl | F | F |
| A-761. | H | H | Methoxy | Methyl | F | F |
| A-762. | Methoxy | H | Methoxy | Methyl | F | F |
| A-763. | Ethoxy | H | Methoxy | Methyl | F | F |
| A-764. | $OCF_3$ | H | Methoxy | Methyl | F | F |
| A-765. | H | H | Ethoxy | Methyl | F | F |
| A-766. | Methoxy | H | Ethoxy | Methyl | F | F |
| A-767. | Ethoxy | H | Ethoxy | Methyl | F | F |
| A-768. | $OCF_3$ | H | Ethoxy | Methyl | F | F |
| A-769. | H | H | $OCH_2F$ | Methyl | F | F |
| A-770. | H | H | $OCHF_2$ | Methyl | F | F |
| A-771. | H | H | $OCF_3$ | Methyl | F | F |
| A-772. | H | H | $OCH_2CH_2F$ | Methyl | F | F |
| A-773. | H | H | $OCH_2CHF_2$ | Methyl | F | F |
| A-774. | H | H | $OCH_2CF_3$ | Methyl | F | F |
| A-775. | H | H | Cl | Methyl | F | F |
| A-776. | H | H | CN | Methyl | F | F |
| A-777. | H | Methoxy | H | Methyl | F | F |
| A-778. | H | H | H | Ethyl | F | F |
| A-779. | Methoxy | H | H | Ethyl | F | F |
| A-780. | Ethoxy | H | H | Ethyl | F | F |
| A-781. | $OCF_3$ | H | H | Ethyl | F | F |
| A-782. | H | H | Methoxy | Ethyl | F | F |
| A-783. | Methoxy | H | Methoxy | Ethyl | F | F |
| A-784. | Ethoxy | H | Methoxy | Ethyl | F | F |
| A-785. | $OCF_3$ | H | Methoxy | Ethyl | F | F |
| A-786. | H | H | Ethoxy | Ethyl | F | F |
| A-787. | Methoxy | H | Ethoxy | Ethyl | F | F |
| A-788. | Ethoxy | H | Ethoxy | Ethyl | F | F |
| A-789. | $OCF_3$ | H | Ethoxy | Ethyl | F | F |
| A-790. | H | H | $OCH_2F$ | Ethyl | F | F |
| A-791. | H | H | $OCHF_2$ | Ethyl | F | F |
| A-792. | H | H | $OCF_3$ | Ethyl | F | F |
| A-793. | H | H | $OCH_2CH_2F$ | Ethyl | F | F |
| A-794. | H | H | $OCH_2CHF_2$ | Ethyl | F | F |
| A-795. | H | H | $OCH_2CF_3$ | Ethyl | F | F |
| A-796. | H | H | Cl | Ethyl | F | F |
| A-797. | H | H | CN | Ethyl | F | F |
| A-798. | H | Methoxy | H | Ethyl | F | F |
| A-799. | H | H | H | n-Propyl | F | F |
| A-800. | Methoxy | H | H | n-Propyl | F | F |
| A-801. | Ethoxy | H | H | n-Propyl | F | F |
| A-802. | $OCF_3$ | H | H | n-Propyl | F | F |
| A-803. | H | H | Methoxy | n-Propyl | F | F |
| A-804. | Methoxy | H | Methoxy | n-Propyl | F | F |
| A-805. | Ethoxy | H | Methoxy | n-Propyl | F | F |
| A-806. | $OCF_3$ | H | Methoxy | n-Propyl | F | F |
| A-807. | H | H | Ethoxy | n-Propyl | F | F |
| A-808. | Methoxy | H | Ethoxy | n-Propyl | F | F |
| A-809. | Ethoxy | H | Ethoxy | n-Propyl | F | F |
| A-810. | $OCF_3$ | H | Ethoxy | n-Propyl | F | F |
| A-811. | H | H | $OCH_2F$ | n-Propyl | F | F |
| A-812. | H | H | $OCHF_2$ | n-Propyl | F | F |
| A-813. | H | H | $OCF_3$ | n-Propyl | F | F |
| A-814. | H | H | $OCH_2CH_2F$ | n-Propyl | F | F |
| A-815. | H | H | $OCH_2CHF_2$ | n-Propyl | F | F |
| A-816. | H | H | $OCH_2CF_3$ | n-Propyl | F | F |
| A-817. | H | H | Cl | n-Propyl | F | F |
| A-818. | H | H | CN | n-Propyl | F | F |
| A-819. | H | Methoxy | H | n-Propyl | F | F |
| A-820. | H | H | H | Isopropyl | F | F |
| A-821. | Methoxy | H | H | Isopropyl | F | F |
| A-822. | Ethoxy | H | H | Isopropyl | F | F |
| A-823. | $OCF_3$ | H | H | Isopropyl | F | F |
| A-824. | H | H | Methoxy | Isopropyl | F | F |
| A-825. | Methoxy | H | Methoxy | Isopropyl | F | F |
| A-826. | Ethoxy | H | Methoxy | Isopropyl | F | F |
| A-827. | $OCF_3$ | H | Methoxy | Isopropyl | F | F |
| A-828. | H | H | Ethoxy | Isopropyl | F | F |
| A-829. | Methoxy | H | Ethoxy | Isopropyl | F | F |
| A-830. | Ethoxy | H | Ethoxy | Isopropyl | F | F |
| A-831. | $OCF_3$ | H | Ethoxy | Isopropyl | F | F |
| A-832. | H | H | $OCH_2F$ | Isopropyl | F | F |
| A-833. | H | H | $OCHF_2$ | Isopropyl | F | F |
| A-834. | H | H | $OCF_3$ | Isopropyl | F | F |
| A-835. | H | H | $OCH_2CH_2F$ | Isopropyl | F | F |
| A-836. | H | H | $OCH_2CHF_2$ | Isopropyl | F | F |
| A-837. | H | H | $OCH_2CF_3$ | Isopropyl | F | F |
| A-838. | H | H | Cl | Isopropyl | F | F |
| A-839. | H | H | CN | Isopropyl | F | F |
| A-840. | H | Methoxy | H | Isopropyl | F | F |
| A-841. | H | H | H | H | F | Cl |
| A-842. | Methoxy | H | H | H | F | Cl |
| A-843. | Ethoxy | H | H | H | F | Cl |
| A-844. | $OCF_3$ | H | H | H | F | Cl |
| A-845. | H | H | Methoxy | H | F | Cl |
| A-846. | Methoxy | H | Methoxy | H | F | Cl |
| A-847. | Ethoxy | H | Methoxy | H | F | Cl |
| A-848. | $OCF_3$ | H | Methoxy | H | F | Cl |
| A-849. | H | H | Ethoxy | H | F | Cl |
| A-850. | Methoxy | H | Ethoxy | H | F | Cl |

TABLE A-continued

| Example No. | R$^1$ | R$^2$ | R$^3$ | R$^4$ | R$^7$ | R$^8$ |
|---|---|---|---|---|---|---|
| A-851. | Ethoxy | H | Ethoxy | H | F | Cl |
| A-852. | OCF$_3$ | H | Ethoxy | H | F | Cl |
| A-853. | H | H | OCH$_2$F | H | F | Cl |
| A-854. | H | H | OCHF$_2$ | H | F | Cl |
| A-855. | H | H | OCF$_3$ | H | F | Cl |
| A-856. | H | H | OCH$_2$CH$_2$F | H | F | Cl |
| A-857. | H | H | OCH$_2$CHF$_2$ | H | F | Cl |
| A-858. | H | H | OCH$_2$CF$_3$ | H | F | Cl |
| A-859. | H | H | Cl | H | F | Cl |
| A-860. | H | H | CN | H | F | Cl |
| A-861. | H | Methoxy | H | H | F | Cl |
| A-862. | H | H | H | Methyl | F | Cl |
| A-863. | Methoxy | H | H | Methyl | F | Cl |
| A-864. | Ethoxy | H | H | Methyl | F | Cl |
| A-865. | OCF$_3$ | H | H | Methyl | F | Cl |
| A-866. | H | H | Methoxy | Methyl | F | Cl |
| A-867. | Methoxy | H | Methoxy | Methyl | F | Cl |
| A-868. | Ethoxy | H | Methoxy | Methyl | F | Cl |
| A-869. | OCF$_3$ | H | Methoxy | Methyl | F | Cl |
| A-870. | H | H | Ethoxy | Methyl | F | Cl |
| A-871. | Methoxy | H | Ethoxy | Methyl | F | Cl |
| A-872. | Ethoxy | H | Ethoxy | Methyl | F | Cl |
| A-873. | OCF$_3$ | H | Ethoxy | Methyl | F | Cl |
| A-874. | H | H | OCH$_2$F | Methyl | F | Cl |
| A-875. | H | H | OCHF$_2$ | Methyl | F | Cl |
| A-876. | H | H | OCF$_3$ | Methyl | F | Cl |
| A-877. | H | H | OCH$_2$CH$_2$F | Methyl | F | Cl |
| A-878. | H | H | OCH$_2$CHF$_2$ | Methyl | F | Cl |
| A-879. | H | H | OCH$_2$CF$_3$ | Methyl | F | Cl |
| A-880. | H | H | Cl | Methyl | F | Cl |
| A-881. | H | H | CN | Methyl | F | Cl |
| A-882. | H | Methoxy | H | Methyl | F | Cl |
| A-883. | H | H | H | Ethyl | F | Cl |
| A-884. | Methoxy | H | H | Ethyl | F | Cl |
| A-885. | Ethoxy | H | H | Ethyl | F | Cl |
| A-886. | OCF$_3$ | H | H | Ethyl | F | Cl |
| A-887. | H | H | Methoxy | Ethyl | F | Cl |
| A-888. | Methoxy | H | Methoxy | Ethyl | F | Cl |
| A-889. | Ethoxy | H | Methoxy | Ethyl | F | Cl |
| A-890. | OCF$_3$ | H | Methoxy | Ethyl | F | Cl |
| A-891. | H | H | Ethoxy | Ethyl | F | Cl |
| A-892. | Methoxy | H | Ethoxy | Ethyl | F | Cl |
| A-893. | Ethoxy | H | Ethoxy | Ethyl | F | Cl |
| A-894. | OCF$_3$ | H | Ethoxy | Ethyl | F | Cl |
| A-895. | H | H | OCH$_2$F | Ethyl | F | Cl |
| A-896. | H | H | OCHF$_2$ | Ethyl | F | Cl |
| A-897. | H | H | OCF$_3$ | Ethyl | F | Cl |
| A-898. | H | H | OCH$_2$CH$_2$F | Ethyl | F | Cl |
| A-899. | H | H | OCH$_2$CHF$_2$ | Ethyl | F | Cl |
| A-900. | H | H | OCH$_2$CF$_3$ | Ethyl | F | Cl |
| A-901. | H | H | Cl | Ethyl | F | Cl |
| A-902. | H | H | CN | Ethyl | F | Cl |
| A-903. | H | Methoxy | H | Ethyl | F | Cl |
| A-904. | H | H | H | n-Propyl | F | Cl |
| A-905. | Methoxy | H | H | n-Propyl | F | Cl |
| A-906. | Ethoxy | H | H | n-Propyl | F | Cl |
| A-907. | OCF$_3$ | H | H | n-Propyl | F | Cl |
| A-908. | H | H | Methoxy | n-Propyl | F | Cl |
| A-909. | Methoxy | H | Methoxy | n-Propyl | F | Cl |
| A-910. | Ethoxy | H | Methoxy | n-Propyl | F | Cl |
| A-911. | OCF$_3$ | H | Methoxy | n-Propyl | F | Cl |
| A-912. | H | H | Ethoxy | n-Propyl | F | Cl |
| A-913. | Methoxy | H | Ethoxy | n-Propyl | F | Cl |
| A-914. | Ethoxy | H | Ethoxy | n-Propyl | F | Cl |
| A-915. | OCF$_3$ | H | Ethoxy | n-Propyl | F | Cl |
| A-916. | H | H | OCH$_2$F | n-Propyl | F | Cl |
| A-917. | H | H | OCHF$_2$ | n-Propyl | F | Cl |
| A-918. | H | H | OCF$_3$ | n-Propyl | F | Cl |
| A-919. | H | H | OCH$_2$CH$_2$F | n-Propyl | F | Cl |
| A-920. | H | H | OCH$_2$CHF$_2$ | n-Propyl | F | Cl |
| A-921. | H | H | OCH$_2$CF$_3$ | n-Propyl | F | Cl |
| A-922. | H | H | Cl | n-Propyl | F | Cl |
| A-923. | H | H | CN | n-Propyl | F | Cl |
| A-924. | H | Methoxy | H | n-Propyl | F | Cl |
| A-925. | H | H | H | Isopropyl | F | Cl |
| A-926. | Methoxy | H | H | Isopropyl | F | Cl |
| A-927. | Ethoxy | H | H | Isopropyl | F | Cl |
| A-928. | OCF$_3$ | H | H | Isopropyl | F | Cl |
| A-929. | H | H | Methoxy | Isopropyl | F | Cl |
| A-930. | Methoxy | H | Methoxy | Isopropyl | F | Cl |
| A-931. | Ethoxy | H | Methoxy | Isopropyl | F | Cl |
| A-932. | OCF$_3$ | H | Methoxy | Isopropyl | F | Cl |
| A-933. | H | H | Ethoxy | Isopropyl | F | Cl |
| A-934. | Methoxy | H | Ethoxy | Isopropyl | F | Cl |
| A-935. | Ethoxy | H | Ethoxy | Isopropyl | F | Cl |
| A-936. | OCF$_3$ | H | Ethoxy | Isopropyl | F | Cl |
| A-937. | H | H | OCH$_2$F | Isopropyl | F | Cl |
| A-938. | H | H | OCHF$_2$ | Isopropyl | F | Cl |
| A-939. | H | H | OCF$_3$ | Isopropyl | F | Cl |
| A-940. | H | H | OCH$_2$CH$_2$F | Isopropyl | F | Cl |
| A-941. | H | H | OCH$_2$CHF$_2$ | Isopropyl | F | Cl |
| A-942. | H | H | OCH$_2$CF$_3$ | Isopropyl | F | Cl |
| A-943. | H | H | Cl | Isopropyl | F | Cl |
| A-944. | H | H | CN | Isopropyl | F | Cl |
| A-945. | H | Methoxy | H | Isopropyl | F | Cl |

The compounds most preferred among the compounds 1.1 to 1.56 mentioned above are those of the formula I.1.

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. Since the compounds of the invention in most cases have a single center of asymmetry and no axis/plane of chirality, a nonracemic mixture can also be defined in these cases as a mixture of enantiomers in which either the R or the S enantiomer predominates. Substantially enantiopure compounds can in these cases accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular of at least 98% ee.

The invention thus relates both to the pure enantiomers and to mixtures thereof, e.g. mixtures in which one enantiomer is present in enriched form, but also to the racemates. The invention also relates to the pharmaceutically acceptable salts and the prodrugs of the pure enantiomers of compounds I, and the mixtures of enantiomers in the form of the pharmaceutically acceptable salts and prodrugs of compounds I.

Examples of synthetic routes for preparing the oxindole derivatives of the invention are described below.

The compounds of the invention can be prepared by using methods described in WO 2005/030755 and WO 2006/005609 for synthesizing analogous compounds, and the preparation is outlined by way of example in synthesis schemes 1 to 5. The variables in these synthetic schemes have the same meanings as in formula I.

The 3-hydroxy-1,3-dihydroindol-2-ones IV can be obtained by addition of metallated benzenes or heterocycles III onto the 3-keto group of the isatins II. The metallated benzenes or heterocycles, such as, for example, the corresponding Grignard (Mg) or organyllithium compound, can be obtained in any conventional way from halogen or hydrocarbon compounds. Examples of methods are present in Houben-Weyl, Methoden der Organischen Chemie, vol. 13, 1-2, chapter on Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV which comprise an iodine or bromine as radical $R^7$ or $R^8$ in position 5 and/or 6 for example in the 6-membered aromatic ring can be converted with KCN or $Zn(CN)_2$ with Pd(0) catalysis in solvents such as dimethylformamide or tetrahydrofuran, where appropriate also with addition of bases such as $K_2CO_3$ or other carbonates or amines, at elevated temperature into the analogous cyan-containing 3-hydroxyoxindole IV. Pd(0) salts which can be taken are for example transition metal complexes which are prepared in situ from $PdCl_2$ or $Pd(OAc)_2$ by addition of phosphines such as tris(orthotolyl)phosphine. It is likewise possible to employ commercial palladium complexes such as, for example, the catalyst tetrakis(triphenylphosphine)palladium (0) and/or additions of phosphine ligands.

The 3-hydroxyoxindoles IV can be converted into the compounds V which have a leaving group LG' in position 3, where the leaving group LG' is a conventional leaving group such as, for example, chlorine or bromide, but also activated OH, such as tosylate or triflate. The intermediate V with for example LG'=chlorine can be prepared by treating the alcohol IV with thionyl chloride in the presence of a base such as, for example, pyridine, in a suitable solvent such as, for example, dichloromethane.

The compounds V can subsequently be reacted with a carboxylic acid, a carboxamide, an amine or an alcohol VIII in a substitution reaction to give the amines VI. The compounds VI can subsequently be converted by treatment with sulfonyl chlorides VII after deprotonation with a strong base such as, for example, potassium tert-butoxide or sodium hydride in DMF into the sulfonylated product I. The sulfonyl chlorides VII employed can either be purchased or be prepared by known processes (for example J. Med. Chem. 40, 1149 (1997)). (Synthesis scheme 1)

Compounds I of the invention with $R^4$=H can be prepared by using appropriate Boc-protected compounds VIII ($R^4$=Boc). The Boc protective group can subsequently be removed, for example by treatment with trifluoroacetic acid in dichloromethane.

The compounds VIII can either be purchased or can be prepared by conventional substitution reactions on the (hetero)aromatic compound A, where appropriate with use of protective group techniques.

Synthesis scheme 1:

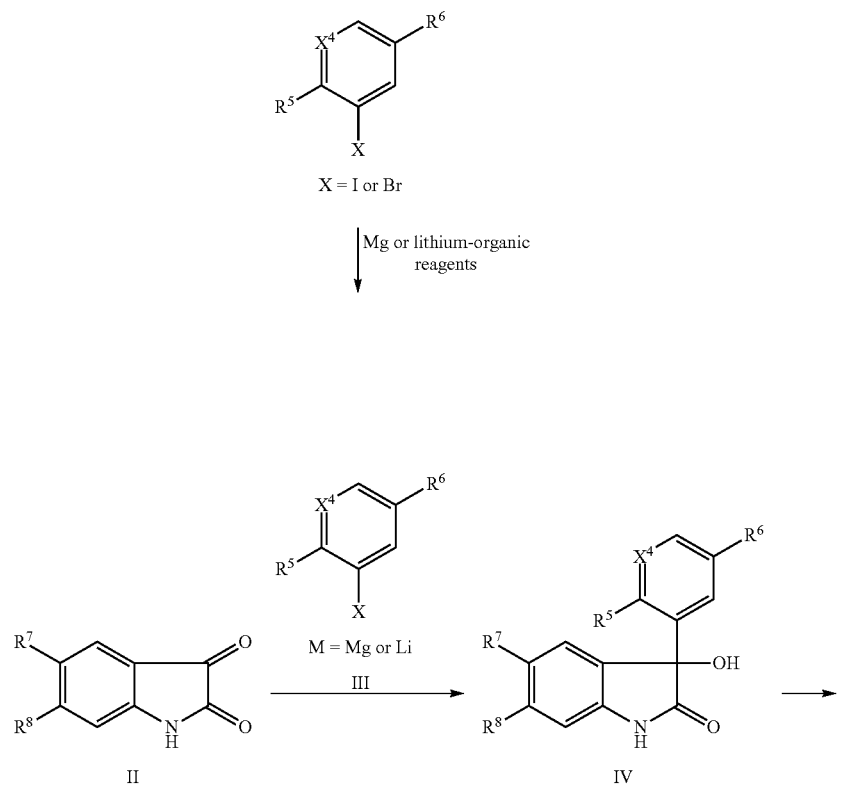

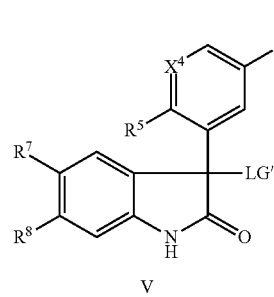

V

LG' = Leaving group
such as, for example, Cl

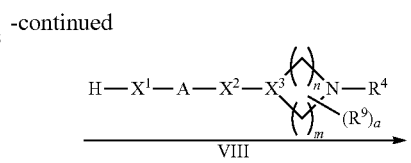

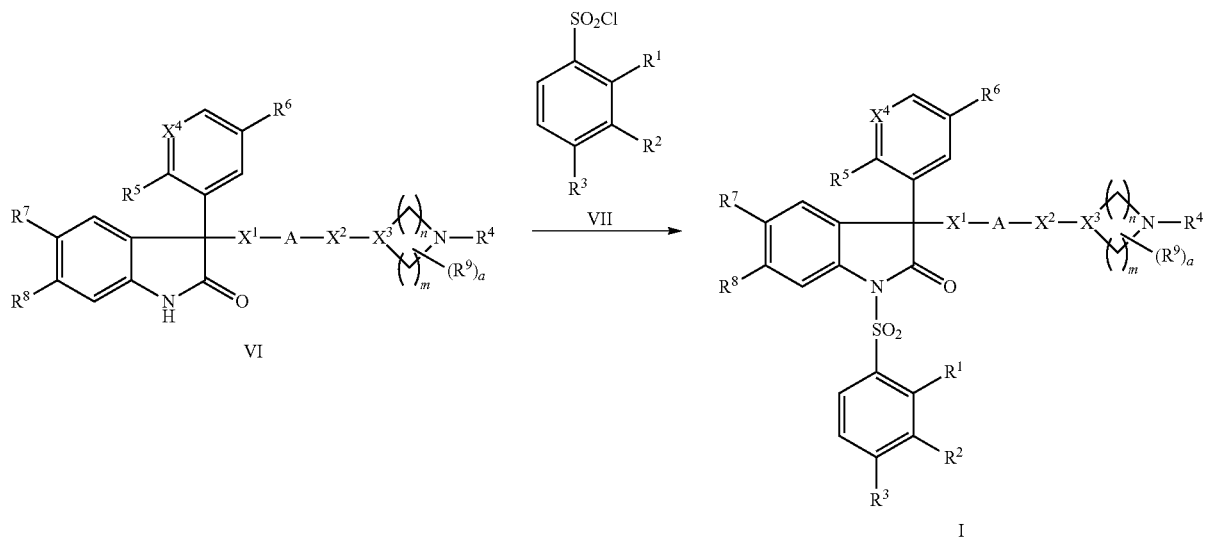

Compounds I in which $X^1$ is —$NR^{11}$—CO— can alternatively be prepared by reacting the compounds V with amines such as, for example, ammonia or an amine $NH_2R^{11}$ in a substitution reaction to give the amines IX.

The compounds IX can subsequently be converted by treatment with sulfonyl chlorides VII after deprotonation with a strong base such as, for example, potassium tert-butoxide or sodium hydride in DMF into the sulfonylated product X. The sulfonyl chlorides VII employed can either be purchased or be prepared by known processes (for example J. Med. Chem. 40, 1149 (1997)).

Subsequent reaction with carbonyl chlorides XI leads to the compounds of the invention of the general formula (I) with carboxamide bridge ($X^1$=$NR^{11}$—CO).

The compounds I of the invention with $R^4$=H can be prepared by using appropriate Boc-protected compounds XI($R^4$=Boc). The Boc-protective group can subsequently be removed, for example by treatment with trifluoroacetic acid in dichloromethane.

The compounds XI can either be purchased or can be prepared by conventional substitution reactions on the (hetero)aromatic compound A, where appropriate with use of protective group techniques.

Synthesis scheme 2:

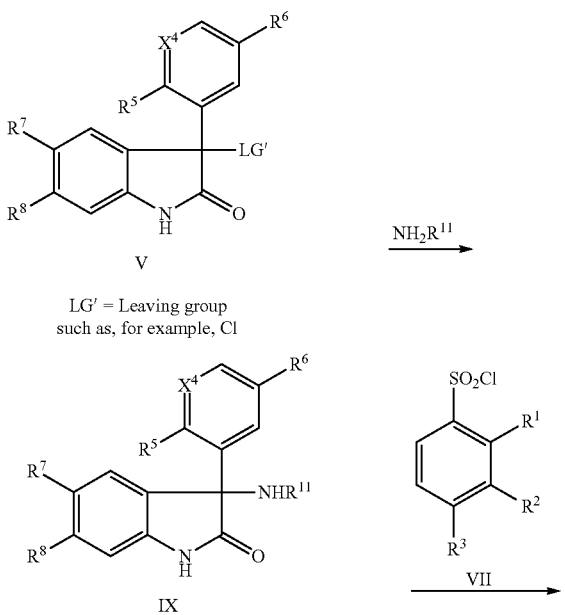

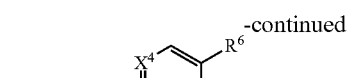
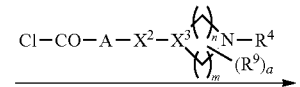
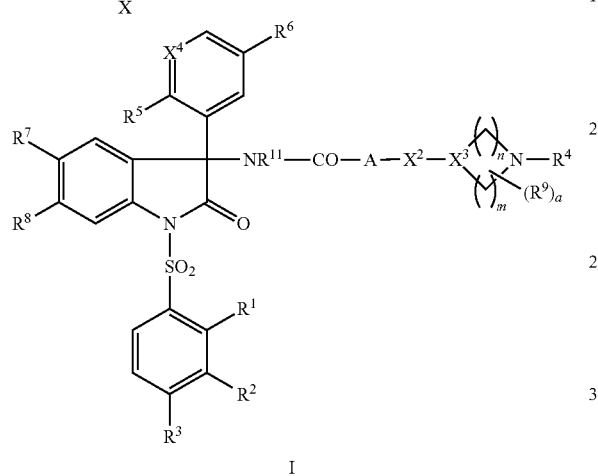
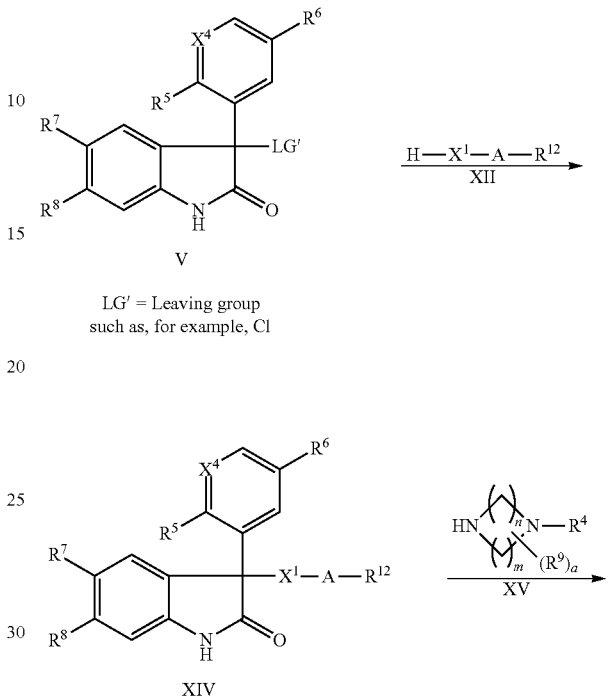

Alternatively, the sulfonylation in scheme 2 can also be carried out only after reaction with the compound XI.

Compounds of the formula I in which $X^2$ is a single bond, and $X^3$ is N, can also be prepared alternatively by employing in the above reaction schemes 1 and 2 instead of compound VIII (in scheme 1) or instead of compound XI (in scheme 2) a compound XII (reaction scheme 3) or a compound XIII (reaction scheme 4) in which $R^{12}$ is halogen, CN, $OR^a$ or $NR^bR^c$ in which $R^a$ is H, $C_1$-$C_4$-alkyl, phenyl or benzyl; and $R^b$ and $R^c$ are independently of one another H, $C_1$-$C_4$-alkyl, $C_1$-$C_4$-alkoxy, phenyl or benzyl and is preferably halogen, in particular Br. The compound XIV resulting in scheme 3 can subsequently be coupled with the cyclic amine XV with palladium catalysis as in the process described in Tetrahedron Asym. 1999, 10, 1831, to give the compound XVI which can be converted, in analogy to the sulfonylation reaction described above with the sulfonyl chloride VII, into the compound I' of the invention in which $X^2$ is a single bond, and $X^3$ is N. The compound XVII resulting in scheme 4 can be coupled with the cyclic amine XV with palladium catalysis as in the process described in Tetrahedron Asym. 1999, 10, 1831 to give the compound I'.

Compound XIV can also be alternatively subjected first to the sulfonylation reaction to obtain the compound XVIII and only then be reacted with the amine of the formula XV to give the compound I (reaction scheme 5).

Compounds I' of the invention with $R^4$=H can be prepared by using appropriate Boc-protected compounds XV ($R^4$=Boc). The Boc-protective group can subsequently be removed, for example by treatment with trifluoroacetic acid in dichloromethane.

The compounds XII, XIII and XV can either be purchased or can be prepared by conventional substitution reactions on the (hetero)aromatic compound A or on the N-heterocycle, where appropriate with use of protective group techniques.

Reaction scheme 3

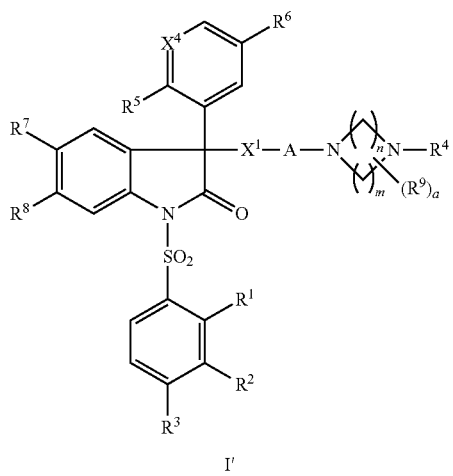

Reaction scheme 4:
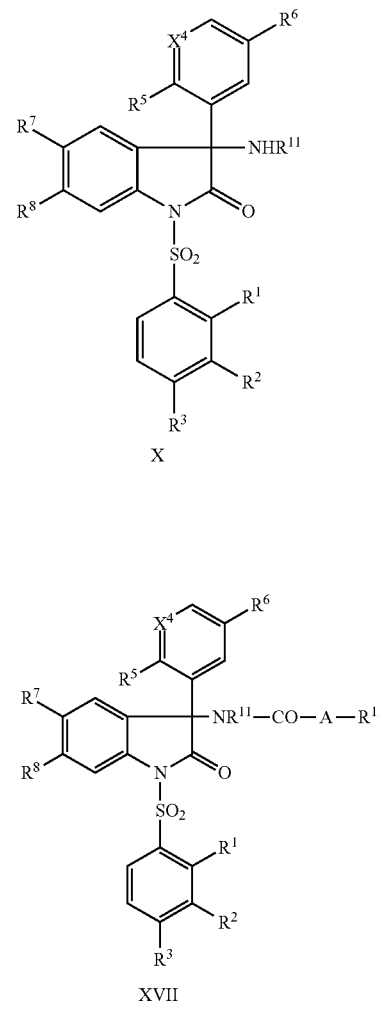
Reaction scheme 5:
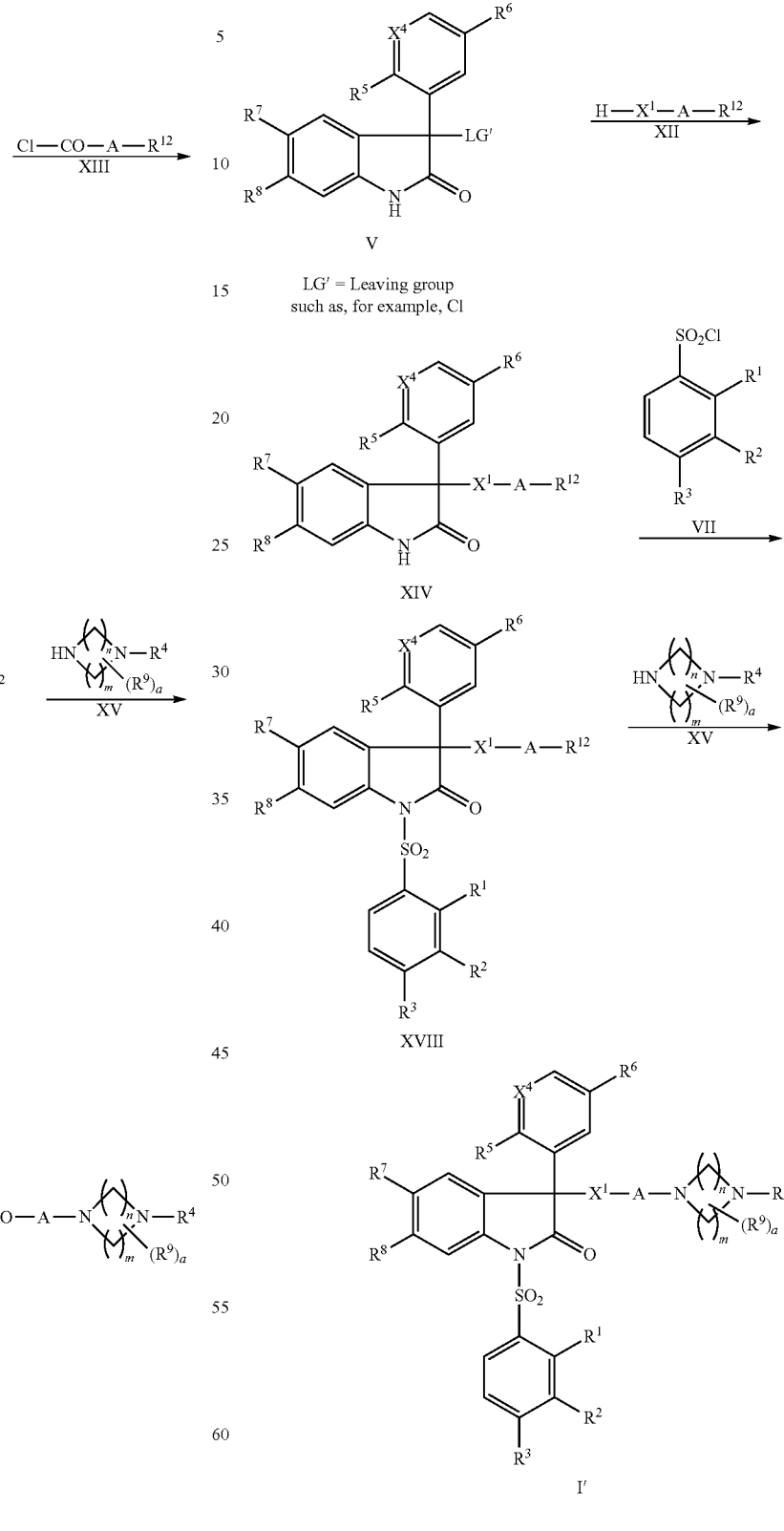
A further aspect of the present invention relates to compounds of the formula XVIII which are employed as intermediate in the synthesis of the compounds I of the invention:

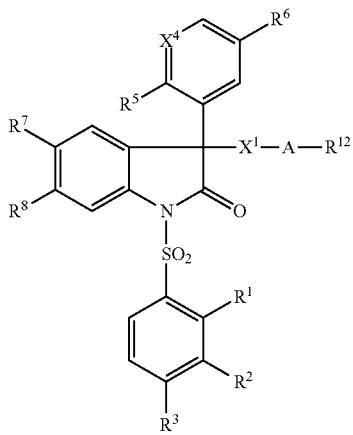

(XVIII)

in which $R^1$, $R^2$, $R^3$, $R^5$, $R^6$, $R^7$, $R^8$, $X^1$, $X^4$ and A are as defined above for compound I; and $R^{12}$ is halogen, CN, $OR^a$ or $NR^bR^c$ in which $R^a$ is H, $C_1$-$C_4$-alkyl, phenyl or benzyl; and $R^b$ and $R^c$ are independently of one another H, $C_1$-$C_4$-alkyl, $C_1$-$C_4$-alkoxy, phenyl or benzyl.

Concerning preferred embodiments of the variables $R^1$, $R^2$, $R^3$, $R^5$, $R^6$, $R^7$, $R^8$, $X^1$, $X^4$ and A, reference is made to the above statements concerning the corresponding variables in compounds I.

Halogen in the definition of $R^{12}$ is preferably iodine, bromine or chlorine and is in particular bromine.

$R^{12}$ is preferably halogen or CN and is more preferably halogen. $R^{12}$ is particularly preferably iodine, bromine or chlorine and is in particular bromine.

A further aspect of the present invention relates to a pharmaceutical composition comprising at least one compound of the general formula I and/or a pharmaceutically acceptable salt or a prodrug thereof as detailed above, and a pharmaceutically acceptable carrier. Suitable carriers depend inter alia on the dosage form of the composition and are known in principle to the skilled worker. Some suitable carriers are described hereinafter.

A further aspect of the present invention relates to the use of compounds of the formula I and/or of pharmaceutically suitable salts or prodrugs thereof for the manufacture of a medicament for the treatment and/or prophylaxis of vasopressin-dependent diseases.

Vasopressin-dependent diseases are those in which the progress of the disease is at least partly dependent on vasopressin, i.e. diseases which show an elevated vasopressin level which may contribute directly or indirectly to the pathological condition. In other words, vasopressin-dependent diseases are those which can be influenced by modulating the vasopressin receptor, for example by administration of a vasopressin receptor ligand (agonist, antagonist, partial antagonist/agonist, inverse agonist etc.).

In a preferred embodiment, the present invention relates to the use of compounds of the invention of the formula I or of pharmaceutically acceptable salts or prodrugs for the manufacture of a medicament for the treatment and/or prophylaxis of diseases selected from diabetes, insulin resistance, nocturnal enuresis, incontinence and diseases in which impairments of blood clotting occur, and/or for delaying micturition. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of pharmaceutically acceptable salts or prodrugs thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness.

The compounds of the invention of the formula I or their pharmaceutically acceptable salts or prodrugs or the pharmaceutical composition of the invention can also be used for the treatment of various vasopressin-dependent complaints which have central nervous causes or alterations in the HPA axis (hypothalamic pituitary adrenal axis), for example for affective disorders such as depressive disorders and bipolar disorders. These include for example dysthymic disorders, phobias, post-traumatic stress disorders, general anxiety disorders, panic disorders, seasonal depression and sleep disorders.

The compounds of the invention of the formula I and their pharmaceutically acceptable salts or prodrugs or the pharmaceutical composition of the invention can likewise be employed for the treatment of anxiety disorders and stress-dependent anxiety disorders, such as, for example, generalized anxiety disorders, phobias, post-traumatic anxiety disorders, panic anxiety disorders, obsessive-compulsive anxiety disorders, acute stress-dependent anxiety disorders and social phobia.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of pharmaceutically acceptable salts or prodrugs thereof for the manufacture of a medicament for the treatment of affective disorders.

In a further preferred embodiment, the present invention relates to the use of compounds of the invention of the formula I or of pharmaceutically acceptable salts or prodrugs thereof for the manufacture of a medicament for the treatment of anxiety disorders and/or stress-dependent anxiety disorders.

In a further preferred embodiment, the present invention relates to the use of compounds of the invention of the formula I or of pharmaceutically acceptable salts or prodrugs thereof for the manufacture of a medicament for the treatment of memory impairments and/or Alzheimer's disease.

In a further preferred embodiment, the present invention relates to the use of compounds of the invention of the formula I or of pharmaceutically acceptable salts or prodrugs thereof for the manufacture of a medicament for the treatment of psychoses and/or psychotic disorders.

In a further preferred embodiment, the present invention relates to the use of compounds of the invention of the formula I or of pharmaceutically acceptable salts or prodrugs thereof for the manufacture of a medicament for the treatment of Cushing's syndrome or other stress-dependent diseases.

In a further preferred embodiment, the present invention relates to the use of compounds of the invention of the formula I or of pharmaceutically acceptable salts or prodrugs thereof for the manufacture of a medicament for the treatment of sleep disorders.

In a further preferred embodiment, the present invention relates to the use of compounds of the invention of the formula I or of pharmaceutically acceptable salts or prodrugs thereof for the manufacture of a medicament for the treatment of depressive disorders. A particular form of depressive disorders are so-called childhood onset mood disorders, i.e. depressive moods having their onset in childhood.

In a further preferred embodiment, the present invention relates to the use of compounds of the invention of the formula I or of pharmaceutically acceptable salts or prodrugs thereof for the manufacture of a medicament for the treatment of vasomotor symptoms and/or thermoregulatory dysfunctions such as, for example, the hot flush symptom.

In a further preferred embodiment, the present invention relates to the use of compounds of the invention of the formula I or of pharmaceutically acceptable salts or prodrugs thereof for the manufacture of a medicament for the treatment and/or prophylaxis of drug or pharmaceutical dependencies and/or dependencies mediated by other factors, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors.

In a further preferred embodiment, the present invention relates to the use of compounds of the invention of the formula I or of pharmaceutically acceptable salts or prodrugs thereof for the manufacture of a medicament for the treatment and/or prophylaxis of schizophrenia and/or psychosis.

A further aspect of the invention relates to a method for the treatment and/or prophylaxis of vasopressin-dependent diseases, in which an effective amount of at least one compound of the invention of the formula I or of at least one pharmaceutically acceptable salt or one prodrug thereof or of a pharmaceutical composition of the invention is administered to a patient.

Concerning the definition of vasopressin-dependent diseases, reference is made to the above statements.

In a preferred embodiment of the invention, the method of the invention serves for the treatment and/or prophylaxis of disorders selected from diabetes, insulin resistance, nocturnal enuresis, incontinence and diseases in which impairments of blood clotting occur, and/or for delaying micturition. Concerning the definition of diabetes, reference is made to the above statements.

In a further preferred embodiment, the method of the invention serves for the treatment and/or prophylaxis of disorders selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastric vasospasm, hepatocirrhosis, gastric and intestinal ulcers, emesis, emesis occurring during chemotherapy, and travel sickness.

In a further preferred embodiment, the method of the invention serves for the treatment and/or prophylaxis of affective disorders.

In a further preferred embodiment, the method of the invention serves for the treatment and/or prophylaxis of anxiety disorders and/or stress-dependent anxiety disorders.

In a further preferred embodiment, the method of the invention serves for the treatment and/or prophylaxis of memory impairments and/or Alzheimer's disease.

In a further preferred embodiment, the method of the invention serves for the treatment and/or prophylaxis of psychoses and/or psychotic disorders.

In a further preferred embodiment, the method of the invention serves for the treatment and/or prophylaxis of Cushing's syndrome.

In a further preferred embodiment, the method of the invention serves for the treatment and/or prophylaxis of sleep disorders in a patient.

In a further preferred embodiment, the method of the invention serves for the treatment and/or prophylaxis of depressive disorders. In the case of depressive disorders, specific mention is also to be made of childhood onset mood disorders, i.e. depressive moods having their onset in childhood.

In a further preferred embodiment, the method of the invention serves for the treatment and/or prophylaxis of vasomotor symptoms and/or thermoregulatory dysfunctions, such as, for example, the hot flush symptom.

In a further preferred embodiment, the method of the invention serves for the treatment and/or prophylaxis of drug or pharmaceutical dependencies and/or dependencies mediated by other factors, for the treatment and/or prophylaxis of stress caused by withdrawal of one or more factors mediating the dependence, and/or for the treatment and/or prophylaxis of stress-induced relapses into drug or pharmaceutical dependencies and/or dependencies mediated by other factors.

In a further preferred embodiment, the method of the invention serves for the treatment and/or prophylaxis of schizophrenia and/or psychosis.

The patient to be treated prophylactically or therapeutically with the method of the invention is preferably a mammal, for example a human or a nonhuman mammal or a nonhuman transgenic mammal. Specifically it is a human.

The compounds of the general formula I, their pharmaceutically acceptable salts and prodrugs as detailed above can be prepared by a skilled worker with knowledge of the technical teaching of the invention in implementing and/or in analogous implementation of process steps known per se.

The compounds I or their prodrugs and/or their pharmaceutically acceptable salts are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I or their prodrugs and/or their pharmaceutically acceptable salts are distinguished by having an improved metabolic stability.

The metabolic stability of a compound can be measured for example by incubating a solution of this compound with liver microsomes from particular species (for example rat, dog or human) and determining the half-life of the compound under these conditions (RS Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-dependent diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

Alternatively, or preferably in addition, the compounds I or their prodrugs and/or their pharmaceutically acceptable salts are distinguished by having an improved pharmacological activity, compared with the oxindole compounds known from the prior art, in patients or relevant animal models which enable prognostic statements for use in the treatment.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention, of a pharmaceutically acceptable salt or of a prodrug thereof and suitable pharmaceutical carriers (drug carriers).

These drug carriers are chosen according to the pharmaceutical form and the desired mode of administration and are known in principle to the skilled worker.

The compounds of the invention of the formula I or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, salt or a prodrug thereof.

The invention is explained in more detail below by means of examples, but the examples are not to be understood to be restrictive.

The compounds of the invention can be prepared by various synthetic routes. The compounds mentioned in the following synthesis examples were prepared in analogy to the procedures outlined in reaction schemes 1 to 5. Synthesis schemes 1 to 5 are, however, to be understood only as exemplary and not restrictive; other routes are also possible for the synthesis.

EXPERIMENTAL SECTION

Abbreviations used:
DIPEA: Diisopropylethylamine
DMSO: Dimethyl sulfoxide
THF: Tetrahydrofuran
TFA: Trifluoroacetic acid
p: pseudo (for example pt pseudo triplet)
b: broad (for example bs broad singlet)
s: singlet
d: doublet
t: triplet
m: multiplet
dd: doublet of doublets
dt: doublet of triplets
tt: triplet of triplets
I. Preparation of the Compounds I The compounds of the formula I were synthesized in analogy to the preparation processes described in synthesis schemes 1 to 5. The compounds can be purified by crystallization and/or preparative HPLC(RP, eluent acetonitrile/water, 0.1% TFA or 0.1% acetic acid). The compounds I then result where appropriate as trifluoroacetic acid salt, bis(trifluoroacetic acid) salt or acetic acid salt.

I.1 Preparation of the Compounds I in which $X^1$ is —O—C(=O)—

EXAMPLE 1

1-(2,4-Dimethoxyphenylsulfonyl)-3-(2-ethoxypyridin-3-yl)-5-iodo-2-oxo-2,3-dihydro-1H-indol-3-yl-4-(4-methylpiperazin-1-yl)benzoate 1.1 3-(2-Ethoxypyridin-3-yl)-5-iodo-2-oxo-2,3-dihydro-1H-indol-3-yl 4-(4-methylpiperazin-1-yl)benzoate ESI-MS: 599.10 [m+H]$^+$
$^1$H-NMR (500 MHz, d$_6$-DMSO): δ [ppm] 10.40 (s, 1H); 8.30 (d, 1H); 8.20 (d, 1H); 7.90 (d, 2H); 7.60 (d, 1H); 7.35 (s, 1H); 7.20 (m, 1H); 7.05 (d, 2H); 6.75 (d, 1H); 4.15 (m, 2H); 3.35 (bs, 4H); 2.45 (bs, 4H); 2.20 (s, 3H); 1.05 (t, 3H).

1.2 1-(2,4-Dimethoxyphenylsulfonyl)-3-(2-ethoxypyridin-3-yl)-5-iodo-2-oxo-2,3-dihydro-1H-indol-3-yl 4-(4-methylpiperazin-1-yl)benzoate ESI-MS: 799.20 [m+H]$^+$
$^1$H-NMR (500 MHz, d$_6$-DMSO): δ [ppm] 8.35 (d, 1H); 8.20 (d, 1H); 7.90 (d, 1H); 7.80 (d, 1H); 7.75 (d, 2H); 7.65 (d, 1H); 7.45 (s, 1H); 7.20 (m, 1H); 7.00 (d, 2H); 6.75 (d, 1H); 6.70 (d, 1H); 4.15 (m, 2H); 3.90 (s, 3H); 3.65 (s, 3H); 3.35 (bs, 4H); 2.45 (bs, 4H); 2.20 (s, 3H); 1.05 (t, 3H).

EXAMPLE 2

5-Cyano-3-(2-ethoxypyridin-3-yl)-1-(4-methoxyphenylsulfonyl)-2-oxo-2,3-dihydro-1H-indol-3-yl-4-(4-methylpiperazin-1-yl)benzoate 2.1 5-Cyano-3-(2-ethoxypyridin-3-yl)-2-oxo-2,3-dihydro-1H-indol-3-yl 4-(4-methylpiperazin-1-yl)benzoate ESI-MS: 498.20 [m+H]$^+$ 2.2 5-Cyano-3-(2-ethoxypyridin-3-yl)-1-(4-methoxyphenylsulfonyl)-2-oxo-2,3-dihydro-1H-indol-3-yl 4-(4-methylpiperazin-1-yl)benzoate ESI-MS: 668.20 [m+H]$^+$
$^1$H-NMR (500 MHz, d$_6$-DMSO): δ [ppm] 8.45 (d, 1H); 8.20 (m, 1H); 8.05 (m, 3H); 7.95 (d, 1H); 7.75 (m, 1H); 7.70 (d, 2H); 7.25 (m, 3H); 6.95 (d, 2H); 4.10 (m, 1H); 4.00 (m, 1H); 3.90 (s, 3H); 3.35 (bs, 4H); 2.45 (bs, 4H); 2.20 (s, 3H); 0.95 (t, 3H).

EXAMPLE 3

5-Cyano-1-(2,4-dimethoxyphenylsulfonyl)-3-(2-ethoxypyridin-3-yl)-2-oxo-2,3-dihydro-1H-indol-3-yl 4-(4-methylpiperazin-1-yl)benzoate ESI-MS: 698.25 [m+H]$^+$
$^1$H-NMR (500 MHz, d$_6$-DMSO): δ [ppm] 8.40 (d, 1H); 8.20 (m, 1H); 8.00 (d, 1H); 7.95 (m, 1H); 7.85 (d, 1H); 7.70 (m, 3H); 7.20 (m, 1H); 6.95 (d, 2H); 6.75 (d, 1H); 6.65 (dd, 1H); 4.10 (m, 2H); 3.85 (s, 3H); 3.55 (s, 3H); 3.30 (bs, 4H); 2.40 (bs, 4H); 2.15 (s, 3H); 1.00 (t, 3H).

I.2 Preparation of the Compounds I in which $X^1$ is —NH—C(=O)—

EXAMPLE 4

N-[5-Cyano-3-(2-ethoxypyridin-3-yl)-1-(4-methoxyphenylsulfonyl)-2-oxo-2,3-dihydro-1H-indol-3-yl]-4-(4-methylpiperazin-1-yl)benzamide 4.1 3-Amino-3-(2-ethoxypyridin-3-yl)-1-(4-methoxyphenylsulfonyl)-2-oxo-2,3-dihydro-1H-indole-5-carbonitrile ESI-MS: 465.10 [m+H]$^+$ 4.2 N-[5-Cyano-3-(2-ethoxypyridin-3-yl)-1-(4-methoxyphenylsulfonyl)-2-oxo-2,3-dihydro-1H-indol-3-yl]benzamide ESI-MS: 569.15 [m+H]$^+$
$^1$H-NMR (500 MHz, d$_6$-DMSO): δ [ppm] 9.65 (s, 1H); 8.20 (m, 1H); 8.05 (d, 2H); 8.00 (m, 2H); 7.90 (d, 1H); 7.80 (m, 3H); 7.55 (m, 1H); 7.45 (m, 2H); 7.20 (d, 1H); 7.10 (m, 1H); 4.20 (m, 1H); 4.15 (m, 1H); 3.90 (s, 3H); 1.05 (t, 3H).

4.3 4-Bromo-N-[5-cyano-3-(2-ethoxypyridin-3-yl)-1-(4-methoxyphenylsulfonyl)-2-oxo-2,3-dihydro-1H-indol-3-yl]benzamide ESI-MS: 647.05/649.05 [m+H]$^+$
$^1$H-NMR (500 MHz, d$_6$-DMSO): δ [ppm] 9.75 (s, 1H); 8.20 (m, 1H); 8.05 (d, 2H); 8.00 (m, 2H); 7.85 (d, 1H); 7.75 (s, 1H); 7.70 (m, 4H); 7.20 (d, 1H); 7.10 (m, 1H); 4.20 (m, 1H); 4.15 (m, 1H); 3.90 (s, 3H); 1.05 (t, 3H).

4.4 N-[5-Cyano-3-(2-ethoxypyridin-3-yl)-1-(4-methoxyphenylsulfonyl)-2-oxo-2,3-dihydro-1H-indol-3-yl]-4-(4-methylpiperazin-1-yl)benzamide ESI-MS: 667.25 [m+H]$^+$
$^1$H-NMR (500 MHz, d$_6$-DMSO): δ [ppm] 9.30 (s, 1H); 8.20 (m, 1H); 8.05 (m, 2H); 7.95 (m, 2H); 7.85 (d, 1H); 7.75 (s, 1H); 7.65 (d, 1H); 7.20 (d, 2H); 7.10 (m, 1H); 6.95 (d, 2H); 4.15 (m, 1H); 4.10 (m, 1H); 3.90 (s, 3H); 3.25 (m, 4H); 2.45 (m, 4H); 2.25 (s, 3H); 1.05 (t, 3H).

EXAMPLE 5

N-[5-Cyano-3-(2-ethoxypyridin-3-yl)-1-(4-methoxyphenylsulfonyl)-2-oxo-2,3-dihydro-1H-indol-3-yl]-4-(4-ethylpiperazin-1-yl)benzamide ESI-MS: 681.30 [m+H]$^+$
$^1$H-NMR (500 MHz, d$_6$-DMSO): δ [ppm] 9.30 (s, 1H); 8.20 (m, 1H); 8.05 (d, 2H); 7.95 (m, 2H); 7.85 (d, 1H); 7.75 (s, 1H); 7.65 (d, 1H); 7.20 (d, 2H); 7.10 (m, 1H); 6.95 (d, 2H); 4.15 (m, 1H); 4.10 (m, 1H); 3.90 (s, 3H); 3.30 (bs, 4H); 2.50 (bs, 4H); 2.40 (bs, 2H); 1.05 (m, 6H).

EXAMPLE 6

N-[5-Cyano-1-(2,4-dimethoxyphenylsulfonyl)-3-(2-ethoxypyridin-3-yl)-2-oxo-2,3-dihydro-1H-indol-3-yl]-4-(4-methylpiperazin-1-yl)benzamide 6.1 3-Amino-1-(2,4-dimethoxyphenylsulfonyl)-3-(2-ethoxypyridin-3-yl)-2-oxo-2,3-dihydro-1H-indole-5-carbonitrile

ESI-MS: 495.10 [M+H]$^+$ 6.2 N-[5-Cyano-1-(2,4-dimethoxyphenylsulfonyl)-3-(2-ethoxypyridin-3-yl)-2-oxo-2,3-dihydro-1H-indol-3-yl]-4-(4-methylpiperazin-1-yl)benzamide ESI-MS: 697.30 [m+H]$^+$
$^1$H-NMR (500 MHz, d$_6$-DMSO): δ [ppm] 9.35 (s, 1H); 8.25 (m, 1H); 8.05 (m, 2H); 7.95 (d, 1H); 7.90 (s, 1H); 7.75 (m, 3H); 7.15 (m, 1H); 7.00 (d, 2H); 6.80 (m, 2H); 4.35 (m, 2H); 3.95 (s, 3H); 3.60 (s, 3H); 3.35 (m, 4H); 2.50 (bs, 4H); 2.30 (s, 3H); 1.20 (t, 3H).

EXAMPLE 7

N-[5-Cyano-1-(2,4-dimethoxyphenylsulfonyl)-3-(2-ethoxypyridin-3-yl)-2-oxo-2,3-dihydro-1H-indol-3-yl]-4-(4-ethylpiperazin-1-yl)benzamide ESI-MS: 711.25 [m+H]$^+$
$^1$H-NMR (500 MHz, d$_6$-DMSO): δ [ppm] 9.30 (s, 1H); 8.20 (m, 1H); 7.95 (m, 2H); 7.85 (d, 1H); 7.80 (s, 1H); 7.70 (m, 3H); 7.05 (m, 1H); 6.95 (d, 2H); 6.75 (m, 2H); 4.25 (m, 2H); 3.90 (s, 3H); 3.50 (s, 3H); 3.30 (bs, 4H); 2.50 (bs, 4H); 2.35 (m, 2H); 1.15 (t, 3H); 1.05 (t, 3H).

EXAMPLE 8

N-[1-[4-(2,2-Difluoroethoxy)phenylsulfonyl]-3-(2-ethoxypyridin-3-yl)-5-iodo-2-oxo-2,3-dihydro-1H-indol-3-yl]-4-(4-methylpiperazin-1-yl)benzamide ESI-MS: 818.20 [M+H]$^+$
$^1$H-NMR (500 MHz, d$_6$-DMSO): δ [ppm] 9.25 (s, 1H); 8.20 (m, 1H); 8.05 (d, 2H); 7.75 (d, 1H); 7.70 (m, 2H); 7.65 (d, 2H); 7.60 (d, 1H); 7.30 (d, 2H); 7.05 (m, 1H); 6.95 (d, 2H); 6.45 (t, J=70 Hz, 1H); 4.50 (m, 2H); 4.20 (m, 2H); 3.30 (m, 4H); 2.50 (m, 4H); 2.25 (m, 3H); 1.15 (t, 3H).

I.3 Preparation of the Compounds I in which X$^1$ is —NH—CH$_2$—

I.3.1 Compounds I in which X$^1$ is —NH—CH$_2$— and A is 1,4-phenylene

EXAMPLE 9

1-(2,4-Dimethoxyphenylsulfonyl)-3-(2-ethoxypyridin-3-yl)-5-iodo-3-[4-(4-methylpiperazin-1-yl)benzylamino]-1,3-dihydroindol-2-one 9.1 3-(2-Ethoxypyridin-3-yl)-5-iodo-3-[4-(4-methylpiperazin-1-yl)benzylamino]-1,3-dihydroindol-2-one ESI-MS: 584.10 [m+H]$^+$ 9.2 1-(2,4-Dimethoxyphenylsulfonyl)-3-(2-ethoxypyridin-3-yl)-5-iodo-3-[4-(4-methylpiperazin-1-yl)benzylamino]-1,3-dihydroindol-2-one ESI-MS: 784.20 [m+H]$^+$
$^1$H-NMR (500 MHz, d$_6$-DMSO): δ [ppm] 8.20 (m, 1H); 8.15 (d, 1H); 8.10 (m, 1H); 7.80 (d, 1H); 7.70 (d, 1H); 7.25 (s, 1H); 6.90 (m, 3H); 6.80 (d, 2H); 6.65 (d, 1H); 6.35 (s, 1H); 4.25 (m, 1H); 4.20 (m, 1H); 3.85 (s, 3H); 3.55 (s, 3H); 3.20 (s, 4H); 3.05 (m, 1H); 2.90 (m, 1H); 2.55 (s, 4H); 2.35 (s, 3H); 2.05 (m, 1H); 1.20 (t, 3H).

EXAMPLE 10

1-(2,4-Dimethoxyphenylsulfonyl)-3-(2-ethoxypyridin-3-yl)-5-iodo-3-(4-piperazin-1-yl-benzylamino)-1,3-dihydroindol-2-one as acetic acid salt ESI-MS: 770.15 [m+H]$^+$

EXAMPLE 11

5-Chloro-3-(2-ethoxypyridin-3-yl)-1-(4-methoxyphenylsulfonyl)-3-[4-(4-methylpiperazin-1-yl)-benzylamino]-1,3-dihydroindol-2-one 11.1 5-Chloro-3-(2-ethoxypyridin-3-yl)-3-[4-(4-methylpiperazin-1-yl)benzylamino]-1,3-dihydroindol-2-one ESI-MS: 492.25 [m+H]$^+$ 11.2 5-Chloro-3-(2-ethoxypyridin-3-yl)-1-(4-methoxyphenylsulfonyl)-3-[4-(4-methylpiperazin-1-yl)benzylamino]-1,3-dihydroindol-2-one ESI-MS: 662.25 [m+H]$^+$
$^1$H-NMR (500 MHz, CDCl$_3$): δ [ppm] 8.15 (m, 1H); 8.10 (d, 2H); 8.05 (m, 1H); 7.95 (d, 1H); 7.35 (d, 1H); 7.00 (d, 2H); 6.90 (m, 4H); 6.80 (d, 2H); 4.10 (m, 1H); 4.05 (m, 1H); 3.85 (s, 3H); 3.15 (m, 4H); 2.95 (m, 1H); 2.70 (m, 1H); 2.55 (m, 4H); 2.35 (s, 3H); 2.05 (m, 1H); 1.05 (t, 3H).

EXAMPLE 12

5-Chloro-3-(2-ethoxypyridin-3-yl)-6-fluoro-1-(4-methoxyphenylsulfonyl)-3-[4-(4-methylpiperazin-1-yl)benzylamino]-1,3-dihydroindol-2-one 12.1 5-Chloro-3-(2-ethoxypyridin-3-yl)-6-fluoro-3-[4-(4-methylpiperazin-1-yl)-benzylamino]-1,3-dihydroindol-2-one ESI-MS: 510.20 [m+H]$^+$ 12.2 5-Chloro-3-(2-ethoxypyridin-3-yl)-6-fluoro-1-(4-methoxyphenylsulfonyl)-3-[4-(4-methylpiperazin-1-yl)benzylamino]-1,3-dihydroindol-2-one ESI-MS: 680.20 [m+H]$^+$
$^1$H-NMR (500 MHz, CDCl$_3$): δ [ppm] 8.15 (m, 1H); 8.10 (d, 2H); 8.05 (m, 1H); 7.90 (d, 1H); 7.00 (d, 2H); 6.90 (m, 4H); 6.80 (d, 2H); 4.10 (m, 2H); 3.85 (s, 3H); 3.15 (m, 4H); 2.90 (m, 1H); 2.70 (m, 1H); 2.55 (m, 4H); 2.35 (s, 3H); 2.10 (m, 1H); 1.10 (t, 3H).

EXAMPLE 13

6-Chloro-3-(2-ethoxypyridin-3-yl)-5-fluoro-1-(4-methoxyphenylsulfonyl)-3-[4-(4-methylpiperazin-1-yl)benzylamino]-1,3-dihydroindol-2-one 13.1 6-Chloro-3-(2-ethoxypyridin-3-yl)-5-fluoro-3-[4-(4-methylpiperazin-1-yl)-benzylamino]-1,3-dihydroindol-2-one ESI-MS: 510.25 [m+H]$^+$

13.2 6-Chloro-3-(2-ethoxypyridin-3-yl)-5-fluoro-1-(4-methoxyphenylsulfonyl)-3-[4-(4-methylpiperazin-1-yl)benzylamino]-1,3-dihydroindol-2-one ESI-MS: 680.20 [m+H]$^+$
$^1$H-NMR (400 MHz, CDCl$_3$): δ [ppm] 8.20-8.05 (m, 5H); 7.00 (d, 2H); 6.90 (m, 3H); 6.80 (d, 2H); 6.75 (d, 1H); 4.10 (m, 2H); 3.85 (s, 3H); 3.20 (m, 4H); 2.90 (m, 1H); 2.70 (m, 1H); 2.60 (m, 4H); 2.35 (s, 3H); 2.10 (m, 1H); 1.10 (t, 3H).

EXAMPLE 14

5,6-Difluoro-3-(2-ethoxypyridin-3-yl)-1-(4-methoxyphenylsulfonyl)-3-[4-(4-methylpiperazin-1-yl)benzylamino]-1,3-dihydroindol-2-one ESI-MS: 664.25 [M+H]$^+$
$^1$H-NMR (500 MHz, CDCl$_3$): δ [ppm] 8.15 (d, 1H); 8.10 (d, 2H); 8.05 (m, 1H); 7.95 (m, 1H); 7.00 (d, 2H); 6.90 (m, 3H); 6.80 (m, 3H); 4.15 (m, 1H); 4.10 (m, 1H); 3.85 (s, 3H); 3.15 (m, 4H); 2.90 (m, 1H); 2.70 (m, 1H); 2.60 (m, 4H); 2.35 (s, 3H); 2.10 (m, 1H); 1.10 (t, 3H).

EXAMPLE 15

3-(2-Ethoxypyridin-3-yl)-5-fluoro-1-(4-methoxyphenylsulfonyl)-3-[4-(4-methylpiperazin-1-yl)benzylamino]-1,3-dihydroindol-2-one ESI-MS: 646.25 [m+H]$^+$

EXAMPLE 16

3-(2-Ethoxypyridin-3-yl)-1-(4-methoxyphenylsulfonyl)-3-[4-(4-methylpiperazin-1-yl)-benzylamino]-2-oxo-2,3-dihydro-1H-indole-5-carbonitrile

16.1 3-(2-Ethoxypyridin-3-yl)-3-[4-(4-methylpiperazin-1-yl)benzylamino]-2-oxo-2,3-dihydro-1H-indole-5-carbonitrile ESI-MS: 483.25 [m+H]$^+$
$^1$H-NMR (500 MHz, d$_6$-DMSO): δ [ppm] 8.25 (d, 1H); 8.10 (m, 1H); 7.65 (d, 1H); 7.15 (m, 3H); 7.10 (m, 1H); 7.05 (d, 1H); 6.90 (d, 2H); 4.05 (m, 3H); 3.50-3.15 (m, 6H); 3.00 (bs, 4H); 2.60 (s, 3); 0.95 (t, 3H).

16.2 3-(2-Ethoxypyridin-3-yl)-1-(4-methoxyphenylsulfonyl)-3-[4-(4-methylpiperazin-1-yl)-benzylamino]-2-oxo-2,3-dihydro-1H-indole-5-carbonitrile ESI-MS: 653.20 [m+H]$^+$
$^1$H-NMR (500 MHz, d$_6$-DMSO): δ [ppm] 8.30 (d, 1H); 8.20 (m, 3H); 8.15 (d, 1H); 7.95 (d, 1H); 7.40 (s, 1H); 7.30 (d, 2H); 7.20 (m, 1H); 6.95 (d, 2H); 6.85 (d, 2H); 4.05 (m, 1H); 3.90 (m, 4H); 3.80 (m, 1H); 3.15 (m, 4H); 3.00 (m, 1H); 2.95 (m, 1H); 2.50 (m, 4H); 2.30 (s, 3H); 0.90 (t, 3H).

EXAMPLE 17

1-(2,4-Dimethoxyphenylsulfonyl)-3-(2-ethoxypyridin-3-yl)-3-[4-(4-methylpiperazin-1-yl)-benzylamino]-2-oxo-2,3-dihydro-1H-indole-5-carbonitrile ESI-MS: 683.25 [M+H]$^+$
$^1$H-NMR (500 MHz, d$_6$-DMSO): δ [ppm] 8.20 (d, 1H); 8.05 (m, 3H); 7.70 (d, 1H); 7.20 (s, 1H); 6.95 (m, 1H); 6.80 (d, 2H); 6.75 (d, 2H); 6.65 (d, 1H); 6.50 (s, 1H); 4.05 (m, 2H); 3.80 (s, 3H); 3.50 (s, 3H); 3.05 (m, 4H); 2.90 (m, 1H); 2.80 (m, 1H); 2.50 (m, 4H); 2.25 (bs, 3H); 1.05 (t, 3H).

EXAMPLE 18

3-(2-Ethoxypyridin-3-yl)-1-(4-methoxy-2-trifluoromethoxyphenylsulfonyl)-3-[4-(4-methylpiperazin-1-yl)benzylamino]-2-oxo-2,3-dihydro-1H-indole-5-carbonitrile ESI-MS: 737.25 [m+H]$^+$
$^1$H-NMR (500 MHz, d$_6$-DMSO): δ [ppm] 8.35 (d, 1H); 8.15 (m, 2H); 8.10 (m, 1H); 7.70 (d, 1H); 7.25 (m, 1H); 7.00-6.90 (m, 4H); 6.85 (m, 3H); 4.25 (m, 2H); 3.90 (s, 3H); 3.20 (m, 4H); 3.05 (m, 1H); 2.95 (m, 1H); 2.55 (m, 4H); 2.35 (s, 3H); 2.10 (m, 1H); 1.10 (t, 3H).

EXAMPLE 19

3-(2-Ethoxypyridin-3-yl)-3-[4-(4-methylpiperazin-1-yl)benzylamino]-2-oxo-1-(4-trifluoromethoxyphenylsulfonyl)-2,3-dihydro-1H-indole-5-carbonitrile ESI-MS: 707.20 [m+H]$^+$
$^1$H-NMR (500 MHz, CDCl$_3$): δ [ppm] 8.30 (d, 2H); 8.20 (m, 1H); 8.10 (m, 2H); 7.70 (d, 1H); 7.40 (d, 2H); 7.25 (s, 1H); 6.95 (m, 1H); 6.90 (d, 2H); 6.80 (d, 2H); 4.15 (m, 2H); 4.00 (m, 1H); 3.20 (m, 4H); 2.95 (m, 1H); 2.85 (m, 1H); 2.55 (m, 4H); 2.35 (s, 3H); 2.15 (m, 1H); 0.95 (t, 3H).

EXAMPLE 20

3-(2-Ethoxypyridin-3-yl)-3-[4-(4-methylpiperazin-1-yl)benzylamino]-2-oxo-1-[4-(2,2,2-trifluoroethoxy)phenylsulfonyl]-2,3-dihydro-1H-indole-5-carbonitrile ESI-MS: 721.20 [m+H]$^+$
$^1$H-NMR (500 MHz, CDCl$_3$): δ [ppm] 8.20 (m, 3H); 8.15 (d, 1H); 8.10 (m, 1H); 7.65 (d, 1H); 7.25 (s, 1H); 7.10 (d, 2H); 6.95 (m, 1H); 6.85 (d, 2H); 6.80 (d, 2H); 4.35 (m, 2H); 4.15 (m, 1H); 4.05 (m, 1H); 3.15 (m, 4H); 2.90 (m, 1H); 2.70 (m, 1H); 2.55 (m, 4H); 2.35 (s, 3H); 2.10 (m, 1H); 1.05 (t, 3H).

EXAMPLE 21

1-[4-(2,2-Difluoroethoxy)phenylsulfonyl]-3-(2-ethoxypyridin-3-yl)-3-[4-(4-methylpiperazin-1-yl)benzylamino]-2-oxo-2,3-dihydro-1H-indole-5-carbonitrile ESI-MS: 703.20 [m+H]$^+$
$^1$H-NMR (500 MHz, CDCl$_3$): δ [ppm] 8.15 (m, 4H); 8.10 (d, 1H); 7.65 (d, 1H); 7.25 (s, 1H); 7.05 (d, 2H); 6.95 (m, 1H); 6.85 (d, 2H); 6.80 (d, 2H); 6.05 (t, J=70 Hz, 1H); 4.25-4.00 (m, 4H); 3.15 (m, 4H); 2.85 (m, 1H); 2.70 (m, 1H); 2.55 (m, 4H); 2.35 (s, 3H); 2.10 (m, 1H); 1.05 (t, 3H).

EXAMPLE 22

3-(2-Ethoxypyridin-3-yl)-1-[4-(2-fluoroethoxy)phenylsulfonyl]-3-[4-(4-methylpiperazin-1-yl)-benzylamino]-2-oxo-2,3-dihydro-1H-indole-5-carbonitrile ESI-MS: 685.20 [m+H]$^+$
$^1$H-NMR (500 MHz, CDCl$_3$): δ [ppm] 8.20 (d, 1H); 8.15 (m, 3H); 8.10 (m, 1H); 7.65 (d, 1H); 7.20 (s, 1H); 7.05 (d, 2H); 6.95 (m, 1H); 6.85 (d, 2H); 6.80 (d, 2H); 4.80 (t, 1H); 4.70 (t, 1H); 4.25 (m, 1H); 4.20 (m, 1H); 4.15 (m, 1H); 4.05 (m, 1H); 3.15 (m, 4H); 2.90 (m, 1H); 2.75 (m, 1H); 2.55 (m, 4H); 2.35 (s, 3H); 2.10 (m, 1H); 1.05 (t, 3H).

EXAMPLE 23

1-(4-Difluoromethoxyphenylsulfonyl)-3-(2-ethoxy-pyridin-3-yl)-3-[4-(4-methylpiperazin-1-yl)benzylamino]-2-oxo-2,3-dihydro-1H-indole-5-carbonitrile ESI-MS: 689.20 [m+H]$^+$
$^1$H-NMR (500 MHz, CDCl$_3$): δ [ppm] 8.20 (m, 3H); 8.10 (m, 2H); 7.70 (d, 1H); 7.30 (d, 2H); 7.25 (s, 1H); 6.95 (m, 1H); 6.85 (d, 2H); 6.80 (d, 2H); 6.55 (t, J=70 Hz, 1H); 4.15 (m, 1H); 4.05 (m, 1H); 3.20 (m, 4H); 2.95 (m, 1H); 2.75 (m, 1H); 2.55 (m, 4H); 2.35 (s, 3H); 2.15 (m, 1H); 1.00 (t, 3H).

EXAMPLE 24

3-(2-Ethoxypyridin-3-yl)-1-(2-methoxyphenylsulfonyl)-3-[4-(4-methylpiperazin-1-yl)-benzylamino]-2-oxo-2,3-dihydro-1H-indole-5-carbonitrile ESI-MS: 653.20 [m+H]$^+$
$^1$H-NMR (500 MHz, CDCl$_3$): δ [ppm] 8.30 (d, 1H); 8.20 (m, 2H); 8.10 (m, 1H); 7.70 (d, 1H); 7.65 (t, 1H); 7.30 (s, 1H); 7.20 (d, 1H); 6.95 (m, 2H); 6.85 (d, 2H); 6.80 (d, 2H); 4.25 (m, 1H); 4.20 (m, 1H); 3.55 (s, 3H); 3.20 (m, 4H); 3.00 (m, 1H); 2.85 (m, 1H); 2.55 (m, 4H); 2.35 (s, 3H); 2.10 (m, 1H); 1.20 (t, 3H).

EXAMPLE 25

3-(2-Ethoxypyridin-3-yl)-1-(3-methoxyphenylsulfonyl)-3-[4-(4-methylpiperazin-1-yl)-benzylamino]-2-oxo-2,3-dihydro-1H-indole-5-carbonitrile ESI-MS: 653.20 [m+H]$^+$
$^1$H-NMR (500 MHz, CDCl$_3$): δ [ppm] 8.20 (m, 1H); 8.15 (d, 1H); 8.10 (m, 1H); 7.75 (m, 2H); 7.65 (m, 1H); 7.45 (t, 1H); 7.20 (m, 2H); 6.95 (m, 1H); 6.90 (d, 2H); 6.80 (d, 2H); 4.15 (m, 1H); 4.05 (m, 1H); 3.85 (s, 3H); 3.20 (m, 4H); 2.90 (m, 1H); 2.85 (m, 1H); 2.55 (m, 4H); 2.35 (s, 3H); 2.15 (m, 1H); 1.05 (t, 3H).

EXAMPLE 26

1-(4-Chlorophenylsulfonyl)-3-(2-ethoxypyridin-3-yl)-3-[4-(4-methylpiperazin-1-yl)-benzylamino]-2-oxo-2,3-dihydro-1H-indole-5-carbonitrile ESI-MS: 657.20 [m+H]$^+$
$^1$H-NMR (500 MHz, CDCl$_3$): δ [ppm] 8.20 (d, 1H); 8.15 (m, 4H); 7.70 (d, 1H); 7.55 (d, 2H); 7.25 (s, 1H); 6.95 (m, 1H); 6.85 (d, 2H); 6.80 (d, 2H); 4.10 (m, 1H); 4.05 (m, 1H); 3.20 (m, 4H); 2.95 (m, 1H); 2.75 (m, 1H); 2.55 (m, 4H); 2.35 (s, 3H); 2.10 (m, 1H); 1.05 (t, 3H).

EXAMPLE 27

1-Phenylsulfonyl-3-(2-ethoxypyridin-3-yl)-3-[4-(4-methylpiperazin-1-yl)benzylamino]-2-oxo-2,3-dihydro-1H-indole-5-carbonitrile ESI-MS: 623.25 [m+H]$^+$
$^1$H-NMR (500 MHz, CDCl$_3$): δ [ppm] 8.20 (m, 3H); 8.15 (d, 1H); 8.10 (m, 1H); 7.70 (m, 2H); 7.60 (m, 2H); 7.20 (s, 1H); 6.85 (d, 2H); 6.80 (d, 2H); 4.10 (m, 1H); 4.00 (m, 1H); 3.20 (m, 4H); 2.90 (m, 1H); 2.75 (m, 1H); 2.55 (m, 4H); 2.35 (s, 3H); 2.15 (m, 1H); 1.00 (t, 3H).

EXAMPLE 28

1-(4-Cyanophenylsulfonyl)-3-(2-ethoxypyridin-3-yl)-3-[4-(4-methylpiperazin-1-yl)-benzylamino]-2-oxo-2,3-dihydro-1H-indole-5-carbonitrile ESI-MS: 648.25 [m+H]$^+$
$^1$H-NMR (500 MHz, d$_6$-DMSO): δ [ppm] 8.35 (m, 2H); 8.25 (m, 3H); 8.15 (m, 1H); 8.05 (d, 1H); 7.90 (d, 1H); 7.35 (s, 1H); 7.15 (m, 1H); 6.90 (d, 2H); 6.80 (d, 2H); 3.95 (m, 1H); 3.80 (m, 2H); 3.10 (m, 4H); 3.00 (m, 1H); 2.95 (m, 1H); 2.45 (m, 4H); 2.20 (s, 3H); 0.80 (t, 3H).

EXAMPLE 29

1-(2,4-Dimethoxyphenylsulfonyl)-3-(2-ethoxypyridin-3-yl)-2-oxo-3-(4-piperazin-1-yl-benzylamino)-2,3-dihydro-1H-indole-5-carbonitrile as hydrochloride 29.1 tert-Butyl 4-(4-{[5-cyano-3-(2-ethoxypyridin-3-yl)-2-oxo-2,3-dihydro-1H-indol-3-ylamino]methyl}phenyl)piperazine-1-carboxylate

ESI-MS: 569.30 [M+H]$^+$ 29.2 tert-Butyl 4-(4-{[5-cyano-1-(2,4-dimethoxyphenylsulfonyl)-3-(2-ethoxypyridin-3-yl)-2-oxo-2,3-dihydro-1H-indol-3-ylamino]methyl}phenyl)piperazine-1-carboxylate 29.3 tert-Butyl 4-(4-{[5-cyano-3-(2-ethoxypyridin-3-yl)-1-(4-methoxyphenylsulfonyl)-2-oxo-2,3-dihydro-1H-indol-3-ylamino]methyl}phenyl)piperazine-1-carboxylate ESI-MS: 639.20 [M-Boc+H]$^+$
$^1$H-NMR (400 MHz, d$_6$-DMSO): δ [ppm] 8.25 (d, 1H); 8.10 (m, 3H); 8.05 (d, 1H); 7.90 (d, 1H); 7.30 (s, 1H); 7.25 (d, 2H); 7.10 (m, 1H); 6.90 (d, 2H); 6.80 (d, 2H); 3.95 (m, 1H); 3.85 (s, 3H); 3.80 (m, 1H); 3.75 (m, 1H); 3.45 (m, 4H); 3.05 (m, 4H); 2.95 (m, 1H); 2.90 (m, 1H); 1.40 (s, 9H); 0.80 (t, 3H).

29.4 1-(2,4-Dimethoxyphenylsulfonyl)-3-(2-ethoxy-pyridin-3-yl)-2-oxo-3-(4-piperazin-1-yl-benzylamino)-2,3-dihydro-1H-indole-5-carbonitrile as hydrochloride ESI-MS: 669.25 [m+H]$^+$
$^1$H-NMR (500 MHz, d$_6$-DMSO): δ [ppm] 8.25 (d, 1H); 8.10 (m, 1H); 8.05 (d, 2H); 7.95 (d, 1H); 7.45 (s, 1H); 7.10 (m, 1H); 6.95 (d, 2H); 6.85 (d, 2H); 6.80 (d, 1H); 6.75 (s, 1H); 4.05 (m, 2H); 3.85 (s, 3H); 3.65 (m, 1H); 3.55 (s, 3H); 3.20 (bs, 4H); 3.05 (bs, 4H); 2.95 (m, 2H); 0.95 (t, 3H).

EXAMPLE 30

3-(2-Ethoxypyridin-3-yl)-1-(4-methoxyphenylsulfonyl)-2-oxo-3-(4-piperazin-1-yl-benzylamino)-2,3-dihydro-1H-indole-5-carbonitrile ESI-MS: 639.30 [m+H]$^+$
$^1$H-NMR (500 MHz, d$_6$-DMSO): δ [ppm] 8.25 (d, 1H); 8.10 (m, 3H); 8.05 (d, 1H); 7.90 (d, 1H); 7.35 (s, 1H); 7.25 (d, 2H); 7.10 (m, 1H); 6.90 (d, 2H); 6.80 (d, 1H); 3.95 (m, 1H); 3.85 (s, 3H); 3.80 (m, 1H); 3.75 (m, 1H); 3.05 (bs, 4H); 2.95 (m, 6H); 0.80 (t, 3H).

EXAMPLE 31

3-(2-Ethoxypyridin-3-yl)-3-[4-(4-ethylpiperazin-1-yl)benzylamino]-1-(4-methoxy-phenylsulfonyl)-2-oxo-2,3-dihydro-1H-indole-5-carbonitrile ESI-MS: 667.20 [m+H]$^+$
$^1$H-NMR (500 MHz, d$_6$-DMSO): δ [ppm] 8.25 (d, 1H); 8.10 (m, 3H); 8.05 (d, 1H); 7.90 (d, 1H); 7.35 (s, 1H); 7.25 (d, 2H); 7.10 (m, 1H); 6.90 (d, 2H); 6.80 (d, 1H); 3.95 (m, 1H); 3.85 (s, 3H); 3.80 (m, 1H); 3.70 (m, 1H); 3.10 (bs, 4H); 2.95 (m, 1H); 2.85 (m, 1H); 2.50 (bs, 4H); 2.40 (m, 2H); 1.05 (t, 3H); 0.80 (t, 3H).

EXAMPLE 32

1-(2,4-Dimethoxyphenylsulfonyl)-3-(2-ethoxypyridin-3-yl)-3-[4-(4-ethylpiperazin-1-yl)-benzylamino]-2-oxo-2,3-dihydro-1H-indole-5-carbonitrile ESI-MS: 697.20 [m+H]$^+$

EXAMPLE 33

3-(2-Ethoxypyridin-3-yl)-6-fluoro-1-(4-methoxyphenylsulfonyl)-3-[4-(4-methylpiperazin-1-yl)benzylamino]-2-oxo-2,3-dihydro-1H-indole-5-carbonitrile

33.1 3-Chloro-3-(2-ethoxypyridin-3-yl)-6-fluoro-2-oxo-2,3-dihydro-1H-indole-5-carbonitrile ESI-MS: 332.00 [m+H]$^+$

33.2 3-(2-Ethoxypyridin-3-yl)-6-fluoro-3-[4-(4-methylpiperazin-1-yl)benzylamino]-2-oxo-2,3-dihydro-1H-indole-5-carbonitrile

ESI-MS: 501.25 [M+H]$^+$

33.3 3-(2-Ethoxypyridin-3-yl)-6-fluoro-1-(4-methoxyphenylsulfonyl)-3-[4-(4-methylpiperazin-1-yl)benzylamino]-2-oxo-2,3-dihydro-1H-indole-5-carbonitrile ESI-MS: 671.25 [m+H]$^+$
$^1$H-NMR (500 MHz, CDCl$_3$): δ [ppm] 8.20 (d, 1H); 8.15 (d, 2H); 8.10 (m, 1H); 7.95 (d, 1H); 7.10 (d, 1H); 7.05 (d, 2H); 6.95 (m, 1H); 6.85 (d, 2H); 6.80 (d, 2H); 4.15 (m, 1H); 4.10 (m, 1H); 3.85 (s, 3H); 3.20 (m, 4H); 2.90 (m, 1H); 2.80 (m, 1H); 2.65 (m, 4H); 2.35 (s, 3H); 2.15 (m, 1H); 1.05 (t, 3H).

EXAMPLE 34

3-(2-Ethoxypyridin-3-yl)-6-fluoro-1-(4-methoxyphenylsulfonyl)-2-oxo-3-(4-piperazin-1-yl-benzylamino)-2,3-dihydro-1H-indole-5-carbonitrile

34.1 tert-Butyl 4-(4-{[5-cyano-3-(2-ethoxypyridin-3-yl)-6-fluoro-2-oxo-2,3-dihydro-1H-indol-3-ylamino]methyl}phenyl)piperazine-1-carboxylate ESI-MS: 587.25 [m+H]$^+$

34.2 tert-Butyl 4-(4-{[5-cyano-3-(2-ethoxypyridin-3-yl)-6-fluoro-1-(4-methoxyphenylsulfonyl)-2-oxo-2,3-dihydro-1H-indol-3-ylamino]methyl}phenyl)piperazine-1-carboxylate ESI-MS: 757.25 [m+H]$^+$

34.3 3-(2-Ethoxypyridin-3-yl)-6-fluoro-1-(4-methoxyphenylsulfonyl)-2-oxo-3-(4-piperazin-1-yl-benzylamino)-2,3-dihydro-1H-indole-5-carbonitrile ESI-MS: 657.25 [m+H]$^+$
$^1$H-NMR (500 MHz, d$_6$-DMSO): δ [ppm] 8.25 (d, 1H); 8.20 (d, 2H); 8.10 (m, 1H); 7.90 (d, 1H); 7.40 (d, 1H); 7.25 (d, 2H); 7.10 (m, 1H); 6.90 (d, 2H); 6.80 (d, 1H); 3.95 (m, 1H); 3.85 (s, 3H); 3.80 (m, 1H); 3.75 (m, 1H); 3.10 (m, 4H); 2.95 (m, 6H); 0.85 (t, 3H).

EXAMPLE 35

3-(2-Ethoxypyridin-3-yl)-3-[4-(4-ethylpiperazin-1-yl)benzylamino]-6-fluoro-1-(4-methoxyphenylsulfonyl)-2-oxo-2,3-dihydro-1H-indole-5-carbonitrile ESI-MS: 685.20 [m+H]$^+$
$^1$H-NMR (500 MHz, d$_6$-DMSO): δ [ppm] 8.25 (d, 1H); 8.20 (d, 2H); 8.15 (m, 1H); 7.40 (d, 1H); 7.25 (d, 2H); 7.10 (m, 1H); 6.85 (d, 2H); 6.80 (d, 1H); 3.95 (m, 1H); 3.85 (m, 4H); 3.75 (m, 1H); 3.10 (m, 4H); 3.00 (m, 1H); 2.95 (m, 1H); 2.50 (bs, 4H); 2.40 (m, 2H); 1.05 (t, 3H); 0.80 (t, 3H).

EXAMPLE 36

1-[4-(2,2-Difluoroethoxy)phenylsulfonyl]-3-(2-ethoxypyridin-3-yl)-6-fluoro-3-[4-(4-methylpiperazin-1-yl)benzylamino]-2-oxo-2,3-dihydro-1H-indole-5-carbonitrile ESI-MS: 721.25 [m+H]$^+$
$^1$H-NMR (500 MHz, d$_6$-DMSO): δ [ppm] 8.25 (m, 3H); 8.10 (m, 2H); 7.90 (d, 1H); 7.40 (d, 1H); 7.35 (d, 2H); 7.15 (m, 1H); 6.85 (d, 2H); 6.75 (d, 2H); 6.40 (t, J=70 Hz, 1H); 4.45 (m, 2H); 3.95 (m, 1H); 3.85 (m, 1H); 3.80 (m, 1H); 3.05 (m, 4H); 3.00 (m, 1H); 2.95 (m, 1H); 2.45 (m, 4H); 2.25 (m, 3H); 0.85 (t, 3H).

EXAMPLE 37

3-(2-Ethoxyphenyl)-1-(4-methoxyphenylsulfonyl)-3-[4-(4-methylpiperazin-1-yl)-benzylamino]-2-oxo-2,3-dihydro-1H-indole-5-carbonitrile ESI-MS: 652.20 [m+H]$^+$
$^1$H-NMR (500 MHz, d$_6$-DMSO): δ [ppm] 8.15 (d, 2H); 8.10 (d, 1H); 8.00 (d, 1H); 7.95 (d, 1H); 7.40 (t, 1H); 7.30 (m, 3H); 7.15 (t, 1H); 6.95 (d, 1H); 6.90 (d, 2H); 6.80 (d, 2H); 4.05 (m, 1H); 3.90 (s, 3H); 3.80 (m, 1H); 3.70 (m, 1H); 3.15 (m, 4H); 2.95 (m, 1H); 2.85 (m, 1H); 2.50 (m, 4H); 2.30 (s, 3H); 0.95 (t, 3H).

I.3.2 Compounds I in which $X^1$ is —NH—CH$_2$— and A is 1,3-phenylene

EXAMPLE 38

1-(2,4-Dimethoxyphenylsulfonyl)-3-(2-ethoxypyridin-3-yl)-5-iodo-3-[3-(4-methylpiperazin-1-yl)benzylamino]-1,3-dihydroindol-2-one 38.1 3-(2-Ethoxypyridin-3-yl)-5-iodo-3-[3-(4-methylpiperazin-1-yl)benzylamino]-1,3-dihydroindol-2-one ESI-MS: 584.15 [m+H]$^+$ 38.2 1-(2,4-Dimethoxyphenylsulfonyl)-3-(2-ethoxypyridin-3-yl)-5-iodo-3-[3-(4-methylpiperazin-1-yl)benzylamino]-1,3-dihydroindol-2-one ESI-MS: 784.15 [M+H]$^+$
$^1$H-NMR (500 MHz, d$_6$-DMSO): δ [ppm] 8.20 (m, 2H); 8.10 (m, 1H); 7.80 (d, 1H); 7.70 (d, 1H); 7.30 (d, 1H); 7.15 (m, 1H); 6.90 (m, 1H); 6.80 (d, 1H); 6.65 (d, 1H); 6.60 (m, 2H); 6.40 (s, 1H); 4.25 (m, 2H); 3.85 (s, 3H); 3.55 (s, 3H); 3.20 (m, 4H); 3.10 (m, 1H); 2.90 (m, 1H); 2.60 (m, 4H); 2.40 (s, 3H); 2.15 (m, 1H); 1.20 (t, 3H).

EXAMPLE 39

3-(2-Ethoxypyridin-3-yl)-5-iodo-1-(4-methoxy-2-trifluoromethoxyphenylsulfonyl)-3-[3-(4-methylpiperazin-1-yl)benzylamino]-1,3-dihydroindol-2-one ESI-MS: 838.10 [m+H]$^+$
$^1$H-NMR (500 MHz, d$_6$-DMSO): δ [ppm] 8.35 (d, 1H); 8.20 (d, 1H); 8.10 (m, 1H); 7.80 (d, 1H); 7.70 (d, 1H); 7.25 (s, 1H); 7.15 (m, 1H); 6.95 (m, 2H); 6.80 (m, 2H); 6.60 (d, 1H); 6.55 (d, 1H); 4.25 (m, 2H); 3.90 (s, 3H); 3.20 (m, 5H); 3.00 (m, 1H); 2.60 (m, 4H); 2.35 (s, 3H); 2.10 (m, 1H); 1.15 (t, 3H).

EXAMPLE 40

3-(2-Ethoxypyridin-3-yl)-5-iodo-1-(4-methoxyphenylsulfonyl)-3-[3-(4-methylpiperazin-1-yl)-benzylamino]-1,3-dihydroindol-2-one ESI-MS: 754.15 [m+H]$^+$
$^1$H-NMR (500 MHz, d$_6$-DMSO): δ [ppm] 8.20 (d, 1H); 8.15 (m, 3H); 7.80 (d, 1H); 7.70 (d, 1H); 7.20 (s, 1H); 7.15 (m, 1H); 7.00 (d, 2H); 6.95 (m, 1H); 6.60 (d, 1H); 6.55 (m, 2H); 4.10 (m, 2H); 3.85 (s, 3H); 3.20 (m, 4H); 2.95 (m, 1H); 2.75 (m, 1H); 2.60 (m, 4H); 2.35 (s, 3H); 2.15 (m, 1H); 1.10 (t, 3H).

EXAMPLE 41

3-(2-Ethoxypyridin-3-yl)-5-iodo-1-(2-methoxyphenylsulfonyl)-3-[3-(4-methylpiperazin-1-yl)-benzylamino]-1,3-dihydroindol-2-one ESI-MS: 754.15 [m+H]$^+$
$^1$H-NMR (500 MHz, d$_6$-DMSO): δ [ppm] 8.30 (d, 1H); 8.15 (d, 1H); 8.10 (m, 1H); 7.85 (m, 1H); 7.70 (m, 1H); 7.60 (m, 1H); 7.30 (d, 1H); 7.15 (m, 2H); 6.90 (m, 2H); 6.80 (d, 1H); 6.55 (s, 1H); 6.50 (d, 1H); 4.25 (m, 2H); 3.60 (s, 3H); 3.15 (m, 4H); 3.10 (m, 1H); 2.90 (m, 1H); 2.60 (m, 4H); 2.40 (s, 3H); 2.15 (m, 1H); 1.20 (t, 3H).

EXAMPLE 42

1-(2,4-Dimethoxyphenylsulfonyl)-3-(2-ethoxypyridin-3-yl)-3-[3-(4-methylpiperazin-1-yl)-benzylamino]-2-oxo-2,3-dihydro-1H-indole-5-carbonitrile 42.1 3-(2-Ethoxypyridin-3-yl)-3-[3-(4-methylpiperazin-1-yl)benzylamino]-2-oxo-2,3-dihydro-1H-indole-5-carbonitrile

ESI-MS: 483.20 [M+H]$^+$ 42.2 1-(2,4-Dimethoxyphenylsulfonyl)-3-(2-ethoxypyridin-3-yl)-3-[3-(4-methylpiperazin-1-yl)benzylamino]-2-oxo-2,3-dihydro-1H-indole-5-carbonitrile ESI-MS: 683.10 [m+H]$^+$
$^1$H-NMR (500 MHz, d$_6$-DMSO): δ [ppm] 8.35 (d, 1H); 8.20 (m, 1H); 8.10 (m, 2H); 8.00 (d, 1H); 7.50 (s, 1H); 7.15 (m, 2H); 6.90 (d, 1H); 6.85 (m, 2H); 6.65 (m, 2H); 4.15 (m, 2H); 3.95 (s, 3H); 3.80 (m, 1H); 3.65 (s, 3H); 3.15 (bs, 4H); 3.10 (m, 1H); 3.00 (m, 1H); 2.50 (m, 4H); 2.30 (s, 3H); 1.05 (t, 3H).

EXAMPLE 43

3-(2-Ethoxypyridin-3-yl)-1-(4-methoxyphenylsulfonyl)-3-[3-(4-methylpiperazin-1-yl)-benzylamino]-2-oxo-2,3-dihydro-1H-indole-5-carbonitrile ESI-MS: 653.10 [m+H]$^+$
$^1$H-NMR (500 MHz, d$_6$-DMSO): δ [ppm] 8.35 (d, 1H); 8.20 (m, 3H); 8.10 (d, 1H); 7.95 (d, 1H); 7.45 (s, 1H); 7.30 (d, 2H); 7.20 (m, 1H); 7.15 (t, 1H); 6.80 (d, 1H); 6.60 (m, 2H); 4.05 (m, 1H); 3.95 (m, 1H); 3.90 (m, 4H); 3.15 (m, 4H); 3.05 (m, 1H); 2.95 (m, 1H); 2.50 (m, 4H); 2.30 (s, 3H); 0.90 (t, 3H).

EXAMPLE 44

3-(2-Ethoxypyridin-3-yl)-1-(2-methoxyphenylsulfonyl)-3-[3-(4-methylpiperazin-1-yl)-benzylamino]-2-oxo-2,3-dihydro-1H-indole-5-carbonitrile ESI-MS: 653.10 [m+H]$^+$
$^1$H-NMR (500 MHz, d$_6$-DMSO): δ [ppm] 8.35 (d, 1H); 8.20 (m, 2H); 8.10 (d, 1H); 8.00 (d, 1H); 7.85 (m, 1H); 7.55 (s, 1H); 7.35 (d, 1H); 7.30 (m, 1H); 7.15 (m, 2H); 6.80 (d, 1H); 6.65 (s, 1H); 6.60 (d, 1H); 4.15 (m, 2H); 3.85 (m, 1H); 3.70 (s, 3H); 3.15 (bs, 4H); 3.10 (m, 1H); 3.00 (m, 1H); 2.50 (m, 4H); 2.25 (s, 3H); 1.05 (t, 3H).

I.3.3 Compounds I in which $X^1$ is —NH—CH$_2$— and A is 1,2-phenylene

EXAMPLE 45

1-(2,4-Dimethoxyphenylsulfonyl)-3-(2-ethoxypyridin-3-yl)-3-[2-(4-methylpiperazin-1-yl)-benzylamino]-2-oxo-2,3-dihydro-1H-indole-5-carbonitrile 45.1 3-(2-Ethoxypyridin-3-yl)-3-[2-(4-methylpiperazin-1-yl)benzylamino]-2-oxo-2,3-dihydro-1H-indole-5-carbonitrile ESI-MS: 483.20 [m+H]$^+$

45.2 1-(2,4-Dimethoxyphenylsulfonyl)-3-(2-ethoxypyridin-3-yl)-3-[2-(4-methylpiperazin-1-yl)benzylamino]-2-oxo-2,3-dihydro-1H-indole-5-carbonitrile ESI-MS: 683.15 [M+H]$^+$
$^1$H-NMR (500 MHz, d$_6$-DMSO): δ [ppm] 8.20 (d, 2H); 8.10 (d, 2H); 7.75 (d, 1H); 7.25 (t, 1H); 7.20 (s, 1H); 7.10 (d, 1H); 7.00 (t, 1H); 6.90 (t, 2H); 6.85 (d, 1H); 6.60 (d, 1H); 6.25 (d, 1H); 4.20 (m, 2H); 3.75 (s, 3H); 3.55 (s, 3H); 3.20 (m, 1H); 3.10 (m, 1H); 3.05 (m, 1H); 2.90 (bs, 2H); 2.75 (m, 2H); 2.35 (m, 4H); 2.30 (s, 3H); 1.15 (t, 3H).

EXAMPLE 46

3-(2-Ethoxypyridin-3-yl)-1-(4-methoxyphenylsulfonyl)-3-[2-(4-methylpiperazin-1-yl)-benzylamino]-2-oxo-2,3-dihydro-1H-indole-5-carbonitrile ESI-MS: 653.10 [M+H]$^+$
$^1$H-NMR (500 MHz, d$_6$-DMSO): δ [ppm] 8.20 (m, 1H); 8.10 (m, 3H); 8.05 (d, 1H); 7.95 (d, 1H); 7.30 (m, 2H); 7.20 (m, 3H); 7.10 (t, 1H); 7.00 (m, 2H); 3.95 (m, 1H); 3.90 (m, 1H); 3.80 (s, 3H); 3.65 (m, 1H); 3.25 (m, 1H); 3.15 (m, 1H); 2.70 (m, 2H); 2.60 (m, 2H); 2.25 (m, 4H); 2.20 (s, 3H); 0.70 (t, 3H).

EXAMPLE 47

3-(2-Ethoxypyridin-3-yl)-1-(2-methoxyphenylsulfonyl)-3-[2-(4-methylpiperazin-1-yl)-benzylamino]-2-oxo-2,3-dihydro-1H-indole-5-carbonitrile ESI-MS: 653.10 [m+H]$^+$
$^1$H-NMR (500 MHz, d$_6$-DMSO): δ [ppm] 8.30 (d, 1H); 8.25 (d, 1H); 8.10 (m, 2H); 7.75 (d, 1H); 7.55 (t, 1H); 7.25 (m, 2H); 7.15 (t, 1H); 7.10 (d, 1H); 7.00 (t, 1H); 6.90 (m, 1H); 6.80 (d, 2H); 4.20 (m, 2H); 3.60 (s, 3H); 3.25 (m, 1H); 3.05 (m, 2H); 2.85 (m, 2H); 2.70 (m, 2H); 2.35 (m, 4H); 2.30 (s, 3H); 1.15 (t, 3H).

I.4 Preparation of the Compounds I in which X$^1$ is —NH—
I.4.1 Compounds I in which X$^1$ is —NH—, A is 1,4-phenylene, X$^2$ is a single bond, X$^3$ is N, n is 2 and m is 2

EXAMPLE 48

1-(2,4-Dimethoxyphenylsulfonyl)-3-(2-ethoxypyridin-3-yl)-3-[4-(4-ethylpiperazin-1-yl)-phenylamino]-5-iodo-1,3-dihydroindol-2-one

48.1 1-(2,4-Dimethoxyphenylsulfonyl)-3-(2-ethoxypyridin-3-yl)-3-hydroxy-5-iodo-1,3-dihydroindol-2-one Sodium hydride (145 mg of a 50% strength dispersion in mineral oil, 3.03 mmol) was added to an ice-cooled solution of 3-(2-ethoxypyridin-3-yl)-3-hydroxy-5-iodo-1,3-dihydroindol-2-one (1.0 g, 2.52 mmol) in DMF (20 ml). The reaction mixture was stirred at 0° C. for 15 minutes and then 2,4-dimethoxyphenylsulfonyl chloride (99 mg, 0.48 mmol) was added. The reaction mixture was stirred at room temperature for 2 hours, water was added, and the resulting precipitate was filtered off. The precipitate formed after stirring in ethyl ether (50 ml) overnight was filtered off with suction, resulting in 730 mg of the title compound (45% yield).
ESI-MS: 597.05 [M+H]$^+$

48.2 3-Chloro-1-(2,4-dimethoxyphenylsulfonyl)-3-(2-ethoxypyridin-3-yl)-5-iodo-1,3-dihydroindol-2-one Pyridine (40 μl, 0.46 mmol) and thionyl chloride (35 μl, 0.46 mmol) were added successively to an ice-cooled solution of 1-(2,4-dimethoxyphenylsulfonyl)-3-(2-ethoxypyridin-3-yl)-3-hydroxy-5-iodo-1,3-dihydroindol-2-one (100 mg, 0.15 mmol) in dichloromethane (30 ml). The reaction mixture was allowed to warm to room temperature and stirred for 3 hours. Ice-water was added to the reaction mixture, and the aqueous phase was extracted with dichloromethane. The organic phase was dried over magnesium sulfate, filtered and concentrated under reduced pressure. The resulting crude product (110 mg) was employed without further purification in the next stage.
ESI-MS: 614.90 [m+H]$^+$

48.3 1-(2,4-Dimethoxyphenylsulfonyl)-3-(2-ethoxypyridin-3-yl)-3-[4-(4-ethylpiperazin-1-yl)-phenylamino]-5-iodo-1,3-dihydroindol-2-one 4-(4-Ethylpiperazin-1-yl)phenylamine (44 mg, 0.21 mmol) was added to a solution of 3-chloro-1-(2,4-dimethoxyphenylsulfonyl)-3-(2-ethoxypyridin-3-yl)-5-iodo-1,3-dihydroindol-2-one (110 mg, 0.18 mmol) in dichloromethane (15 ml). The reaction mixture was agitated in a Biotage microwave vial at 120° C. for 4 hours. The reaction mixture was concentrated under reduced pressure. Purification by chromatography (silica gel, 0-8% methanol in dichloromethane) resulted in 16 mg of the title compound (11% yield).
ESI-MS: 784.20 [m+H]$^+$
$^1$H-NMR (500 MHz, d$_6$-DMSO): δ [ppm] 8.15 (m, 1H); 8.05 (d, 1H); 7.85 (d, 1H); 7.75 (d, 1H); 7.50 (d, 1H); 7.30 (s, 1H), 7.10 (dd, 1H); 6.70 (d, 1H); 6.65 (s, 1H); 6.45 (d, 2H); 6.40 (d, 2H); 4.05 (m, 2H); 3.85 (s, 3H); 3.55 (s, 3H); 2.95 (bs, 4H); 2.45 (bs, 4H); 2.35 (m, 2H); 1.00 (t, 3H); 0.90 (t, 3H).

EXAMPLE 49

1-(2,4-Dimethoxyphenylsulfonyl)-3-(2-ethoxypyridin-3-yl)-5-iodo-3-[4-(4-methylpiperazin-1-yl)phenylamino]-1,3-dihydroindol-2-one

49.1 3-(2-Ethoxypyridin-3-yl)-5-iodo-3-[4-(4-methylpiperazin-1-yl)phenylamino]-1,3-dihydroindol-2-one ESI-MS: 570.15 [m+H]$^+$

49.2 1-(2,4-Dimethoxyphenylsulfonyl)-3-(2-ethoxypyridin-3-yl)-5-iodo-3-[4-(4-methylpiperazin-1-yl)phenylamino]-1,3-dihydroindol-2-one ESI-MS: 770.70 [m+H]$^+$
$^1$H-NMR (500 MHz, CDCl$_3$): δ [ppm] 8.25 (d, 1H); 8.15 (m, 1H); 8.05 (d, 1H); 7.60 (m, 2H); 7.45 (s, 1H); 6.95 (m, 1H); 6.55 (d, 1H); 6.35 (m, 4H); 6.25 (m, 1H); 4.25 (m, 2H); 3.90 (s, 3H); 3.35 (s, 3H); 3.05 (m, 4H); 2.55 (m, 4H); 2.35 (s, 3H); 1.20 (t, 3H).

EXAMPLE 50

3-(2-Ethoxypyridin-3-yl)-5-iodo-1-(4-methoxyphenylsulfonyl)-3-[4-(4-methylpiperazin-1-yl)-phenylamino]-1,3-dihydroindol-2-one ESI-MS: 740.15 [m+H]$^+$
$^1$H-NMR (500 MHz, d$_6$-DMSO): δ [ppm] 8.35 (d, 1H); 8.15 (m, 1H); 7.85 (d, 2H); 7.75 (d, 1H); 7.60 (d, 1H); 7.35 (s, 1H); 7.10 (m, 1H); 7.05 (d, 1H); 6.45 (d, 2H); 6.35 (d, 2H); 4.15 (m, 1H); 4.00 (m, 1H); 3.95 (s, 3H); 3.05 (m, 4H); 2.60 (m, 4H); 2.35 (s, 3H); 0.95 (t, 3H).

EXAMPLE 51

5-Chloro-3-(2-ethoxypyridin-3-yl)-1-(4-methoxyphenylsulfonyl)-3-[4-(4-methylpiperazin-1-yl)phenylamino]-1,3-dihydroindol-2-one 51.1 5-Chloro-3-(2-ethoxypyridin-3-yl)-3-[4-(4-methylpiperazin-1-yl)phenylamino]-1,3-dihydroindol-2-one ESI-MS: 478.20 [m+H]$^+$ 51.2 5-Chloro-3-(2-ethoxypyridin-3-yl)-1-(4-methoxyphenylsulfonyl)-3-[4-(4-methylpiperazin-1-yl)phenylamino]-1,3-dihydroindol-2-one ESI-MS: 648.15 [M+H]$^+$
$^1$H-NMR (500 MHz, CDCl$_3$): δ [ppm] 8.25 (d, 1H); 8.15 (m, 1H); 7.80 (d, 2H); 7.75 (d, 1H); 7.30 (m, 1H); 7.10 (s, 1H); 7.00 (m, 1H); 6.90 (d, 2H); 6.45 (d, 2H); 6.35 (d, 2H); 4.15 (m, 1H); 4.10 (m, 1H); 4.00 (s, 1H); 3.90 (s, 3H); 3.05 (m, 4H); 2.55 (m, 4H); 2.35 (s, 3H); 1.05 (t, 3H).

EXAMPLE 52

5-Chloro-3-(2-ethoxypyridin-3-yl)-6-fluoro-1-(4-methoxyphenylsulfonyl)-3-[4-(4-methylpiperazin-1-yl)phenylamino]-1,3-dihydroindol-2-one 52.1 5-Chloro-3-(2-ethoxypyridin-3-yl)-6-fluoro-3-[4-(4-methylpiperazin-1-yl)-phenylamino]-1,3-dihydroindol-2-one

ESI-MS: 496.20 [M+H]$^+$ 52.2 5-Chloro-3-(2-ethoxypyridin-3-yl)-6-fluoro-1-(4-methoxyphenylsulfonyl)-3-[4-(4-methylpiperazin-1-yl)phenylamino]-1,3-dihydroindol-2-one ESI-MS: 666.20 [m+H]$^+$
$^1$H-NMR (400 MHz, CDCl$_3$): δ [ppm] 8.25 (d, 1H); 8.15 (m, 1H); 7.80 (d, 2H); 7.65 (d, 1H); 7.10 (d, 1H); 7.00 (t, 1H); 6.95 (d, 2H); 6.35 (d, 2H); 6.25 (d, 2H); 4.15 (m, 2H); 3.95 (s, 1H); 3.90 (s, 3H); 3.05 (m, 4H); 2.55 (m, 4H); 2.35 (s, 3H); 1.05 (t, 3H).

EXAMPLE 53

6-Chloro-3-(2-ethoxypyridin-3-yl)-5-fluoro-1-(4-methoxyphenylsulfonyl)-3-[4-(4-methylpiperazin-1-yl)phenylamino]-1,3-dihydroindol-2-one 53.1 6-Chloro-3-(2-ethoxypyridin-3-yl)-5-fluoro-3-[4-(4-methylpiperazin-1-yl)-phenylamino]-1,3-dihydroindol-2-one ESI-MS: 496.20 [m+H]$^+$ 53.2 6-Chloro-3-(2-ethoxypyridin-3-yl)-5-fluoro-1-(4-methoxyphenylsulfonyl)-3-[4-(4-methylpiperazin-1-yl)phenylamino]-1,3-dihydroindol-2-one ESI-MS: 666.20 [m+H]$^+$
$^1$H-NMR (400 MHz, CDCl$_3$): δ [ppm] 8.25 (d, 1H); 8.15 (m, 1H); 7.90 (d, 1H); 7.85 (d, 2H); 6.95 (m, 1H); 6.90 (m, 3H); 6.35 (d, 2H); 6.25 (d, 2H); 4.15 (m, 2H); 3.95 (s, 1H); 3.90 (s, 3H); 3.05 (m, 4H); 2.55 (m, 4H); 2.35 (s, 3H); 1.05 (t, 3H).

EXAMPLE 54

3-(2-Ethoxypyridin-3-yl)-5,6-difluoro-1-(4-methoxyphenylsulfonyl)-3-[4-(4-methylpiperazin-1-yl)phenylamino]-1,3-dihydroindol-2-one 54.1 3-(2-Ethoxypyridin-3-yl)-5,6-difluoro-3-[4-(4-methylpiperazin-1-yl)phenylamino]-1,3-dihydroindol-2-one ESI-MS: 480.20 [m+H]$^+$ 54.2 3-(2-Ethoxypyridin-3-yl)-5,6-difluoro-1-(4-methoxyphenylsulfonyl)-3-[4-(4-methylpiperazin-1-yl)phenylamino]-1,3-dihydroindol-2-one ESI-MS: 650.25 [M+H]$^+$
$^1$H-NMR (400 MHz, CDCl$_3$): δ [ppm] 8.25 (d, 1H); 8.15 (m, 1H); 7.80 (d, 2H); 7.70 (m, 1H); 6.95 (m, 4H); 6.35 (d, 2H); 6.25 (d, 2H); 4.15 (m, 2H); 3.95 (s, 1H); 3.90 (s, 3H); 3.05 (m, 4H); 2.55 (m, 4H); 2.35 (s, 3H); 1.05 (t, 3H).

EXAMPLE 55

1-(2,4-Dimethoxyphenylsulfonyl)-3-(2-ethoxypyridin-3-yl)-3-[4-(4-methylpiperazin-1-yl)-phenylamino]-2-oxo-2,3-dihydro-1H-indole-5-carbonitrile 55.1 3-(2-Ethoxypyridin-3-yl)-3-[4-(4-methylpiperazin-1-yl)phenylamino]-2-oxo-2,3-dihydro-1H-indole-5-carbonitrile ESI-MS: 469.25 [m+H]$^+$ 55.2 1-(2,4-Dimethoxyphenylsulfonyl)-3-(2-ethoxypyridin-3-yl)-3-[4-(4-methylpiperazin-1-yl)phenylamino]-2-oxo-2,3-dihydro-1H-indole-5-carbonitrile ESI-MS: 669.25 [m+H]$^+$
$^1$H-NMR (500 MHz, d$_6$-DMSO): δ [ppm] 8.30 (d, 1H); 8.15 (m, 1H); 8.05 (d, 1H); 7.95 (d, 1H); 7.60 (d, 1H); 7.45 (s, 1H); 7.00 (m, 1H); 6.55 (d, 1H); 6.30 (m, 5H); 4.25 (m, 2H); 3.90 (s, 3H); 3.35 (s, 3H); 3.05 (m, 4H); 2.55 (m, 4H); 2.35 (s, 3H); 1.15 (t, 3H).

EXAMPLE 56

1-(2,4-Dimethoxyphenylsulfonyl)-3-(2-ethoxypyridin-3-yl)-3-[4-(4-ethylpiperazin-1-yl)-phenylamino]-2-oxo-2,3-dihydro-1H-indole-5-carbonitrile 56.1 3-(2-Ethoxypyridin-3-yl)-3-[4-(4-ethylpiperazin-1-yl)phenylamino]-2-oxo-2,3-dihydro-1H-indole-5-carbonitrile

ESI-MS: 483.30 [M+H]$^+$ 56.2 1-(2,4-Dimethoxyphenylsulfonyl)-3-(2-ethoxypyridin-3-yl)-3-[4-(4-ethylpiperazin-1-yl)-phenylamino]-2-oxo-2,3-dihydro-1H-indole-5-carbonitrile ESI-MS: 683.30 [m+H]$^+$
$^1$H-NMR (500 MHz, CDCl$_3$): δ [ppm] 8.30 (d, 1H); 8.15 (m, 1H); 8.05 (d, 1H); 7.95 (d, 1H); 7.60 (d, 1H); 7.45 (s, 1H);

7.00 (m, 1H); 6.60 (d, 1H); 6.30 (m, 5H); 4.25 (m, 2H); 4.00 (m, 1H); 3.90 (s, 3H); 3.30 (s, 3H); 3.10 (m, 4H); 2.65 (m, 4H); 2.55 (m, 2H); 1.15 (m, 6H).

EXAMPLE 57

3-(2-Ethoxypyridin-3-yl)-3-[4-(4-ethylpiperazin-1-yl)phenylamino]-1-(4-methoxyphenylsulfonyl)-2-oxo-2,3-dihydro-1H-indole-5-carbonitrile ESI-MS: 653.30 [M+H]$^+$
$^1$H-NMR (500 MHz, CDCl$_3$): δ [ppm] 8.30 (d, 1H); 8.15 (m, 1H); 7.95 (d, 1H); 7.90 (m, 2H); 7.60 (d, 1H); 7.40 (s, 1H); 7.00 (t, 1H); 6.95 (d, 2H); 6.35 (d, 2H); 6.25 (d, 2H); 4.15 (m, 1H); 4.05 (m, 1H); 3.90 (s, 3H); 3.80 (m, 1H); 3.30 (s, 3H); 3.10 (m, 4H); 2.65 (m, 4H); 2.55 (m, 2H); 1.15 (t, 3H); 0.95 (t, 3H).

EXAMPLE 58

3-(2-Ethoxypyridin-3-yl)-3-[4-(4-ethylpiperazin-1-yl)phenylamino]-1-(2-methoxyphenylsulfonyl)-2-oxo-2,3-dihydro-1H-indole-5-carbonitrile ESI-MS: 653.30 [M+H]$^+$
$^1$H-NMR (500 MHz, CDCl$_3$): δ [ppm] 8.30 (d, 1H); 8.15 (m, 1H); 8.10 (d, 1H); 7.95 (d, 1H); 7.65 (d, 1H); 7.55 (t, 1H); 7.45 (s, 1H); 7.10 (t, 2H); 7.00 (m, 1H); 6.85 (d, 1H); 6.30 (m, 4H); 4.25 (m, 2H); 3.95 (s, 1H); 3.80 (m, 1H); 3.35 (s, 3H); 3.15 (bs, 4H); 2.65 (bs, 4H); 2.55 (m, 2H); 1.15 (m, 6H).

EXAMPLE 59

3-(2-Ethoxypyridin-3-yl)-6-fluoro-1-(4-methoxyphenylsulfonyl)-3-[4-(4-methylpiperazin-1-yl)phenylamino]-2-oxo-2,3-dihydro-1H-indole-5-carbonitrile 59.1 3-(2-Ethoxypyridin-3-yl)-6-fluoro-3-[4-(4-methylpiperazin-1-yl)phenylamino]-2-oxo-2,3-dihydro-1H-indole-5-carbonitrile

ESI-MS: 487.25 [M+H]$^+$ 59.2 3-(2-Ethoxypyridin-3-yl)-6-fluoro-1-(4-methoxyphenylsulfonyl)-3-[4-(4-methylpiperazin-1-yl)phenylamino]-2-oxo-2,3-dihydro-1H-indole-5-carbonitrile ESI-MS: 657.25 [m+H]$^+$
$^1$H-NMR (500 MHz, d$_6$-DMSO): δ [ppm] 8.15 (m, 2H); 8.00 (d, 2H); 7.80 (d, 1H); 7.70 (d, 1H); 7.15 (m, 3H); 6.45 (d, 2H); 6.35 (d, 2H); 6.00 (s, 1H); 3.95 (m, 1H); 3.90 (s, 3H); 3.80 (m, 1H); 2.95 (bs, 4H); 2.45 (bs, 4H); 2.25 (s, 3H); 0.75 (m, 6H).

I.4.2 Compounds I in which X$^1$ is —NH—, A is 1,3-phenylene, X$^2$ is a Single Bond, X$^3$ is N, n is 2 and m is 2

EXAMPLE 60

1-(2,4-Dimethoxyphenylsulfonyl)-3-(2-ethoxypyridin-3-yl)-5-iodo-3-[3-(4-methylpiperazin-1-yl)phenylamino]-1,3-dihydroindol-2-one 60.1 3-(2-Ethoxypyridin-3-yl)-5-iodo-3-[3-(4-methylpiperazin-1-yl)phenylamino]-1,3-dihydroindol-2-one ESI-MS: 570.15 [m+H]$^+$
$^1$H-NMR (500 MHz, CDCl$_3$): δ [ppm] 8.20 (d, 1H); 8.15 (m, 1H); 7.55 (d, 1H); 7.40 (s, 1H); 7.00 (m, 2H); 6.55 (d, 1H); 6.45 (d, 1H); 6.25 (d, 1H); 6.15 (s, 1H); 4.25 (m, 2H); 2.50 (bs, 4H); 2.30 (s, 3H); 2.05 (bs, 3H); 1.15 (t, 3H).

60.2 1-(2,4-Dimethoxyphenylsulfonyl)-3-(2-ethoxypyridin-3-yl)-5-iodo-3-[3-(4-methylpiperazin-1-yl)phenylamino]-1,3-dihydroindol-2-one ESI-MS: 770.10 [m+H]$^+$
$^1$H-NMR (500 MHz, d$_6$-DMSO): δ [ppm] 8.15 (m, 1H); 7.95 (d, 1H); 7.90 (d, 1H); 7.75 (d, 1H); 7.50 (d, 1H); 7.30 (s, 1H); 7.05 (d, 1H); 6.70 (m, 2H); 6.65 (s, 1H); 6.25 (m, 2H); 6.20 (s, 1H); 6.00 (d, 1H); 4.05 (m, 2H); 3.85 (s, 3H); 3.55 (s, 3H); 2.85 (m, 4H); 2.35 (bs, 4H); 2.20 (bs, 3H); 0.90 (t, 3H).

EXAMPLE 61

3-(2-Ethoxypyridin-3-yl)-1-(4-methoxyphenylsulfonyl)-3-[3-(4-methylpiperazin-1-yl)-phenylamino]-2-oxo-2,3-dihydro-1H-indole-5-carbonitrile 61.1 3-(2-Ethoxypyridin-3-yl)-3-[3-(4-methylpiperazin-1-yl)phenylamino]-2-oxo-2,3-dihydro-1H-indole-5-carbonitrile ESI-MS: 469.25 [m+H]$^+$ 61.2 3-(2-Ethoxypyridin-3-yl)-1-(4-methoxyphenylsulfonyl)-3-[3-(4-methylpiperazin-1-yl)-phenylamino]-2-oxo-2,3-dihydro-1H-indole-5-carbonitrile ESI-MS: 639.25 [m+H]$^+$
$^1$H-NMR (500 MHz, d$_6$-DMSO): δ [ppm] 8.15 (m, 1H); 8.05 (d, 1H); 7.95 (m, 4H); 7.55 (s, 1H); 7.15 (d, 1H); 7.10 (m, 2H); 6.70 (t, 1H); 6.30 (s, 1H); 6.25 (m, 1H); 6.10 (s, 1H); 5.95 (d, 1H); 3.95 (m, 1H); 3.85 (s, 3H); 3.65 (m, 1H); 2.85 (m, 4H); 2.35 (bs, 4H); 2.20 (s, 3H); 0.65 (t, 3H).

EXAMPLE 62

1-(2,4-Dimethoxyphenylsulfonyl)-3-(2-ethoxypyridin-3-yl)-3-[3-(4-methylpiperazin-1-yl)-phenylamino]-2-oxo-2,3-dihydro-1H-indole-5-carbonitrile ESI-MS: 669.25 [m+H]$^+$
$^1$H-NMR (500 MHz, d$_6$-DMSO): δ [ppm] 8.15 (m, 1H); 8.05 (d, 1H); 7.90 (m, 3H); 7.55 (s, 1H); 7.10 (m, 1H); 6.70 (m, 2H); 6.65 (m, 1H); 6.30 (m, 2H); 6.20 (s, 1H); 5.95 (d, 1H); 4.05 (m, 2H); 3.85 (s, 3H); 3.55 (s, 3H); 2.85 (m, 4H); 2.35 (bs, 4H); 2.20 (s, 3H); 0.85 (t, 3H).

I.4.3 Compounds I in which X$^1$ is —NH—, A is 1,4-phenylene, X$^2$ is a single bond, X$^3$ is CH, n is 1 and m is 1

EXAMPLE 63

3-(4-Azetidin-3-ylphenylamino)-1-(2,4-dimethoxyphenylsulfonyl)-3-(2-ethoxypyridin-3-yl)-5-iodo-1,3-dihydroindol-2-one as hydrochloride 63.1 tert-Butyl 3-{4-[3-(2-ethoxypyridin-3-yl)-5-iodo-2-oxo-2,3-dihydro-1H-indol-3-ylamino]-phenyl}azetidine-1-carboxylate ESI-MS: 626.90 [m+H]$^+$ 63.2 tert-Butyl 3-{4-[1-(2,4-dimethoxyphenylsulfonyl)-3-(2-ethoxypyridin-3-yl)-5-iodo-2-oxo-2,3-dihydro-1H-indol-3-ylamino]phenyl}azetidine-1-carboxylate 63.3 3-(4-Azetidin-3-ylphenylamino)-1-(2,4-dimethoxyphenylsulfonyl)-3-(2-ethoxypyridin-3-yl)-5-iodo-1,3-dihydroindol-2-one as hydrochloride ESI-MS: 765.00 [M+H]$^+$
$^1$H-NMR (500 MHz, CDCl$_3$): δ [ppm] 9.75 (bs, 1H); 9.45 (bs, 1H); 8.15 (d, 1H); 8.00 (d, 1H); 7.80 (d, 1H); 7.65 (d, 1H); 7.60 (d, 1H), 7.35 (s, 1H); 7.00 (m, 2H); 6.90 (t, 1H); 6.55 (m, 3H); 6.45 (m, 1H); 4.55 (m, 1H); 4.30-4.00 (m, 7H); 3.85 (s, 3H); 3.55 (s, 3H); 1.15 (t, 3H).

EXAMPLE 64

1-(2,4-Dimethoxyphenylsulfonyl)-3-(2-ethoxypyridin-3-yl)-3-[4-(1-ethylazetidin-3-yl)-phenylamino]-5-iodo-1,3-dihydroindol-2-one as trifluoroacetic acid salt $^1$H-NMR (500 MHz, CDCl$_3$): δ [ppm] 13.55 (bs, 1H); 8.15 (m, 1H); 8.05 (d, 1H); 7.80 (d, 1H); 7.65 (m, 2H); 7.35 (s, 1H); 6.90 (m, 1H); 6.85 (d, 2H); 6.55 (m, 4H); 6.35 (s, 1H); 4.60 (m, 2H); 4.25 (m, 1H); 4.15 (m, 2H); 3.85 (s, 3H); 3.60 (m, 2H); 3.55 (s, 3H); 3.15 (m, 2H); 1.25 (t, 3H); 1.10 (t, 3H).

EXAMPLE 65

3-(4-Azetidin-3-ylphenylamino)-3-(2-ethoxypyridin-3-yl)-5-iodo-1-(4-methoxyphenylsulfonyl)-1,3-dihydroindol-2-one 65.1 tert-Butyl 3-{4-[3-(2-ethoxypyridin-3-yl)-5-iodo-1-(4-methoxyphenylsulfonyl)-2-oxo-2,3-dihydro-1H-indol-3-ylamino]phenyl}azetidine-1-carboxylate ESI-MS: 741.10 [M-$^t$Bu+H]$^+$ 65.2 3-(4-Azetidin-3-ylphenylamino)-3-(2-ethoxypyridin-3-yl)-5-iodo-1-(4-methoxyphenylsulfonyl)-1,3-dihydroindol-2-one $^1$H-NMR (500 MHz, CDCl$_3$): δ [ppm] 9.80 (bs, 1H); 9.45 (bs, 1H); 8.15 (d, 1H); 7.95 (d, 1H); 7.90 (d, 2H); 7.65 (m, 2H); 7.30 (s, 1H); 7.00-6.80 (m, 5H); 6.45 (m, 2H); 4.30 (bs, 2H); 4.20-3.95 (m, 5H); 3.85 (s, 3H); 0.95 (t, 3H).

EXAMPLE 66

3-(2-Ethoxypyridin-3-yl)-3-[4-(1-ethylazetidin-3-yl) phenylamino]-5-iodo-1-(4-methoxyphenylsulfonyl)-1,3-dihydroindol-2-one as trifluoroacetic acid salt ESI-MS: 725.15 [m+H]$^+$
$^1$H-NMR (500 MHz, CDCl$_3$): δ [ppm] 13.55 (bs, 1H); 8.15 (m, 1H); 7.95 (m, 3H); 7.70 (d, 1H); 7.65 (d, 1H); 7.30 (s, 1H); 6.95 (m, 1H); 6.90 (d, 2H); 6.80 (d, 2H); 6.45 (d, 2H); 4.60 (m, 2H); 4.10 (m, 2H); 3.95 (m, 1H); 3.90 (s, 3H); 3.65 (m, 2H); 3.15 (m, 2H); 1.25 (t, 3H); 0.90 (t, 3H).

I.4.4 Compounds I in which X$^1$ is —NH—, A is Pyridylene, X$^2$ is a Single Bond, X$^3$ is N, n is 2 and m is 2

EXAMPLE 67

1-(2,4-Dimethoxyphenylsulfonyl)-3-(2-ethoxypyridin-3-yl)-5-iodo-3-[6-(4-methylpiperazin-1-yl)pyridin-3-ylamino]-1,3-dihydroindol-2-one 67.1 3-(2-Ethoxypyridin-3-yl)-5-iodo-3-[6-(4-methylpiperazin-1-yl)pyridin-3-ylamino]-1,3-dihydroindol-2-one ESI-MS: 571.20 [m+H]$^+$ 67.2 1-(2,4-Dimethoxyphenylsulfonyl)-3-(2-ethoxypyridin-3-yl)-5-iodo-3-[6-(4-methylpiperazin-1-yl)pyridin-3-ylamino]-1,3-dihydroindol-2-one ESI-MS: 771.15 [M+H]$^+$
$^1$H-NMR (500 MHz, d$_6$-DMSO): δ [ppm] 8.20 (d, 1H); 8.15 (m, 1H); 7.85 (d, 1H); 7.75 (d, 1H); 7.55 (d, 1H); 7.35 (s, 1H); 7.25 (m, 1H); 7.10 (m, 1H); 6.70 (d, 1H); 6.55 (s, 1H); 6.30 (d, 1H); 5.85 (s, 1H); 4.05 (m, 2H); 3.85 (s, 3H); 3.55 (s, 3H); 3.25 (m, 4H); 2.40 (m, 4H); 2.20 (s, 3H); 0.95 (t, 3H).

EXAMPLE 68

3-(2-Ethoxypyridin-3-yl)-5-iodo-1-(4-methoxyphenylsulfonyl)-3-[6-(4-methylpiperazin-1-yl)-pyridin-3-ylamino]-1,3-dihydroindol-2-one ESI-MS: 741.10 [m+H]$^+$
$^1$H-NMR (500 MHz, d$_6$-DMSO): δ [ppm] 8.15 (m, 1H); 8.10 (d, 1H); 7.90 (d, 2H); 7.80 (d, 1H); 7.60 (d, 1H); 7.40 (m, 1H); 7.30 (s, 1H); 7.15 (m, 1H); 6.85 (d, 1H); 6.65 (d, 1H); 4.15 (m, 2H); 3.95 (m, 1H); 3.85 (s, 3H); 3.75 (m, 1H); 3.50 (m, 2H); 3.05 (m, 4H); 2.85 (s, 3H); 0.70 (t, 3H).

EXAMPLE 69

1-Phenylsulfonyl-3-(2-ethoxypyridin-3-yl)-5-iodo-3-[6-(4-methylpiperazin-1-yl)pyridin-3-ylamino]-1,3-dihydroindol-2-one ESI-MS: 711.10 [m+H]$^+$
$^1$H-NMR (500 MHz, d$_6$-DMSO): δ [ppm] 8.15 (m, 2H); 7.95 (d, 2H); 7.80 (m, 2H); 7.65 (m, 3H); 7.40 (m, 1H); 7.35 (s, 1H); 7.15 (m, 1H); 6.80 (d, 1H); 6.60 (d, 1H); 4.15 (m, 2H); 3.95 (m, 1H); 3.70 (m, 1H); 3.50 (m, 2H); 3.05 (m, 4H); 2.85 (s, 3H); 0.65 (t, 3H).

I.4.5 Compounds I in which X$^1$ is —NH—, A is 1,4-phenylene, X$^2$ is —C(=O)—, X$^3$ is N, n is 2 and m is 2

EXAMPLE 70

3-(2-Ethoxypyridin-3-yl)-5-iodo-1-(4-methoxyphenylsulfonyl)-3-[4-(4-methylpiperazin-1-carbonyl) phenylamino]-1,3-dihydroindol-2-one 70.1 3-(2-Ethoxypyridin-3-yl)-5-iodo-3-[4-(4-methylpiperazin-1-carbonyl)phenylamino]-1,3-dihydroindol-2-one ESI-MS: 598.15 [m+H]$^+$ 70.2 3-(2-Ethoxypyridin-3-yl)-5-iodo-1-(4-methoxyphenylsulfonyl)-3-[4-(4-methylpiperazin-1-carbonyl)phenylamino]-1,3-dihydroindol-2-one ESI-MS: 768.10 [m+H]$^+$
$^1$H-NMR (500 MHz, d$_6$-DMSO): δ [ppm] 8.15 (m, 1H); 8.00 (d, 2H); 7.85 (m, 2H); 7.7 (d, 1H); 7.25 (s, 1H), 7.15 (d, 2H); 7.10 (m, 1H); 7.05 (d, 2H); 7.0 (s, 1H); 6.60 (d, 2H); 3.95 (m, 1H); 3.85 (s, 3H); 3.70 (m, 1H); 3.45 (bs, 4H); 2.30 (bs, 4H); 2.20 (s, 3H); 0.65 (t, 3H).

EXAMPLE 71

1-(2,4-Dimethoxyphenylsulfonyl)-3-(2-ethoxypyridin-3-yl)-5-iodo-3-[4-(4-methylpiperazin-1-carbonyl)phenylamino]-1,3-dihydroindol-2-one

ESI-MS: 798.10 [M+H]$^+$

EXAMPLE 72

3-(2-Ethoxypyridin-3-yl)-1-(4-methoxyphenylsulfonyl)-3-[4-(4-methylpiperazin-1-carbonyl)-phenylamino]-2-oxo-2,3-dihydro-1H-indole-5-carbonitrile 72.1 3-(2-Ethoxypyridin-3-yl)-3-[4-(4-methylpiperazin-1-carbonyl)phenylamino]-2-oxo-2,3-dihydro-1H-indole-5-carbonitrile ESI-MS: 497.20 [m+H]$^+$ 72.2 3-(2-Ethoxypyridin-3-yl)-1-(4-methoxyphenylsulfonyl)-3-[4-(4-methylpiperazin-1-carbonyl)phenylamino]-2-oxo-2,3-dihydro-1H-indole-5-carbonitrile ESI-MS: 667.25 [m+H]$^+$
$^1$H-NMR (500 MHz, d$_6$-DMSO): δ [ppm] 8.10 (m, 1H); 8.00 (m, 3H); 7.95 (d, 1H); 7.85 (d, 1H); 7.5 (m, 1H); 7.15 (d, 2H), 7.05 (m, 3H); 7.0 (s, 1H); 6.55 (d, 2H); 3.85 (m, 1H); 3.80 (s, 3H); 3.60 (m, 1H); 3.50 (bs, 4H); 2.50 (bs, 4H); 2.35 (bs, 3H); 0.55 (t, 3H).

EXAMPLE 73

1-(2,4-Dimethoxyphenylsulfonyl)-3-(2-ethoxypyridin-3-yl)-3-[4-(4-methylpiperazin-1-carbonyl)phenylamino]-2-oxo-2,3-dihydro-1H-indole-5-carbonitrile ESI-MS: 697.25 [m+H]$^+$
$^1$H-NMR (500 MHz, d$_6$-DMSO): δ [ppm] 8.10 (m, 1H); 8.00 (m, 3H); 7.90-7.80 (m, 4H); 7.5 (m, 1H); 7.05 (m, 1H); 7.0 (d, 2H); 6.90 (s, 1H); 6.70 (m, 2H); 6.60 (d, 2H); 4.05-3.95 (m, 2H); 3.80 (s, 3H); 3.60 (s, 3H); 3.40 (bs, 4H); 2.25 (bs, 4H); 2.15 (s, 3H); 0.80 (t, 3H).

I.4.6 Compounds I in which X$^1$ is —NH—, A is 1,4-phenylene, X$^2$ is —CH$_2$—, X$^3$ is N, n is 2 and m is 2

EXAMPLE 74

1-(2,4-Dimethoxyphenylsulfonyl)-3-(2-ethoxypyridin-3-yl)-3-[4-(4-methylpiperazin-1-ylmethyl)phenylamino]-2-oxo-2,3-dihydro-1H-indole-5-carbonitrile 74.1 3-(2-Ethoxypyridin-3-yl)-3-[4-(4-methylpiperazin-1-ylmethyl)phenylamino]-2-oxo-2,3-dihydro-1H-indole-5-carbonitrile 4-(4-Methyl-piperazin-1-ylmethyl)phenylamine (425 mg, 2.07 mmol) was added to a solution of 3-chloro-3-(2-ethoxypyridin-3-yl)-2-oxo-2,3-dihydro-1H-indole-5-carbonitrile (500 mg, 1.59 mmol) in dichloromethane (50 ml) and DIPEA (0.27 ml, 159 mmol) at 0° C. The reaction mixture was stirred at room temperature for 2 h and then an aqueous NaHCO$_3$ solution was added. The aqueous reaction mixture was extracted with dichloromethane. The combined organic phase was dried over magnesium sulfate, filtered and concentrated at reduced pressure. Purification by chromatography (silica gel, 0-20% methanol in dichloromethane) afforded 791 mg of the title compound (99% yield).

ESI-MS: 483.25 [M+H]$^+$ 74.2 1-(2,4-Dimethoxyphenylsulfonyl)-3-(2-ethoxypyridin-3-yl)-3-[4-(4-methylpiperazin-1-ylmethyl)phenylamino]-2-oxo-2,3-dihydro-1H-indole-5-carbonitrile ESI-MS: 683.25 [m+H]$^+$
$^1$H-NMR (500 MHz, d$_6$-DMSO): δ [ppm] 8.15 (m, 1H); 7.95 (d, 1H); 7.90 (m, 3H); 7.5 (s, 1H); 7.1 (m, 1H), 6.80 (d, 2H); 6.70 (m, 2H); 6.50 (d, 2H); 6.45 (s, 1H); 4.05 (m, 2H); 3.85 (s, 3H); 3.60 (s, 3H); 3.25 (s, 2H); 2.30 (bs, 8H); 2.15 (s, 3H); 0.85 (t, 3H).

EXAMPLE 75

3-(2-Ethoxypyridin-3-yl)-1-(4-methoxyphenylsulfonyl)-3-[4-(4-methylpiperazin-1-ylmethyl)-phenylamino]-2-oxo-2,3-dihydro-1H-indole-5-carbonitrile $^1$H-NMR (500 MHz, d$^6$-DMSO): δ [ppm] 8.15 (m, 1H); 8.05-7.95 (m, 5H); 7.55 (m, 1H); 7.20 (d, 2H); 7.10 (t, 1H); 6.85 (d, 2H); 6.55 (m, 2H); 3.95 (m, 1H); 3.85 (s, 3H); 3.75 (m, 2H); 3.60 (m, 1H); 3.35 (m, 4H); 2.90 (m, 4H); 2.60 (m, 3H); 0.60 (t, 3H).

EXAMPLE 76

3-(2-(2,2-Difluoroethoxy)pyridin-3-yl)-1-(4-methoxyphenylsulfonyl)-3-[4-(4-methylpiperazin-1-yl)benzylamino]-2-oxo-2,3-dihydro-1H-indole-5-carbonitrile ESI-MS: 689.10 [m+H]$^+$

EXAMPLE 77

1-(4-Methoxyphenylsulfonyl)-3-(2-(2,2,2-trifluoroethoxy)pyridin-3-yl)-3-[4-(4-methylpiperazin-1-yl)benzylamino]-2-oxo-2,3-dihydro-1H-indole-5-carbonitrile ESI-MS: 707.20 [m+H]$^+$

EXAMPLE 78

3-(2-(2,2-Difluoroethoxy)phenyl)-1-(4-methoxyphenylsulfonyl)-3-[4-(4-methylpiperazin-1-yl)-benzylamino]-2-oxo-2,3-dihydro-1H-indole-5-carbonitrile ESI-MS: 688.20 [m+H]$^+$

EXAMPLE 79

3-[4-(4-Ethylpiperazin-1-yl)phenylamino]-1-(4-methoxyphenylsulfonyl)-3-(2-(2,2-difluoroethoxy)pyridin-3-yl)-2-oxo-2,3-dihydro-1H-indole-5-carbonitrile ESI-MS: 689.10 [m+H]$^+$

EXAMPLE 80

3-[4-(4-Ethylpiperazin-1-yl)phenylamino]-1-(4-methoxyphenylsulfonyl)-3-(2-(2,2,2-trifluoroethoxy)pyridin-3-yl)-2-oxo-2,3-dihydro-1H-indole-5-carbonitrile ESI-MS: 693.20 [m+H]$^+$

EXAMPLE 81

3-(2-(2,2-Difluoroethoxy)phenyl)-3-[4-(4-ethylpiperazin-1-yl)phenylamino]-1-(4-methoxyphenylsulfonyl)-2-oxo-2,3-dihydro-1H-indole-5-carbonitrile ESI-MS: 674.20 [m+H]$^+$

EXAMPLE 82

1-(2,4-Dimethoxyphenylsulfonyl)-3-[4-(4-methylpiperazin-1-yl)phenylamino]-3-(2-(trifluoromethoxy)phenyl)-2-oxo-2,3-dihydro-1H-indole-5-carbonitrile ESI-MS: 736.20 [m+H]$^+$ II. Determination of the Biological Activity
1. Vasopressin V1b Receptor Binding Assay:
Substances:

The test substances were dissolved in a concentration of 10$^{-2}$ M in DMSO and further diluted to 5×10$^{-4}$ M to 5×10$^{-9}$ M. These serial DMSO predilutions were diluted 1:10 with assay buffer. The substance concentration was further diluted 1:5 in the assay mixture (2% DMSO in the mixture).

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini # 1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (250 µl), membranes (50 µg/ml protein in incubation buffer) from CHO-K1 cells with stably expressed human V1b receptors (cell line hV1b__3H2_CHO) were incubated with 1.5 nM $^3$H-AVP (8-Arg-vasopressin, PerkinElmer #18479) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 µM AVP (Bachem # H1780). All determinations were carried out as triplicate determinations. After incubation (60 minutes at room temperature), the free radioligand was filtered off by vacuum filtration (Skatron cell harvester 7000) through Wathman GF/B glass fiber filter mats, and the filters were transferred into scintillation vials. The liquid scintillation measurement took place in a model 2000 or 2200CA Tricarb instrument (Packard). Conversion of the measured cpm into dpm was carried out with the aid of a standard quench series.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay:
Substances:

The test substances were dissolved in a concentration of 10$^{-2}$ M in DMSO. Further dilution of these DMSO solutions took place in incubation buffer (50 mM Tris, 10 mM MgCl$_2$, 0.1% BSA, pH 7.4).

Membrane Preparation:

CHO-K1 cells with stably expressed human vasopressin V1a receptor (clone 5) were harvested and homogenized in 50 mM Tris-HCl and in the presence of protease inhibitors (Roche complete Mini # 1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4. In the assay mixture (250 µl), membranes (20 µg/ml protein in incubation buffer) from CHO-K1 cells with stably expressed human V1a receptors (cell line hV1a_5_CHO) were incubated with 0.04 nM $^{125}$I-AVP (8-Arg-vasopressin, NEX 128) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 µM AVP (Bachem # H1780). Triplicate determinations were carried out. After incubation (60 minutes at room temperature), the free radioligand was filtered off by vacuum filtration (Skatron cell harvester 7000) through Wathman GF/B glass fiber filter mats, and the filters were transferred into scintillation vials.

The liquid scintillation measurement took place in a model 2000 or 2200CA Tricarb instrument (Packard). Conversion of the measured cpm into dpm was carried out with the aid of a standard quench series.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Vasopressin V2 Receptor Binding Assay:
Substances:

The test substances were dissolved in a concentration of 10$^{-2}$ M in DMSO. Further dilution of these DMSO solutions took place in incubation buffer (50 mM Tris, 10 mM MgCl$_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini # 1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (250 µl), membranes (50 µg/ml protein in incubation buffer) from CHO-K1 cells with stably expressed human V2 receptors (cell line hV2_23_CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem # H1780). Triplicate determinations were carried out.

After incubation (60 minutes at room temperature), the free radioligand was filtered off by vacuum filtration (Skatron cell harvester 7000) through Wathman GF/B glass fiber filter mats, and the filters were transferred into scintillation vials.

The liquid scintillation measurement took place in a model 2000 or 2200CA Tricarb instrument (Packard). Conversion of the measured cpm into dpm was carried out with the aid of a standard quench series.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki.

4. Oxytocin Receptor Binding Assay

Substances:

The substances were dissolved in a concentration of $10^{-2}$ M in DMSO and diluted with incubation buffer (50 mM Tris, 10 mM $MgCl_2$, 0.1% BSA, pH 7.4).

Cell Preparation:

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. The lyzed cells were then centrifuged at 750×g at 4° C. for 20 minutes, the residue was taken up in incubation buffer, and aliquots of $10^7$ cells/ml were prepared. The aliquots were frozen at −80° C. until used.

Binding Assay:

On the day of the experiment, the cells were thawed, diluted with incubation buffer and homogenized using a Multipette Combitip (Eppendorf, Hamburg). The reaction mixture of 0.250 ml was composed of 2 to $5×10^4$ recombinant cells, 3-4 nM $^3$H-oxytocin (PerkinElmer, NET 858) in the presence of test substance (inhibition plot) or only incubation buffer (total binding). The nonspecific binding was determined with $10^{-6}$ M oxytocin (Bachem AG, H2510). Triplicate determinations were set up. Bound and free radioligand were separated by filtration under vacuum with Whatman GF/B glass fiber filters with the aid of a Skatron cell harvester 7000.

The bound radioactivity was determined by liquid scintillation measurement in a Tricarb Beta counter, model 2000 or 2200CA (Packard).

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant hOT receptors is 7.6 nM and was used to determine the Ki.

5. Determination of the Microsomal Half-life:

The metabolic stability of the compounds of the invention was determined in the following assay.

The test substances were incubated in a concentration of 0.5 µM as follows: 0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T1/2) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln2/T1/2/(content of microsomal protein in mg/ml)×1000 [ml/min/mg] (modified from references: Di, The Society for Biomoleculur Screening, 2003, 453-462; Obach, DMD, 1999 vol 27. N 11, 1350-1359).

6. Methods for in vitro Determination of the Cytochrome P450 (CYP) Inhibition

Luminescent Substrates for 2C9 and 3A4:

0.4 mg/ml human liver microsomes are preincubated with the test substances to be investigated (0-20 µM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam Cyp 3A4 Time-dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 µM (or 50 µM) test substance in 50 mM potassium phosphate buffer for 5 min. The reaction is started with NADPH. After 30 min 4 µM midazolam (final concentration) are added, and incubation is continued for 10 min. 75 µl of the reaction solution are removed after 10 min, and stopped with 150 µl of acetonitrile solution.

Coincubation:

0.05 mg/ml microsomal protein (human liver microsomes) are preincubated with 4 µM midazolam (final concentration) and 0-10 µM (or 50 µM) test substance in 50 mM potassium phosphate buffer for 5 min. The reaction is started with NADPH. 75 µl of the reaction solution are removed after 10 min and stopped with 150 µl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

7. Method for Determining the Solubility in Water (in mg/ml)

The solubility in water of the compounds of the invention can be determined for example by the so-called shake flask method (as specified in *ASTM International: E* 1148-02, *Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

8. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the V1a receptor and the oxytocin receptor.

The results are listed in table 1. The numbers of the compounds refer to the synthesis examples.

TABLE 1

| Example | $K_i$(h-V1b)* [nM] | $K_i$(h-V1a)/$K_i$(h-V1b)* | $K_i$(h-OT)/$K_i$(h-V1b)* |
| --- | --- | --- | --- |
| 2 | ++ | +++ | ++ |
| 3 | ++ | +++ | + |
| 4 | ++ | +++ | ++ |
| 5 | ++ | +++ | +++ |
| 6 | ++ | +++ | ++ |
| 7 | ++ | +++ | ++ |
| 13 | + | + | ++ |
| 14 | ++ | + | ++ |
| 15 | ++ | ++ | +++ |
| 16 | ++ | +++ | +++ |
| 17 | ++ | + | + |
| 24 | ++ | +++ | + |
| 25 | + | ++ | + |
| 26 | + | ++ | +++ |
| 27 | + | + | +++ |
| 28 | + | + | +++ |
| 29 | ++ | ++ | + |
| 30 | ++ | +++ | +++ |
| 31 | +++ | +++ | +++ |
| 33 | +++ | +++ | +++ |
| 34 | ++ | + | +++ |
| 35 | ++ | + | +++ |
| 37 | ++ | ++ | +++ |
| 38 | ++ | + | + |
| 40 | ++ | ++ | ++ |
| 41 | ++ | ++ | ++ |
| 43 | ++ | +++ | + |
| 50 | ++ | + | +++ |
| 57 | + | ++ | +++ |
| 59 | ++ | ++ | +++ |
| 60 | ++ | ++ | ++ |
| 68 | ++ | + | ++ |
| 70 | ++ | ++ | + |
| 73 | + | +++ | ++ |
| 74 | ++ | +++ | +++ |
| 75 | + | ++ | +++ |
| 77 | ++ | ++ | ++ |
| 79 | + | ++ | +++ |

*h = human
Key:

| | $K_i$(V1b) | $K_i$(h-V1a)/$K_i$(h-V1b) | $K_i$(h-V1a)/$K_i$(h-OT) |
| --- | --- | --- | --- |
| + | >10-100 nm | 10-<25 | 10-<25 |
| ++ | 1-10 nm | 25-75 | 25-75 |
| +++ | <1 nm | >75 | >75 |

The invention claimed is:

1. A compound of the formula I

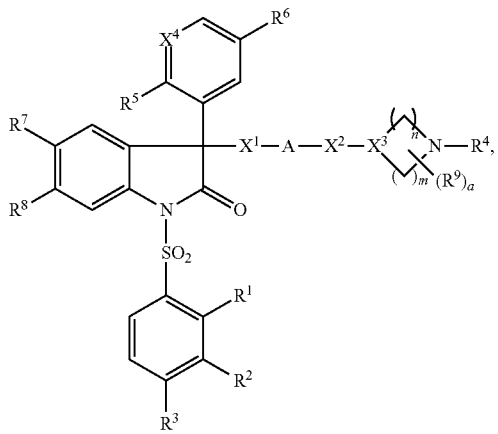

in which
X$^1$ is —O—, —O—CH$_2$—, —O—C(=O)—, —NR$^{11}$—, —NR$^{11}$—CH$_2$— or —NR$^{11}$—C(=O)—;
X$^2$ is a single bond, CO or CH$_2$;
X$^3$ is N or CH;
X$^4$ is N or CH;
A is phenylene or 6-membered hetarylene with 1 or 2 nitrogen atoms as ring members, where phenylene or hetarylene may be substituted by 1 or 2 radicals R$^{10}$;
R$^1$ and R$^3$ are independently of one another hydrogen, C$_1$-C$_3$-alkyl, C$_1$-C$_3$-fluoroalkyl, C$_1$-C$_3$-alkoxy, C$_1$-C$_3$-fluoroalkoxy, halogen or CN;
R$^2$ is hydrogen or methoxy;
where at least one of the radicals R$^1$, R$^2$ and R$^3$ is hydrogen;
R$^4$ is hydrogen or C$_1$-C$_4$-alkyl;
R$^5$ is ethoxy, fluorinated ethoxy, fluoromethoxy, difluoromethoxy, trifluoromethoxy or isopropoxy;
R$^6$ is hydrogen or methyl;
R$^7$ is hydrogen, I, Br, Cl, F or CN;
R$^8$ is hydrogen, I, Br, Cl, F or CN;
R$^9$ is C$_1$-C$_3$-alkyl or C$_1$-C$_3$-fluoroalkyl;
R$^{10}$ is C$_1$-C$_3$-alkyl, C$_1$-C$_3$-fluoroalkyl, C$_1$-C$_3$-alkoxy or C$_1$-C$_3$-fluoroalkoxy;
R$^{11}$ is hydrogen, C$_1$-C$_4$-alkyl, C$_1$-C$_4$-fluoroalkyl, C$_1$-C$_4$-alkoxy or C$_1$-C$_4$-fluoroalkoxy;
a is 0, 1 or 2; and
m and n are independently of one another 1 or 2;
or a pharmaceutically acceptable salt thereof.

2. A compound of claim 1, in which $R^1$ is hydrogen, methoxy, ethoxy, fluoromethoxy, difluoromethoxy or trifluoromethoxy.

3. A compound of claim 1, in which $R^2$ is hydrogen.

4. A compound of claim 1, in which $R^3$ is hydrogen or methoxy.

5. A compound of claim 1, in which $R^4$ is hydrogen, methyl or ethyl.

6. A compound of claim 1, in which $R^5$ is ethoxy or fluorinated ethoxy.

7. A compound of claim 6, in which $R^5$ is ethoxy, 2,2-difluoroethoxy or 2,2,2-trifluoroethoxy.

8. A compound of claim 1, in which $R^6$ is hydrogen.

9. A compound of claim 1, in which $R^7$ and $R^8$ are not simultaneously CN.

10. A compound of claim 1, in which $R^7$ is CN and $R^8$ is H or F.

11. A compound of claim 1, in which $R^7$ is I and $R^8$ is H or F.

12. A compound of claim 1, in which $R^7$ is Cl and $R^8$ is H or F.

13. A compound of claim 1, in which $R^9$ is methyl or ethyl.

14. A compound of claim 1, in which $R^{10}$ is methyl or methoxy.

15. A compound of claim 1, in which $R^{11}$ is H.

16. A compound of claim 1, in which a is 0.

17. A compound of claim 1, in which $X^1$ is —O—C(=O)—, —NH—, —NH—CH$_2$— or —NH—C(=O)—.

18. A compound of claim 17, in which $X^1$ is —NH—CH$_2$—.

19. A compound of claim 1, in which $X^2$ is a single bond.

20. A compound of claim 1, in which $X^3$ is N, and m and n are both 2.

21. A compound of claim 1, in which $X^3$ is CH, and m and n are both 2, or are both 1, or m is 1 and n is 2.

22. A compound of claim 1, in which $X^4$ is N.

23. A compound of claim 1, in which A is phenylene.

24. A compound of claim 23, in which A is 1,4- or 1,3-phenylene.

25. A compound of claim 1, in which A is pyridylene or pyrimidylene.

26. A compound of claim 25, in which A is 3,5- or 3,6-pyridylene.

27. A compound of claim 1, in which
$R^1$ is H or methoxy;
$R^2$ is H;
$R^3$ is methoxy;
$R^4$ is H, methyl or ethyl;
$R^5$ is ethoxy; $R^6$ is H;
$R^7$ is CN;
$R^8$ is H or F;
$X^1$ is —NH— or —NHCH$_2$—;
$X^2$ is a single bond;
$X^3$ is N;
$X^4$ is N;
A is 1,4-phenylene;
a is 0; and
m and n are 2.

28. A compound of the formula XVIII

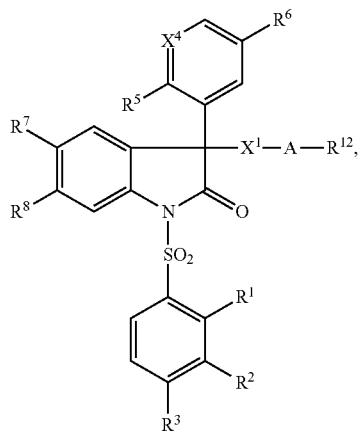

in which
$X^1$ is —O—, —O—CH$_2$—, —O—C(=O)—, —NR$^{11}$—, —NR$^{11}$—CH$_2$— or —NR$^{11}$—C(=O)—;
$X^4$ is N or CH;
A is phenylene or 6-membered hetarylene with 1 or 2 nitrogen atoms as ring members, where phenylene or hetarylene may be substituted by 1 or 2 radicals $R^{10}$;
$R^1$ and $R^3$ are independently of one another hydrogen, $C_1$-$C_3$-alkyl, $C_1$-$C_3$-fluoroalkyl, $C_1$-$C_3$-alkoxy, $C_1$-$C_3$-fluoroalkoxy, halogen or CN;
$R^2$ is hydrogen or methoxy;
where at least one of the radicals $R^1$, $R^2$ and $R^3$ is hydrogen;
$R^5$ is ethoxy, fluorinated ethoxy, fluoromethoxy, difluoromethoxy, trifluoromethoxy or isopropoxy;
$R^6$ is hydrogen or methyl;
$R^7$ is hydrogen, I, Br, Cl, F or CN;
$R^8$ is hydrogen, I, Br, Cl, F or CN; and
$R^{12}$ is halogen, CN, OR$^a$ or NR$^b$R$^c$, in which
$R^a$ is H, $C_1$-$C_4$-alkyl, phenyl or benzyl; and
$R^b$ and $R^c$ are independently of one another H, $C_1$-$C_4$-alkyl, $C_1$-$C_4$-alkoxy, phenyl or benzyl;
or a pharmaceutically acceptable salt thereof.

29. A compound of claim 28, in which $R^{12}$ is halogen.

30. A method for the treatment of diseases selected from hypertension, pulmonary hypertension, myocardial infarction, coronary spasm, unstable angina, and ischemias of the heart, the method comprising administering a compound of claim 1 or a pharmaceutically acceptable salt to a subject in need thereof.

31. The compound of claim 1, or a pharmaceutically acceptable salt thereof, selected from the group consisting of:
1-(2,4-Dimethoxyphenylsulfonyl)-3-(2-ethoxypyridin-3-yl)-5-iodo-2-oxo-2,3-dihydro-1H-indol-3-yl-4-(4-methylpiperazin-1-yl)benzoate;
5-Cyano-3-(2-ethoxypyridin-3-yl)-1-(4-methoxyphenylsulfonyl)-2-oxo-2,3-dihydro-1H-indol-3-yl-4-(4-methylpiperazin-1-yl)benzoate;
5-Cyano-1-(2,4-dimethoxyphenylsulfonyl)-3-(2-ethoxypyridin-3-yl)-2-oxo-2,3-dihydro-1H-indol-3-yl 4-(4-methylpiperazin-1-yl)benzoate;
N-[5-Cyano-3-(2-ethoxypyridin-3-yl)-1-(4-methoxyphenylsulfonyl)-2-oxo-2,3-dihydro-1H-indol-3-yl]-4-(4-methylpiperazin-1-yl)benzamide;

N-[5-Cyano-3-(2-ethoxypyridin-3-yl)-1-(4-methoxyphenylsulfonyl)-2-oxo-2,3-dihydro-1H-indol-3-yl]-4-(4-ethylpiperazin-1-yl)benzamide;

N-[5-Cyano-1-(2,4-dimethoxyphenylsulfonyl)-3-(2-ethoxypyridin-3-yl)-2-oxo-2,3-dihydro-1H-indol-3-yl]-4-(4-methylpiperazin-1-yl)benzamide;

N-[5-Cyano-1-(2,4-dimethoxyphenylsulfonyl)-3-(2-ethoxypyridin-3-yl)-2-oxo-2,3-dihydro-1H-indol-3-yl]-4-(4-ethylpiperazin-1-yl)benzamide;

N-[1-[4-(2,2-Difluoroethoxy)phenylsulfonyl]-3-(2-ethoxypyridin-3-yl)-5-iodo-2-oxo-2,3-dihydro-1H-indol-3-yl]-4-(4-methylpiperazin-1-yl)benzamide;

1-(2,4-Dimethoxyphenylsulfonyl)-3-(2-ethoxypyridin-3-yl)-5-iodo-3-[4-(4-methylpiperazin-1-yl)benzylamino]-1,3-dihydroindol-2-one;

1-(2,4-Dimethoxyphenylsulfonyl)-3-(2-ethoxypyridin-3-yl)-5-iodo-3-(4-piperazin-1-yl-benzylamino)-1,3-dihydroindol-2-one;

5-Chloro-3-(2-ethoxypyridin-3-yl)-1-(4-methoxyphenylsulfonyl)-3-[4-(4-methylpiperazin-1-yl)-benzylamino]-1,3-dihydroindol-2-one;

5-Chloro-3-(2-ethoxypyridin-3-yl)-6-fluoro-1-(4-methoxyphenylsulfonyl)-3-[4-(4-methylpiperazin-1-yl)benzylamino]-1,3-dihydroindol-2-one;

6-Chloro-3-(2-ethoxypyridin-3-yl)-5-fluoro-1-(4-methoxyphenylsulfonyl)-3-[4-(4-methylpiperazin-1-yl)benzylamino]-1,3-dihydroindol-2-one;

5,6-Difluoro-3-(2-ethoxypyridin-3-yl)-1-(4-methoxyphenylsulfonyl)-3-[4-(4-methylpiperazin-1-yl)benzylamino]-1,3-dihydroindol-2-one;

3-(2-Ethoxypyridin-3-yl)-5-fluoro-1-(4-methoxyphenylsulfonyl)-3-[4-(4-methylpiperazin-1-yl)benzylamino]-1,3-dihydroindol-2-one;

3-(2-Ethoxypyridin-3-yl)-1-(4-methoxyphenylsulfonyl)-3-[4-(4-methylpiperazin-1-yl)-benzylamino]-2-oxo-2,3-dihydro-1H-indole-5-carbonitrile;

1-(2,4-Dimethoxyphenylsulfonyl)-3-(2-ethoxypyridin-3-yl)-3-[4-(4-methylpiperazin-1-yl)-benzylamino]-2-oxo-2,3-dihydro-1H-indole-5-carbonitrile;

3-(2-Ethoxypyridin-3-yl)-1-(4-methoxy-2-trifluoromethoxyphenylsulfonyl)-3-[4-(4-methylpiperazin-1-yl)benzylamino]-2-oxo-2,3-dihydro-1H-indole-5-carbonitrile;

3-(2-Ethoxypyridin-3-yl)-3-[4-(4-methylpiperazin-1-yl)benzylamino]-2-oxo-1-(4-trifluoromethoxyphenylsulfonyl)-2,3-dihydro-1H-indole-5-carbonitrile;

3-(2-Ethoxypyridin-3-yl)-3-[4-(4-methylpiperazin-1-yl)benzylamino]-2-oxo-1-[4-(2,2,2-trifluoroethoxy)phenylsulfonyl]-2,3-dihydro-1H-indole-5-carbonitrile;

1-[4-(2,2-Difluoroethoxy)phenylsulfonyl]-3-(2-ethoxypyridin-3-yl)-3-[4-(4-methylpiperazin-1-yl)benzylamino]-2-oxo-2,3-dihydro-1H-indole-5-carbonitrile;

3-(2-Ethoxypyridin-3-yl)-1-[4-(2-fluoroethoxy)phenylsulfonyl]-3-[4-(4-methylpiperazin-1-yl)-benzylamino]-2-oxo-2,3-dihydro-1H-indole-5-carbonitrile;

1-(4-Difluoromethoxyphenylsulfonyl)-3-(2-ethoxypyridin-3-yl)-3-[4-(4-methylpiperazin-1-yl)benzylamino]-2-oxo-2,3-dihydro-1H-indole-5-carbonitrile;

3-(2-Ethoxypyridin-3-yl)-1-(2-methoxyphenylsulfonyl)-3-[4-(4-methylpiperazin-1-yl)-benzylamino]-2-oxo-2,3-dihydro-1H-indole-5-carbonitrile;

3-(2-Ethoxypyridin-3-yl)-1-(3-methoxyphenylsulfonyl)-3-[4-(4-methylpiperazin-1-yl)-benzylamino]-2-oxo-2,3-dihydro-1H-indole-5-carbonitrile;

1-(4-Chlorophenylsulfonyl)-3-(2-ethoxypyridin-3-yl)-3-[4-(4-methylpiperazin-1-yl)-benzylamino]-2-oxo-2,3-dihydro-1H-indole-5-carbonitrile;

1-Phenylsulfonyl-3-(2-ethoxypyridin-3-yl)-3-[4-(4-methylpiperazin-1-yl)benzylamino]-2-oxo-2,3-dihydro-1H-indole-5-carbonitrile;

1-(4-Cyanophenylsulfonyl)-3-(2-ethoxypyridin-3-yl)-3-[4-(4-methylpiperazin-1-yl)-benzylamino]-2-oxo-2,3-dihydro-1H-indole-5-carbonitrile;

1-(2,4-Dimethoxyphenylsulfonyl)-3-(2-ethoxypyridin-3-yl)-2-oxo-3-(4-piperazin-1-yl-benzylamino)-2,3-dihydro-1H-indole-5-carbonitrile;

3-(2-Ethoxypyridin-3-yl)-1-(4-methoxyphenylsulfonyl)-2-oxo-3-(4-piperazin-1-yl-benzylamino)-2,3-dihydro-1H-indole-5-carbonitrile;

3-(2-Ethoxypyridin-3-yl)-3-[4-(4-ethylpiperazin-1-yl)benzylamino]-1-(4-methoxy-phenylsulfonyl)-2-oxo-2,3-dihydro-1H-indole-5-carbonitrile;

1-(2,4-Dimethoxyphenylsulfonyl)-3-(2-ethoxypyridin-3-yl)-3-[4-(4-ethylpiperazin-1-yl)-benzylamino]-2-oxo-2,3-dihydro-1H-indole-5-carbonitrile;

3-(2-Ethoxypyridin-3-yl)-6-fluoro-1-(4-methoxyphenylsulfonyl)-3-[4-(4-methylpiperazin-1-yl)benzylamino]-2-oxo-2,3-dihydro-1H-indole-5-carbonitrile;

3-(2-Ethoxypyridin-3-yl)-6-fluoro-1-(4-methoxyphenylsulfonyl)-2-oxo-3-(4-piperazin-1-yl-benzylamino)-2,3-dihydro-1H-indole-5-carbonitrile;

3-(2-Ethoxypyridin-3-yl)-3-[4-(4-ethylpiperazin-1-yl)benzylamino]-6-fluoro-1-(4-methoxyphenylsulfonyl)-2-oxo-2,3-dihydro-1H-indole-5-carbonitrile;

1-[4-(2,2-Difluoroethoxy)phenylsulfonyl]-3-(2-ethoxypyridin-3-yl)-6-fluoro-3-[4-(4-methylpiperazin-1-yl)benzylamino]-2-oxo-2,3-dihydro-1H-indole-5-carbonitrile;

3-(2-Ethoxyphenyl)-1-(4-methoxyphenylsulfonyl)-3-[4-(4-methylpiperazin-1-yl)-benzylamino]-2-oxo-2,3-dihydro-1H-indole-5-carbonitrile;

1-(2,4-Dimethoxyphenylsulfonyl)-3-(2-ethoxypyridin-3-yl)-5-iodo-3-[3-(4-methylpiperazin-1-yl)benzylamino]-1,3-dihydroindol-2-one;

3-(2-Ethoxypyridin-3-yl)-5-iodo-1-(4-methoxy-2-trifluoromethoxyphenylsulfonyl)-3-[3-(4-methylpiperazin-1-yl)benzylamino]-1,3-dihydroindol-2-one;

3-(2-Ethoxypyridin-3-yl)-5-iodo-1-(4-methoxyphenylsulfonyl)-3-[3-(4-methylpiperazin-1-yl)-benzylamino]-1,3-dihydroindol-2-one;

3-(2-Ethoxypyridin-3-yl)-5-iodo-1-(2-methoxyphenylsulfonyl)-3-[3-(4-methylpiperazin-1-yl)-benzylamino]-1,3-dihydroindol-2-one;

1-(2,4-Dimethoxyphenylsulfonyl)-3-(2-ethoxypyridin-3-yl)-3-[3-(4-methylpiperazin-1-yl)-benzylamino]-2-oxo-2,3-dihydro-1H-indole-5-carbonitrile;

3-(2-Ethoxypyridin-3-yl)-1-(4-methoxyphenylsulfonyl)-3-[3-(4-methylpiperazin-1-yl)-benzylamino]-2-oxo-2,3-dihydro-1H-indole-5-carbonitrile;

3-(2-Ethoxypyridin-3-yl)-1-(2-methoxyphenylsulfonyl)-3-[3-(4-methylpiperazin-1-yl)-benzylamino]-2-oxo-2,3-dihydro-1H-indole-5-carbonitrile;

1-(2,4-Dimethoxyphenylsulfonyl)-3-(2-ethoxypyridin-3-yl)-3-[2-(4-methylpiperazin-1-yl)-benzylamino]-2-oxo-2,3-dihydro-1H-indole-5-carbonitrile;

3-(2-Ethoxypyridin-3-yl)-1-(4-methoxyphenylsulfonyl)-3-[2-(4-methylpiperazin-1-yl)-benzylamino]-2-oxo-2,3-dihydro-1H-indole-5-carbonitrile;

3-(2-Ethoxypyridin-3-yl)-1-(2-methoxyphenylsulfonyl)-3-[2-(4-methylpiperazin-1-yl)-benzylamino]-2-oxo-2,3-dihydro-1H-indole-5-carbonitrile;

1-(2,4-Dimethoxyphenylsulfonyl)-3-(2-ethoxypyridin-3-yl)-3-[4-(4-ethylpiperazin-1-yl)-phenylamino]-5-iodo-1,3-dihydroindol-2-one;

1-(2,4-Dimethoxyphenylsulfonyl)-3-(2-ethoxypyridin-3-yl)-5-iodo-3-[4-(4-methylpiperazin-1-yl)phenylamino]-1,3-dihydroindol-2-one;

3-(2-Ethoxypyridin-3-yl)-5-iodo-1-(4-methoxyphenylsulfonyl)-3-[4-(4-methylpiperazin-1-yl)-phenylamino]-1,3-dihydroindol-2-one;

5-Chloro-3-(2-ethoxypyridin-3-yl)-1-(4-methoxyphenylsulfonyl)-3-[4-(4-methylpiperazin-1-yl)phenylamino]-1,3-dihydroindol-2-one;

5-Chloro-3-(2-ethoxypyridin-3-yl)-6-fluoro-1-(4-methoxyphenylsulfonyl)-3-[4-(4-methylpiperazin-1-yl)phenylamino]-1,3-dihydroindol-2-one;

6-Chloro-3-(2-ethoxypyridin-3-yl)-5-fluoro-1-(4-methoxyphenylsulfonyl)-3-[4-(4-methylpiperazin-1-yl)phenylamino]-1,3-dihydroindol-2-one;

3-(2-Ethoxypyridin-3-yl)-5,6-difluoro-1-(4-methoxyphenylsulfonyl)-3-[4-(4-methylpiperazin-1-yl)phenylamino]-1,3-dihydroindol-2-one;

1-(2,4-Dimethoxyphenylsulfonyl)-3-(2-ethoxypyridin-3-yl)-3-[4-(4-methylpiperazin-1-yl)-phenylamino]-2-oxo-2,3-dihydro-1H-indole-5-carbonitrile;

1-(2,4-Dimethoxyphenylsulfonyl)-3-(2-ethoxypyridin-3-yl)-3- [4-(4-ethylpiperazin-1-yl)-phenylamino]-2-oxo-2,3-dihydro-1H-indole-5-carbonitrile;

3-(2-Ethoxypyridin-3-yl)-3-[4-(4-ethylpiperazin-1-yl)phenylamino]-1-(4methoxyphenylsulfonyl)-2-oxo-2,3-dihydro-1H-indole-5-carbonitrile;

3-(2-Ethoxypyridin-3-yl)-3-[4-(4-ethylpiperazin-1-yl)phenylamino]-1-(2-methoxyphenylsulfonyl)-2-oxo-2,3-dihydro-1H-indole-5-carbonitrile;

3-(2-Ethoxypyridin-3-yl)-6-fluoro-1-(4-methoxyphenylsulfonyl)-3-[4-(4-methylpiperazin-1-yl)phenylamino]-2-oxo-2,3-dihydro-1H-indole-5-carbonitrile;

1-(2,4-Dimethoxyphenylsulfonyl)-3-(2-ethoxypyridin-3-yl)-5-iodo-3-[3-(4-methylpiperazin-1-yl)phenylamino]-1,3-dihydroindol-2-one;

3-(2-Ethoxypyridin-3-yl)-1-(4-methoxyphenylsulfonyl)-3- [3-(4-methylpiperazin-1-yl)-phenylamino]-2-oxo-2,3-dihydro-1H-indole-5-carbonitrile;

1-(2,4-Dimethoxyphenylsulfonyl)-3-(2-ethoxypyridin-3-yl)-3- [3-(4-methylpiperazin-1-yl)-phenylamino]-2-oxo-2,3-dihydro-1H-indole-5-carbonitrile;

3-(4-Azetidin-3-ylphenylamino)-1-(2,4-dimethoxyphenylsulfonyl)-3-(2-ethoxypyridin-3-yl)-5-iodo-1,3-dihydroindol-2-one;

1-(2,4-Dimethoxyphenylsulfonyl)-3-(2-ethoxypyridin-3-yl)-3- [4-(1-ethylazetidin-3-yl)-phenylamino]-5-iodo-1,3-dihydroindol-2-one;

3-(4-Azetidin-3-ylphenylamino)-3-(2-ethoxypyridin-3-yl)-5-iodo-1-(4-methoxyphenylsulfonyl)-1,3-dihydroindol-2-one;

3-(2-Ethoxypyridin-3-yl)-3-[4-(1-ethylazetidin-3-yl)phenylamino]-5-iodo-1-(4-methoxyphenylsulfonyl)-1,3-dihydroindol-2-one;

1-(2,4-Dimethoxyphenylsulfonyl)-3-(2-ethoxypyridin-3-yl)-5-iodo-3-[6-(4-methylpiperazin-1-yl)pyridin-3-ylamino]-1,3-dihydroindol-2-one;

3-(2-Ethoxypyridin-3-yl)-5-iodo-1-(4-methoxyphenylsulfonyl)-3-[6-(4-methylpiperazin-1-yl)-pyridin-3-ylamino]-1,3-dihydroindol-2-one;

1-Phenylsulfonyl-3-(2-ethoxypyridin-3-yl)-5-iodo-3-[6-(4-methylpiperazin-1-yl)pyridin-3-ylamino]-1,3-dihydroindol-2 -one;

3-(2-Ethoxypyridin-3-yl)-5-iodo-1-(4-methoxyphenylsulfonyl)-3-[4-(4-methylpiperazin-1-carbonyl) phenylamino]-1,3-dihydroindol-2-one;

1-(2,4-Dimethoxyphenylsulfonyl)-3-(2-ethoxypyridin-3-yl)-5-iodo-3-[4-(4-methylpiperazin-1-carbonyl)phenylamino]-1,3-dihydroindol-2-one;

3-(2-Ethoxypyridin-3-yl)-1-(4-methoxyphenylsulfonyl)-3-[4-(4-methylpiperazin-1-carbonyl) -phenylamino]-2-oxo-2,3-dihydro-1H-indole-5-carbonitrile;

1-(2,4-Dimethoxyphenylsulfonyl)-3-(2-ethoxypyridin-3-yl)-3-[4-(4-methylpiperazin-1-carbonyl)phenylamino]-2-oxo-2,3-dihydro-1H-indole-5-carbonitrile;

1-(2,4-Dimethoxyphenylsulfonyl)-3-(2-ethoxypyridin-3-yl)-3-[4-(4-methylpiperazin-1-ylmethyl) phenylamino]-2-oxo-2,3-dihydro-1H-indole-5-carbonitrile;

3-(2-Ethoxypyridin-3-yl)-1-(4-methoxyphenylsulfonyl)-3- [4-(4-methylpiperazin-1-ylmethyl)-phenylamino]-2-oxo-2,3-dihydro-1H-indole-5-carbonitrile;

3-(2-(2,2-Difluoroethoxy)pyridin-3-yl)-1-(4-methoxyphenylsulfonyl)-3-[4-(4-methylpiperazin-1-yl)benzylamino]-2-oxo-2,3-dihydro-1H-indole-5-carbonitrile;

1-(4-Methoxyphenylsulfonyl)-3-(2-(2,2,2-trifluoroethoxy)pyridin-3-yl)-3-[4-(4-methylpiperazin-1-yl)benzylamino]-2-oxo-2,3-dihydro-1H-indole-5-carbonitrile;

3-(2-(2,2-Difluoroethoxy)phenyl)-1-(4-methoxyphenylsulfonyl)-3-[4-(4-methylpiperazin-1-yl)-benzylamino]-2-oxo-2,3-dihydro-1H-indole-5-carbonitrile;

3-[4-(4-Ethylpiperazin-1-yl)phenylamino]-1-(4-methoxyphenylsulfonyl)-3-(2-(2,2-difluoroethoxy)pyridin-3-yl)-2-oxo-2,3-dihydro-1H-indole-5-carbonitrile;

3-[4-(4-Ethylpiperazin-1-yl)phenylamino]-1-(4-methoxyphenylsulfonyl)-3-(2-(2,2,2-trifluoroethoxy)pyridin-3-yl)-2-oxo-2,3-dihydro-1H-indole-5-carbonitrile;

3-(2-(2,2-Difluoroethoxy)phenyl)-3-[4-(4-ethylpiperazin-1-yl)phenylamino]-1-(4-methoxyphenylsulfonyl)-2-oxo-2,3-dihydro-1H-indole-5-carbonitrile; and 1-(2,4-Dimethoxyphenylsulfonyl)-3-[4-(4-methylpiperazin-1-yl)phenylamino]-3-(2-(trifluoromethoxy)phenyl)-2-oxo-2,3-dihydro-1H-indole-5-carbonitrile.

32. A pharmaceutical composition comprising at least one compound of the formula I as defined in claim 1 and/or at least one pharmaceutically acceptable salt or prodrug thereof and at least one pharmaceutically acceptable carrier.

* * * * *

UNITED STATES PATENT AND TRADEMARK OFFICE
CERTIFICATE OF CORRECTION

PATENT NO. : 8,629,148 B2
APPLICATION NO. : 12/810561
DATED : January 14, 2014
INVENTOR(S) : Braje et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 451 days.

Signed and Sealed this
Twelfth Day of May, 2015

Michelle K. Lee
*Director of the United States Patent and Trademark Office*